US009040495B2

(12) United States Patent
Smolke et al.

(10) Patent No.: US 9,040,495 B2
(45) Date of Patent: May 26, 2015

(54) GENERAL COMPOSITION FRAMEWORK FOR LIGAND-CONTROLLED RNA REGULATORY SYSTEMS

(75) Inventors: Christina D. Smolke, Pasadena, CA (US); Maung Nyan Win, San Gabriel, CA (US); Chase Beisel, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/585,919

(22) Filed: Aug. 15, 2012

(65) Prior Publication Data

US 2013/0102651 A1    Apr. 25, 2013

Related U.S. Application Data

(63) Continuation of application No. 12/228,665, filed on Aug. 14, 2008, now abandoned.

(60) Provisional application No. 60/966,398, filed on Aug. 28, 2007.

(51) Int. Cl.
| C12N 15/11 | (2006.01) |
| C12Q 1/68 | (2006.01) |
| C12N 15/113 | (2010.01) |
| A61K 31/7088 | (2006.01) |
| C12N 15/63 | (2006.01) |
| G01N 33/537 | (2006.01) |
| G01N 33/542 | (2006.01) |
| C07H 21/04 | (2006.01) |

(52) U.S. Cl.
CPC .......... *C12N 15/113* (2013.01); *A61K 31/7088* (2013.01); *C12N 15/111* (2013.01); *C12N 15/63* (2013.01); *G01N 33/537* (2013.01); *G01N 33/542* (2013.01); *C12N 2310/14* (2013.01); *C12N 2310/16* (2013.01); *C12N 2310/531* (2013.01); *C12N 2320/00* (2013.01)

(58) Field of Classification Search
CPC ............. C12N 2310/14; C12N 15/111; C12N 2310/16; C12N 15/113; C12Q 1/6897; C12Q 2525/205
See application file for complete search history.

(56) References Cited

U.S. PATENT DOCUMENTS

| 4,235,871 A | 11/1980 | Papahadjopoulos et al. |
| 4,426,330 A | 1/1984 | Sears |
| 4,501,728 A | 2/1985 | Geho et al. |
| 4,534,899 A | 8/1985 | Sears |
| 4,737,323 A | 4/1988 | Martin et al. |
| 4,837,028 A | 6/1989 | Allen |
| 4,897,355 A | 1/1990 | Eppstein et al. |
| 5,013,556 A | 5/1991 | Woodle et al. |
| 5,013,830 A | 5/1991 | Ohtsuka et al. |
| 5,093,246 A | 3/1992 | Cech et al. |
| 5,108,921 A | 4/1992 | Low et al. |
| 5,176,996 A | 1/1993 | Hogan et al. |
| 5,213,804 A | 5/1993 | Martin et al. |
| 5,214,135 A | 5/1993 | Srivastava et al. |
| 5,227,170 A | 7/1993 | Sullivan |
| 5,256,775 A | 10/1993 | Froehler |
| 5,264,221 A | 11/1993 | Tagawa et al. |
| 5,264,423 A | 11/1993 | Cohen et al. |
| 5,264,564 A | 11/1993 | Matteucci |
| 5,270,163 A | 12/1993 | Gold et al. |
| 5,276,019 A | 1/1994 | Cohen et al. |
| 5,354,844 A | 10/1994 | Beug et al. |
| 5,356,633 A | 10/1994 | Woodle et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,500,357 A | 3/1996 | Taira et al. |
| 5,512,295 A | 4/1996 | Kornberg et al. |
| 5,521,291 A | 5/1996 | Curiel et al. |

(Continued)

FOREIGN PATENT DOCUMENTS

| AU | 2004206255 A1 | 8/2004 |
| WO | WO-88/04300 A1 | 6/1988 |

(Continued)

OTHER PUBLICATIONS

Gardner et al., "Construction of a genetic toggle switch in *Escherichia coli*," *Nature*, 403:339-342 (2000).
Aagaard et al., "Engineering and optimization of the miR-1 06b cluster for ectopic expression of multiplexed anti-HIV RNAs," *Gene Ther.*, 15:1536-1549 (2008).
Aagard and Rossi, "RNAi Therapeutics: Principles, Prospects and Challenges," *Adv. Drug Deilv. Rev.*, 59(2-3):75-86 (2007).
Abbas-Terki et al., "Lentiviral-mediated RNA interference," *Human Gene Ther.*, 13:2197-2201 (2002).
Agrawal et al., "RNA interference: biology, mechanism, and applications," *Microbiology and Molecular Biology Reviews*, 67:657-685 (2003).

(Continued)

*Primary Examiner* — Dana Shin
(74) *Attorney, Agent, or Firm* — McCarter & English, LLP; Yu Lu; Jin Wang

(57) ABSTRACT

The invention provides an improved design for the construction of extensible nucleic acid-based, ligand-controlled regulatory systems, and the nucleic acid regulatory systems resulting therefrom. The invention contemplates improving the design of the switches (ligand-controlled regulatory systems) through the design of an information transmission domain (ITD). The improved ITD eliminates free-floating ends of the switching and the competing strands, and localizes competitive hybridization events to a contiguous strand of competing and switching strands in a strand-displacement mechanism-based switch, thereby improving the kinetics of strand-displacement. The improved regulatory systems have many uses in various biological systems, including gene expression control or ligand-concentration sensing.

15 Claims, 30 Drawing Sheets

(56) References Cited

U.S. PATENT DOCUMENTS

| | | | |
|---|---|---|---|
| 5,525,719 | A | 6/1996 | Srivastava et al. |
| 5,527,528 | A | 6/1996 | Allen et al. |
| 5,534,259 | A | 7/1996 | Zalipsky et al. |
| 5,543,152 | A | 8/1996 | Webb et al. |
| 5,543,158 | A | 8/1996 | Gref et al. |
| 5,547,932 | A | 8/1996 | Curiel et al. |
| 5,556,948 | A | 9/1996 | Tagawa et al. |
| 5,580,575 | A | 12/1996 | Unger et al. |
| 5,582,981 | A | 12/1996 | Toole et al. |
| 5,583,020 | A | 12/1996 | Sullivan |
| 5,591,721 | A | 1/1997 | Agrawal et al. |
| 5,595,756 | A | 1/1997 | Bally et al. |
| 5,736,392 | A | 4/1998 | Hawley-Nelson et al. |
| 5,756,291 | A | 5/1998 | Griffin et al. |
| 5,767,099 | A | 6/1998 | Harris et al. |
| 5,777,153 | A | 7/1998 | Lin et al. |
| 5,780,053 | A | 7/1998 | Ashley et al. |
| 5,830,430 | A | 11/1998 | Unger et al. |
| 5,830,653 | A | 11/1998 | Froehler et al. |
| 5,851,548 | A | 12/1998 | Dattagupta et al. |
| 5,855,910 | A | 1/1999 | Ashley et al. |
| 6,458,559 | B1 | 10/2002 | Shi et al. |
| 6,706,474 | B1 | 3/2004 | Lu et al. |
| 2002/0106648 | A1 | 8/2002 | Lizardi et al. |
| 2002/0150996 | A1 | 10/2002 | Nilsen-Hamilton |
| 2002/0166132 | A1 | 11/2002 | Scherman et al. |
| 2003/0105051 | A1 | 6/2003 | McSwiggen |
| 2003/0124595 | A1 | 7/2003 | Lizardi |
| 2003/0157030 | A1 | 8/2003 | Davis et al. |
| 2004/0063654 | A1 | 4/2004 | Davis et al. |
| 2004/0072785 | A1 | 4/2004 | Wolff et al. |
| 2004/0086884 | A1 | 5/2004 | Beach et al. |
| 2004/0162235 | A1 | 8/2004 | Trubetskoy et al. |
| 2004/0204377 | A1 | 10/2004 | Rana |
| 2005/0003362 | A1 | 1/2005 | Krylov et al. |
| 2005/0026286 | A1 | 2/2005 | Chi et al. |
| 2005/0037496 | A1 | 2/2005 | Rozema et al. |
| 2005/0042227 | A1 | 2/2005 | Zankel et al. |
| 2005/0048647 | A1 | 3/2005 | Taira et al. |
| 2005/0064595 | A1 | 3/2005 | MacLachlan et al. |
| 2005/0256071 | A1 | 11/2005 | Davis |
| 2005/0265957 | A1 | 12/2005 | Monahan et al. |
| 2006/0008910 | A1 | 1/2006 | MacLachlan et al. |
| 2006/0088864 | A1 | 4/2006 | Smolke et al. |
| 2006/0105975 | A1 | 5/2006 | Pendergrast et al. |
| 2006/0121510 | A1 | 6/2006 | Breaker et al. |
| 2006/0172925 | A1 | 8/2006 | Gorenstein et al. |
| 2006/0178327 | A1 | 8/2006 | Yeung |
| 2006/0240093 | A1 | 10/2006 | MacLachlan et al. |
| 2007/0077571 | A1 | 4/2007 | Ellington et al. |
| 2007/0083947 | A1 | 4/2007 | Huang et al. |
| 2007/0130653 | A1* | 6/2007 | Baulcombe et al. ......... 800/279 |
| 2007/0231392 | A1 | 10/2007 | Wagner et al. |
| 2008/0038296 | A1 | 2/2008 | Brahmbhatt et al. |
| 2008/0107694 | A1 | 5/2008 | Trogden et al. |
| 2008/0112916 | A1 | 5/2008 | Wagner et al. |
| 2008/0152661 | A1 | 6/2008 | Rozema et al. |
| 2009/0082217 | A1 | 3/2009 | Smolke et al. |
| 2009/0098561 | A1 | 4/2009 | Smolke et al. |
| 2009/0234109 | A1 | 9/2009 | Han et al. |
| 2010/0226901 | A1 | 9/2010 | Smolke et al. |
| 2010/0255545 | A1 | 10/2010 | Smolke et al. |
| 2011/0002892 | A1 | 1/2011 | Galloway et al. |

FOREIGN PATENT DOCUMENTS

| | | |
|---|---|---|
| WO | WO-88/09810 A1 | 12/1988 |
| WO | WO-89/10134 A1 | 11/1989 |
| WO | WO-90/11364 A1 | 10/1990 |
| WO | WO-90/14074 A1 | 11/1990 |
| WO | WO-91/16024 A1 | 10/1991 |
| WO | WO-91/17424 A1 | 11/1991 |
| WO | WO-92/03568 A1 | 3/1992 |
| WO | WO-97/42317 A1 | 11/1997 |
| WO | WO-98/13526 A1 | 4/1998 |
| WO | WO-99/04800 A1 | 2/1999 |
| WO | WO-99/27133 A1 | 6/1999 |
| WO | WO-99/54506 A1 | 10/1999 |
| WO | WO-00/20040 A1 | 4/2000 |
| WO | WO-2004/033653 A2 | 4/2004 |
| WO | WO-2004/048545 A2 | 6/2004 |
| WO | WO-2004/065601 A2 | 8/2004 |
| WO | WO-2005/001039 A2 | 1/2005 |
| WO | WO-2005/111238 A2 | 11/2005 |
| WO | WO-2006/086669 A2 | 8/2006 |
| WO | WO-2007/089607 A2 | 8/2007 |
| WO | WO-2008/036825 A2 | 3/2008 |
| WO | WO-2008/058291 A2 | 5/2008 |

OTHER PUBLICATIONS

Al-Douahji et al., "The cyclin kinase inhibitor p21WAF1/C1P1 is required for glomerular hypertrophy in experimental diabetic nephropathy," *Kidney Int.*, 56:1691-1699 (1999).

Amarzguioui et al., "Tolerance for mutations and chemical modifications in a siRNA," *Nucleic Acid Research*, 31: 589-595 (2003).

An et al., "Artificial control of gene expression in mammalian cells by modulating RNA interference through aptamer-small molecule interaction," *RNA*, 12(5):710-716 (2006).

Anderson et al., "Environmental signal integration by a modular and gate," *Mol. Syst. Biol.*, 3:133 (2007).

Araki et al., "Allosteric regulation of a ribozyme activity through ligand-induced conformational change," *Nucleic Acids Research*, 26(14): 3379-3384 (1998).

Baker et al., "Engineering life: building a Fab for biology," *Scientific American*, 294:44-51 (2006).

Banerjee and Slack, "Control of developmental timing by small temporal RNAs: a paradigm for RNA-mediated reaulation of gene expression," *Bioessays*, 24:119-129 (2002).

Barrick et al., "New RNA motifs suggest an expanded scope for riboswitches in bacterial genetic control," *Proc. Natl. Acad. Sci. USA*, 101:6421-6426 (2004).

Bartel, "MicroRNAs: genomics, biogenesis, mechanism, and function," *Cell*, 116:281-297 (2004).

Bartlett and Davis, "Insights into the kinetics of siRNA-mediated gene silencing from live-cell and live-animal bioluminescent imaging," *Nucleic Acids Res.*, 34:322-333 (2006).

Basu et al., "Spatiotemporal control of gene expression with pulse-generating networks," *Proc. Natl. Acad. Sci. USA*, 101:6355-6360 (2004).

Batzer et al., "Enhanced evolutionary PCR using oligonucleotides with inosine at the 3'-terminus," *Nucleic Acids Res.*, 19:5081 (1991).

Bauer et al., "Prevention of interferon-stimulated gene expression using microRNA-designed hairpins," *Gene Ther.*, 16:142-147 (2009).

Bauer and Suess, "Engineered riboswitches as novel tools in molecular biology," *J. Biotech.*, 124(1):4-11 (2006).

Baulcombe, "Diced defence," *Nature*, 409(6818):295-296 (2001).

Bayer and Smolke, "Programmable ligand-controlled riboregulators of eukaryotic gene expression," *Nat. Biotechnol.*, 23:337-343 (2005).

Bayer et al., "Synthetic control of a fitness tradeoff in yeast nitrogen metabolism," *J. Biol. Eng.* 3:1 (2009).

Been and Cech, "One binding site determines sequence specificity of Tetrahymena pre-rRNA self-splicing, trans-splicing, and RNA enzyme activity," *Cell*, 47:207 216 (1986).

Beisel and Smolke, "Design principles for riboswitch function," *PLoS Comp. Biol.*, 5:e1000363 (2009).

Beisel et al., "Model-Guided Design of Ligand-Regulated RNAi for Programmable Control of Gene Expression," *Molecular Systems Biology*, 4:224 (2008).

Benenson et al., "An autonomous molecular computer for logical control of gene expression," *Nature*, 429:423-429 (2004).

Benenson, "Small hairpin RNA as a small molecule sensor," *Mol. Sys. Biol.*, 4:227 (2008).

Benoist et al., "In vivo sequence requirements of the SV40 early promotor region," *Nature*, 290:304-310 (1981).

Berens et al., "A tetracycline-binding RNA aptamer," *Bioorg. Med. Chem.*, 9:2549-2556 (2001).

(56) References Cited

OTHER PUBLICATIONS

Berens and Suess, "Synthetic riboregulators—an alternative means to control gene expression," *Gene Therapy and Molecular Biology*, 9:417-422 (2005).
Berezovski et al., "Nonequilibrium Capillary Electrophoresis of Equilibrium Mixtures: A Universal Tool for Development of Aptamers," *J. Am. Chem. Soc.*, 127:3165-3171 (2005).
Berge et al., "Pharmaceutical Salts," *J. Pharm Sci.*, 66:1-19 (1977).
Biesecker et al, "Derivation of RNA aptamer inhibitors of human complement C5," *Immunopharmacology*, 42(1-3):219-230 (1999).
Birikh et al., "The structure, function and application of the hammerhead ribozyme," *Eur. J. Biochem.*, 245:1-16 (1997).
Blind et al., Cytoplasmic RNA modulators of an inside-out signal-transduction cascade, *Proc. Natl. Acad. Sci. USA*, 96:3606-3610 (1999).
Blount and Uhlenbeck, "The structure-function dilemma of the hammerhead ribozyme," *Annu. Rev. Biophys. Biomol .Struct.*, 34:415-440 (2005).
Boiziau et al., "DNA Aptamers Selected Against the HIV-1 trans-Activation Responsive RNA Element Form RNA-DNA Kissing Complexes," *J. Biol. Chem.*, 274(18):12730-12737 (1999).
Boiziau et al., "Identification of Aptamers Against the DNA Template for In Vitro Transcription of the HIV-1 TAR Element," *Antisense Nucleic Acid Drug Dev.*, 7(4):369-380 (1997).
Boudreau et al., "Artificial microRNAs as siRNA shuttles: improved safety as compared to shRNAs in vitro and in vivo," *Mol. Ther.*, 17(1):169-175 (2009).
Breaker, "Complex riboswitches," *Science*, 319:1795-1797 (2008).
Breaker, "Engineered allosteric ribozymes as biosensor components," *Curr. Opin. Biotechnol.*, 13:31-39 (2002).
Brennecke and Cohen, "Towards a complete description of the microRNA complement of animal genomes," *Genome Biol.*, 4:228. 1-228.3 (2003).
Brinster et al., "Regulation of metallothionein-thymidine kinase fusion plasmids injected into mouse eggs," *Nature*, 296:39-42 (1982).
Brockstedt et al., "In vitro evolution of RNA aptamers recognizing carcinogenic aromatic amines," *Biochem. Biophys. Res. Commun.*, 313(4):1004-1008 (2004).
Brown et al., "Endogenous microRNA can be broadly exploited to regulate transgene expression according to tissue, lineage and differentiation state," *Nat. Biotechnol.*, 25:1457-1467 (2007).
Brummelkamp et al., "A system for stable expression of short interfering RNAs in mammalian cells," *Science*, 296:550-553 (2002).
Bunka and Stockley, "Aptamers come of age—at last," *Nat. Rev. Microbiol.*, 4:588-596 (2006).
Burke and Greathouse, "Low-magnesium, trans-cleavage activity by type III, tertiary stabilized hammerhead ribozymes with stem 1 discontinuities," *BMC Biochem.*, 6:14 (2005).
Burke et al., "RNA aptamers to the adenosine moiety of S-adenosyl methionine: structural inferences from variations on a theme and the reproducibility of SELEX," *Nucleic Acids Research*, 25(10):2020-2024 (1997).
Buskirk et al., "Engineering a Ligand-Dependent RNA Transcriptional Activator," *Chemistry & Biology*, 11:1157-1163 (2004).
Buskirk et al., "In Vivo Evolution of an RNA-Based Transcriptional Activator," *Chemistry & Biology*, 10:533-540 (2003).
Cai et al., "Human microRNAs are processed from capped, polyadenylated transcripts that can also function as mRNAs," *RNA*, 10:1957-1966 (2004).
Calin et al., "MiR-15a and miR-16-1 cluster functions in human leukemia," *Proc. Natl. Acad. Sci. USA*, 105:5166-5171 (2008).
Canny et al., "Fast cleavage kinetics of a natural hammerhead ribozyme," *J. Am. Chem. Soc.*, 126(35):10848-10849 (2004).
Caplen et al., "Specific inhibition of gene expression by small double-stranded RNAs in invertebrate and vertebrate systems," *Proc. Natl. Acad. Sci. USA*, 98:9742-9747 (2001).
Caponigro et al., "A small segment of the MATα1 transcript promotes mRNA decay in *Saccharomyces cerevisiae*: a stimulatory role for rare codons," *Mol. Cell Biol.*, 13:5141-5148 (1993).

Carmell and Hannon, "RNase III enzymes and the initiation of gene silencing," *Nature Structural & Molecular Biology*, 11:214-218 (2004).
Chen et al., "Genetic control of mammalian T-cell proliferation with synthetic RNA regulatory systems," *Proc. Natl. Acad. Sci. USA.*, 107:8531-8536 (2010).
Chen et al., "Synthesis of oligodeoxyribonucleotide N3'-> P5' phosphoramidates," *Nucleic Acids Res.*, 23:2661-2668 (1995).
Chiu and Rana, "RNAi in Human Cells: Basic Structural and Functional Features of Small Interfering RNA," *Mol. Cell*, 10:549-561 (2002).
Chiu and Rana, "siRNA function in RNAi: A chemical modification analysis," *RNA*, 9:1034-1048 (2003).
Cox et al., "Automated selection of aptamers against protein targets translated in vitro: from gene to aptamer," *Nucleic Acids Res.*, 30:e108 (2002).
Cox et al., "Programming gene expression with combinatorial promoters," *Mol. Syst. Biol.*, 3:145 (2007).
Croft et al., "Is prokaryotic complexity limited by accelerated growth in regulatory overhead?" *Genome Biology*, 5:P2 (2003).
Culler et al., "Functional selection and systematic analysis of intronic splicing elements identifies active sequence motifs and associated splicing factors," *Nucl. Acids Res.*, 38:5152-5165 (2010).
Dambach, D.M., "Potential adverse effects associated with inhibition of p38α/β MAP kinases," *Curr. Top. Med. Chem.*, 5 (10):929-939 (2005).
Daniels, "A tenascin-C aptamer identified by tumor cell SELEX: Systematic evolution of ligands by exponential enrichment," *PNAS*, 100(26):15416-15421 (2003).
Danilova et al., "RNAKinetics: a web server that models secondary structure kinetics of an elongating RNA," *J. Bioinform. Comput. Biol.*, 4:589-596 (2006).
Davidson and Ellington, "Synthetic RNA circuits," *Nature Chemical Biology*, 3(1):23-28 (2007).
De La Pena et al., "Peripheral regions of natural hammerhead ribozymes greatly increase their self-cleavage activity," *Embo. J.*, 22(20):5561-5570 (2003).
Deans et al., "A Tunable Genetic Switch Based on RNAi and Repressor Proteins for Regulating Gene Expression in Mammalian Cells," *Cell*, 130:363-372 (2007).
Desai and Gallivan, "Genetic screens and selections for small molecules based on a synthetic riboswitch that activates protein translation," *J. Am. Chem. Soc.*,126:13247-13254 (2004).
Dirks and Pierce, "Triggered amplification by hybridization chain reaction," *Proc. Natl. Acad. Sci. USA*, 101:15275-15278 (2004).
Drabovich et al., "Selection of Smart Aptamers by Equilibrium Capillary Electrophoresis of Eauilibrium Mixtures (ECEEM)," *J. Am. Chem. Soc.*, 127:11224-11225 (2005).
Dragun et al., "ICAM-1 antisense oligodesoxynucleotides prevent reperfusion injury and enhance immediate graft function in renal transplantation," *Kidney Int.*, 54:590-602 (1998).
Dragun et al., "Inhibition of intercellular adhesion molecule-1 with antisense deoxynucleotides prolonos renal isograft survival in the rat," *Kidney Int.*, 54:2113-2122 (1998).
Ducongé and Toulmé, "In vitro selection identifies key determinants for loop-loop interactions: RNA aptamers selective for the TAR RNA element of HIV-1," *RNA*, 5:1605-1614 (1999).
Dueber et al., "Engineering synthetic signaling proteins with ultrasensitive input-output control," *Nat. Biotechnol.*, 25:660-662 (2007).
Egholm et al., "PNA hybridizes to complementary oligonucleotides obeying the Watson-Crick hydrogen-bonding rules," *Nature*, 365:566-568 (1993).
Elbashir et al., "Duplexes of 21-nucleotide RNAs mediate RNA interference in cultured mammalian cells," *Nature*, 411:494-498 (2001).
Elion, "The Ste5p scaffold," *J. Cell Sci.*, 114(22):3967-3978 (2001).
Ellington and Szostak, "In vitro selection of RNA molecules that bind specific ligands," *Nature*, 346:818-822 (1990).
Elowitz and Leibler, "A synthetic oscillatory network of transcriptional regulators," *Nature*, 403:335-338 (2000).
Endy, "Foundations for engineering biology," *Nature*, 438:449-453 (2005).

(56) References Cited

OTHER PUBLICATIONS

Eulberg et al., "Development of an automated in vitro selection protocol to obtain RNA-based aptamers: identification of a biostable substance P antagonist," *Nucleic Acids Res.*, 33(4):e45 (2005).
Famulok, "Bringing Picomolar Protein Detection Into Proximity," *Nature Biotechnology*, 20:448-449 (2002).
Famulok, "Oligonucleotide aptamers that recognize small molecules," *Curr. Opin. Struct. Biol.*, 9:324-329 (1999).
Fedor and Williamson, "The catalytic diversity of RNAs," *Nat. Rev. Mol. Cell Biol.*, 6:399-412 (2005).
Flinders et al., "Recognition of planar and nonplanar ligands in the malachite green-rna aptamer complex," *Chembiochem.*, 5(I):62-72 (2004).
Flotte, "Size does matter: overcoming the adeno-associated virus packaging limit," *Respir. Res.*, 1:16-18 (2000).
Fredriksson et al., "Protein Detection Using Proximity-Dependent DNA Litagation Assays," *Nature Biotechnology*, 20:473-477 (2002).
Friedman et al., "Most mammalian mRNAs are conserved targets of microRNAs," *Genome Res.*, 19: 92-105 (2009).
Fukusaki et al., "DNA aptamers that bind to chitin," *Bioorg. Med. Chem. Lett.*, 10(5):423-425 (2000).
Gardner et al., "Inferring genetic networks and identifying compound mode of action via expression profiling," *Science*, 301:102-105 (2003).
Gautier et al., "α-DNA. IV: α-anomeric and β-anomeric tetrathymidylates covalently linked to intercalating oxazolopyridocarbazole. Synthesis, physicochemical properties and poly (rA) Binding," *Nucleic Acids Res.*, 15:6625-6641 (1987).
Gebhardt, "RNA-aptamers to s-adenosylhomocysteine: kinetic properties, divalent cation dependency, and comparison with anti-s-adenosylhomocysteine antibody," *Biochemistry*, 39(24):7255-7265 (2000).
Geiger et al., "RNA aptamers that bind L-arginine with submicromolar dissociation constants and high enantioselectivity," *Nucleic Acids Res.*, 24(6):1029-1036 (2000).
Gil and Esteban, "Induction of apoptosis by the dsRNA-dependent protein kinase (PKR): mechanism of action," *Apoptosis*, 5:107-114 (2000).
Gilbert et al. "RNA Aptamers that Specifically Bind to a K Ras-Derived Farnesylated Peptide," *Bioorg. Med. Chem.*, 5(6):1115-1122 (1997).
Good, "Diverse antisense mechanisms and applications," *Cell Mol. Life Sci.*, 60:823-824 (2003).
Good, "Translation repression by antisense sequences," *Cell Mol. Life Sci.*, 60:854-861 (2003).
Gopinath et al., "An efficient RNA aptamer against human influenza b virus hemagglutinin," *J. Biochem.* (Tokyo), 139(5):837-846 (2006).
Gossen and Bujard, "Tight control of gene expression in mammalian cells by tetracycline-responsive promoters," *Proc. Natl. Acad. Sci. USA*, 89:5547-5551 (1992).
Gouda et al., "Free energy calculations for theophylline binding to an RNA aptamer: Comparison of MM-PBSA and thermodynamic integration methods," *Biopolymers*, 68:16-34 (2003).
Grassi et al., "Cleavage of collagen RNA transcripts by hammerhead ribozymes in vitro is mutation-specific and shows competitive binding effects," *Nucleic Acids Res.*, 25(17):3451-3458 (1997).
Grate and Wilson, "Inducible regulation of the *S. cerevisiae* cell cycle mediated by an RNA aptamer-ligand complex," *Bioorg. Med. Chem.*, 9:2565-2570 (2001).
Gregory et al., "Human RISC couples microRNA biogenesis and posttranscriptional gene silencing," *Cell*, 123:631-640 (2005).
Gregory et al., "The Microprocessor complex mediates the genesis of microRNAs," *Nature*, 432:235-240 (2004).
Grieger and Samulski, "Packaging capacity of adeno-associated virus serotypes: impact of larger genomes on infectivity and postentry steps," *J. Virol.*, 79:9933-9944 (2005).
Griffiths-Jones et al., "miRBase: microRNA sequences, targets and gene nomenclature," *Nucleic Acids Res.*, 34:D140-D144 (2006).
Griffiths-Jones, "The microRNA Registry," *Nucleic Acids Res.*, 32:D109-D111 (2004).
Grimm et al., "Fatality in mice due to oversaturation of cellular microRNNshort hairpin RNA pathways," *Nature*, 441:537-541 (2006).
Grundy and Henkin, "From ribosome to riboswitch: control of gene expression in bacteria by RNA structural rearrangements," *Crit. Rev. Biochem. Mol. Biol.*, 41:329-338 (2006).
Guet et al., "Combinatorial synthesis of genetic networks," *Science*, 296:1466-1470 (2002).
Guil and Cáceres, "The multifunctional RNA-binding protein hnRNP AI is required for processing of miR-18a," *Nat. Struct. Mol. Biol.*, 14:591-596 (2007).
Hall et al., "Computational selection of nucleic acid biosensors via a slip structure model," *Biosens. Bioelectron.*, 22:1939-1947 (2007).
Haller et al., "Antisense oligonucleotides for ICAM-1 attenuate reperfusion injury and renal failure in the rat," *Kidney Int.*, 50:473-480 (1996).
Haller and Sarnow, "In vitro selection of a 7-methyl-guanosine binding RNA that inhibits translation of capped mRNA molecules," *Proc. Natl. Acad. Sci. USA*, 94:8521-8526 (1997).
Hamada et al., "Effects on RNA Interference in Gene Expression (RNAi) in Cultured Mammalian Cells of Mismatches and the Introduction of Chemical Modifications at the 3'-Ends of siRNAs," *Antisense Nucleic Acid Drug Dev.*, 12(5):301-309 (2002).
Hamm et al., "Anti-idiotype RNA selected with an anti-nuclear export signal antibody is actively transported in oocytes and inhibits Rev- and cap-dependent RNA export," *Proc. Natl. Acad. Sci. USA*, 94:12839-12844 (1997).
Hammann et al., "Dissection of the ion-induced folding of the hammerhead ribozyme using 19F NMR," *Proc. Natl. Acad. Sci. USA*, 98(10):5503-5508 (2001).
Hammond et al., "Argonaute2, a Link Between Genetic and Biochemical Analyses of RNAi," *Science*, 293(5532):1146-1150 (2001).
Han et al., "Molecular basis for the recognition of primary microRNAs by the Drosha-DGCR8 complex," *Cell*, 125:887-901 (2006).
Han et al., "Posttranscriptional crossregulation between Drosha and DGCR8," *Cell*, 136:75-84 (2009).
Han et al., "The Drosha-DGCR8 complex in primary microRNA processing," *Genes Dev.*, 18:3016-3027 (2004).
Hanahan and Weinberg, "The Hallmarks of Cancer," *Cell*, 100(1):57-70 (2000).
Hanson et al., "Tetracycline-aptamer-mediated translational regulation in yeast," *Mol. Microbiol.*, 49(6):1627-1637 (2003).
Harborth et al., "Sequence, Chemical, and Structural Variation of Small Interfering RNAs and Short Hairpin RNAs and the Effect on Mammalian Gene Silencing," *Antisense and Nucleic Acid Drug Dev.*, 13(2):83-105 (2003).
Haseloff and Gerlach, "Simple RNA enzymes with new and highly specific endoribonuclease activities," *Nature*, 334:585-591 (1988).
Hawkins and Smolke, "Production of benzylisoquinoline alkaloids in *Saccharomyces cerevisiae*," *Nat. Chem. Biol.*, 4:564-573 (2008).
Hawkins and Smolke, "The regulatory roles of the galactose permease and kinase in the induction response of the GAL network in *Saccharomyces cerevisiae*," *J. Biol. Chem.*, 281:13485-13492 (2006).
Hebert et al., "Loss of microRNA cluster miR-29a-b-1 in sporadic Alzheimer's disease correlates with increased BACE1-13-secretase expression," *Proc. Natl. Acad. Sci. USA*, 105:6415-6420 (2008).
Heidenreich et al., "RNase H-independent antisense activity of oligonucleotide N3' -> P5' phosphoramidates," *Nucleic Acids Res.*, 25(4):776-780 (1997).
Hermann and Patel, "Adaptive Recognition by Nucleic Acid Aptamers," *Science*, 287:820-825 (2000).
Hesselberth et al., "In Vitro Selection of RNA Molecules That Inhibit the Activity of Ricin A-chain," *J. Biol. Chem.*, 275(7):4937-4942 (2000).
Hesselberth et al., "Simultaneous Detection of Diverse Analytes with an Aptazyme Ligase Array," *Analytical Biochemistry*, 312:106-112 (2003).
Hicke et al., "Tenascin-C Aptamers Are Generated Using Tumor Cells and Purified Protein," *J. Biol. Chem.*, 276(52):48644-48654 (2001).

(56) References Cited

OTHER PUBLICATIONS

Hirao et al., "RNA Aptamers That Bind to and Inhibit the Ribosome-inactivating Protein, Pepocin," *J. Biol. Chem.*, 275(7):4943-4948 (2000).
Hirschbein and Fearon, "$^{31}$P NMR spectroscopy in oligonucleotide research and development," *Antisense Nucleic. Acid Drug Dev.*, 7:55-61 (1997).
Hoff et al., "Fluorescence detection of a protein-bound 2Fe2S cluster," *ChemBioChem.*, 10:667-670 (2009).
Hoff et al., "In vivo fluorescent detection of Fe-S clusters coordinated by human GRX2," *Chem. Biol.*, 16:1299-1308 (2009).
Hooshangi et al., "Ultrasensitivity and noise propagation in a synthetic transcriptional cascade," *Proc. Natl. Acad. Sci. USA*, 102:3581-3586 (2005).
Hornung et al., "In vitro Selected RNA Molecules that Bind to Elongation Factor Tu," *Biochemistry*, 37:7260-7267 (1998).
Huang and Ferrell, "Ultrasensitivity in the mitogen-activated protein kinase cascade," *Proc. Natl. Acad. Sci. USA*, 93:10078-10083 (1996).
Huizenga and Szostak, "A DNA aptamer that binds adenosine and ATP," *Biochemistry*. 34:656-665 (1995).
Hutvagner et al., "Sequence-specific inhibition of small RNA function," *PLoS Biol.*, 2: E98 (2004).
Hwang et al., "A Hexanucleotide Element Directs MicroRNA Nuclear Import," *Science*, 315:97-100 (2007).
Inoue et al., "Sequence-dependent hydrolysis of RNA using modified oligonucleotide splints and RNase H," *FEBS Lett.*, 215:327-330 (1987).
Inoue et al., "Synthesis and hybridization studies on two complementary nona(2'-O-methyl) ribonucleotides," *Nucleic Acids Res.*, 15:6131-6148 (1987).
International Search Report in International Application No. PCT/US07/84364 (Aug. 19, 2008).
Isaacs et al., "Engineered riboregulators enable post-transcriptional control of gene expression," *Nat. Biotechnol.*, 22:841-847 (2004).
Isaacs and Collins, "Plug and play with RNA," *Nat. Biotech.*, 23:306-307 (2005).
Isaacs et al., "RNA synthetic biology," *Nature Biotechnology*, 24(5):545-554 (2006).
Javaherian et al., "Selection of aptamers for a protein target in cell lysate and their application to protein purification," *Nucleic Acids Res.*, 37(8):e62 (2009).
Jenison et al., "High-resolution molecular discrimination by RNA," *Science*, 263:1425-1429 (1994).
Jeong et al., "In vitro selection of the RNA aptamer against the sialyl lewis x and its inhibition of the cell adhesion," *Biochem. Biophys. Res. Comm.*, 281(I):237-243 (2001).
Jhaveri et al., "In vitro selection of signaling aptamers," *Nat. Biotechnol.*, 18:1293-1297 (2000).
Jose et al., "Cooperative binding of effectors by an allosteric ribozyme," *Nucleic Acids Res.*, 29:1631-1637 (2001).
Kato et al., "In vitro selection of DNA aptamers which bind to cholic acid," *Biochim. Biophys. Acta,* 1493(1-2):12-18 (2000).
Keasling, "From yeast to alkaloids." *Nat. Chem. Biol.*, 4: 524-525 (2008).
Kedde et al., "RNA-binding protein Dnd1 inhibits microRNA access to target mRNA," *Cell*, 131:1273-1286 (2007).
Kertsburg and Soukup, "A versatile communication module for controlling RNA folding and catalysis," *Nucleic Acids Res.*, 30:4599-4606 (2002).
Ketting et al., "Dicer functions in RNA interference and in synthesis of small RNA involved in developmental timing in *C. elegans*," *Genes Dev.*, 15:2654-2659 (2001).
Khosla and Keasling, "Metabolic engineering for drug discovery and development," *Nat. Rev. Drug Discov.*, 2:1019-1025 (2003).
Khvorova et al., "Sequence elements outside the hammerhead ribozyme catalytic core enable intracellular activity," *Nat. Struct. Biol.*, 10:708-872 (2003).
Kiga et al., "An RNA aptamer to the xanthine-guanine base with a distinctive mode of purine recognition," *Nucleic Acids Res.*, 26(7):1755-1760 (1998).

Kim et al., "An artificial riboswitch for controlling pre-mRNA splicing," *RNA*, 11:1667-1677 (2005).
Kim et al., "Synthetic dsRNA Dicer substrates enhance RNAi potency and efficacy," *Nature Biotech.*, 23:222-226 (2008).
Kim, "Small RNAs: classification, biogenesis, and function," *Mol. Cells*, 19:1-15 (2005).
Kimoto et al., "Anti-(Raf-1) RNA aptamers that inhibit Ras-induced Raf-1 activation," *Eur. J. Biochem.*, 269(2):697-704 (2002).
Kimoto et al., "RNA aptamers that specifically bind to the Ras-binding domain of Raf-1," *FEBS Lett.*, 441(2):322-326 (1998).
Kipshidze et al., "Intramural coronary delivery of advanced antisense oligonucleotides reduces neointimal formation in the porcine stent restenosis model," *J. Am. Coll. Cardiol.*, 39:1686-1691 (2002).
Kipshidze et al., "Local delivery of c-myc neutrally charged antisense oligonucleotides with transport catheter inhibits myointimal hyperplasia and positively affects vascular remodeling in the rabbit balloon injury model," *Catheter CardiovascIntery*, 54:247-256 (2001).
Kobayashi et al., "Programmable cells: interfacing natural and engineered gene networks," *Proc. Natl. Acad. Sci. USA.*, 101:8414-8419 (2004).
Koch, "The metabolism of methylpurines by *Escherichia coli*. I. Tracer studies," *J. Biol. Chem.*, 219:181-188 (1956 ).
Koizumi et al., "Allosteric selection of ribozymes that respond to the second messengers cGMP and cAMP," *Nat. Struct. Biol.*, 6:1062-1071 (1999).
Koizumi et al., "Molecular recognition of cAMP by an RNA aptamer," *Biochemistry*, 39(30):8983-8992 (2000).
Kok et al., "Human TRBP and PACT directly interact with each other and associate with dicer to facilitate the production of small interfering RNA," *J. Biol. Chem.*, 282:17649-17657 (2007).
Kramer et al., "BioLogic gates enable logical transcription control in mammalian cells," *Biotechnol. Bioeng.*, 87:478-484 (2004).
Kramer et al., "Role for antisense RNA in regulating circadian clock function in *Neurospora crassa,"* *Nature*, 421:948-952 (2003).
Kraus et al., "Cutting Edge: Novel RNA Ligands Able to Bind CD4 Antigen and Inhibit CD41 T Lymphocyte Function," *J. Immunol.*, 160(II): 5209-5212 (1998).
Kutryk et al., "Local intracoronary administration of antisense oligonucleotide against c-myc for the prevention of in-stent restenosis: results of the randomized investigation by the Thoraxcenter of antisense DNA using local delivery and IVUS after coronary stenting (ITALICS) trial," *J. Am. Coll. Cardiol.*, 39:281-287 (2002).
Kuwabara et al., "Allosterically controllable maxizyme-mediated suppression of progression of leukemia in mice," *Biomacromolecules*, 2:1220-1228 (2001).
Kuwabara et al., "Allosterically controllable ribozymes with biosensor functions," *Curr. Opin. Chem. Biol.*, 4:669-677 (2000).
Kuwabara et al., "Allosterically controlled single-chained maxizymes with extremely high and soecific activity," *Biomacromolecules*, 2:788-799 (2001).
Lavorgna et al., "In search of antisense," *Trends Biochem. Sci.*, 29:88-94 (2004).
Lee et al., "Aptamer database," *Nucleic Acids Res.*, 32:D95-D100 (2004).
Lee and Kim, "In vitro and in vivo assays for the activity of Drosha complex," *Methods Enzymol.*, 427:89-106 (2007).
Lee et al., "MicroRNA maturation: stepwise processing and subcellular localization," *EMBO J.*, 21(17):4663-4670 (2002).
Lee et al., "The nuclear RNase III Drosha initiates microRNA processing," *Nature*, 425:415-419 (2003).
Lee et al., "The role of PACT in the RNA silencing pathway," *EMBO J.*, 25:522-532 (2006).
Legiewicz and Yarus, "A More Complex Isoleucine Aptamer with a Cognate Triplet," *J. Biol. Chem.*, 280(20):19815-19822 (2005).
Lemaitre et al., "Specific antiviral activity of a poly(L-lysine)-conjugated oligodeoxyribonucleotide sequence complementary to vesicular stomatitis virus N protein mRNA initiation site," *Proc. Natl. Acad. Sci. USA*, 84:648-652 (1987).
Lescoute and Westhof, "Topology of three-way junctions in folded RNAs," *RNA*, 12:83-93 (2006).

(56) References Cited

OTHER PUBLICATIONS

Letsinger et al., "Cholesteryl-conjugated oligonucleotides: synthesis, properties, and activity as inhibitors of replication of human immunodeficiency virus in cell culture," *Proc. Natl. Acad. Sci. USA*, 86:6553-6556 (1989).
Levine et al., "Quantitative Characteristics of Gene Regulation by Small RNA," *PLoS Biol.*, 5(e229):1998-2010 (2007).
Li and Breaker, "Kinetics of RNA Degradation by Specific Base Catalysis of Transesterification Involving the 2'-Hydroxyl Group," *J. Am. Chem. Soc.*, 121: 5364-5372 (1999).
Lilley, "The origins of RNA catalysis in ribozymes," *Trends Biochem. Sci.*, 28:495-501 (2003).
Liu et al., "RNA aptamers specific for bovine thrombin," *J. Mol. Recog.*, 16(1):23-27(2003).
Liu et al., "Soafenib blocks the RAF/MEK/ERK pathway, inhibits tumor angiogenesis, and induces tumor cell apoptosis in hepatocellular carcinoma model PLC/PRF/5," *Cancer Res.*, 66(24):11851-11858 (2006).
Long and Uhlenbeck, "Self-cleaving catalytic RNA," *Faseb J.*, 7(1):25-30 (1993).
Lorsch and Szostak, "In vitro selection of RNA aptamers specific for cyanocobalamin," *Biochemistry*, 33:973-982 (1994).
Lozupone et al., "Selection of the simplest RNA that binds isoleucine," *RNA*, 9(II): 1315-1322 (2003).
Lutz and Bujard, "Independent and tight regulation of transcriptional units in *Escherichia coli* via the LacR/O, the TetR/O and AraC/I1-12 regulatory elements," *Nucleic Acids Res.*, 25(6):1203-1210 (1997).
Luzi et al., "New Trends in Affinity Sensing: Aptamers for Ligand Binding," *Trends in Analytical Chemistry*, 22:810-818 (2003).
Lynch et al., "A high-throughput screen for synthetic riboswitches reveals mechanistic insights into their function," *Chem. Biol.*, 14:173-184 (2007).
MacRae et al., "Structural Basis for Double-Stranded RNA Processing by Dicer," *Science*, 311( 5758):195-198 (2006).
Malphettes and Fussenegger, "Impact of RNA interference on gene networks," *Metab. Eng.*, 8:672-683 (2006).
Mandal and Breaker, "Gene regulation by riboswitches," *Natl. Rev. Mol. Cell Biol.*, 5:451-463 (2004).
Mandal et al., "A glycine-dependent riboswitch that uses cooperative binding to control gene expression," *Science.*, 306:275-279 (2004).
Mandal et al., "Adenine riboswitches and gene activation by disruption of a transcription terminator," *Nat. Struct. Mol. Biol.*, 11:29-35 (2004).
Mannironi et al., "In vitro selection of dopamine RNA ligands," *Biochemistry*, 36:9726-9734 (1997).
Marschall et al., "Inhibition of gene expression with ribozymes," *Cell Mol. Neurobiol.*, 14(5):523-538 (1994).
Martin et al., "Redesigning cells for the production of complex organic molecules," *ASM News*, 68:336-343 (2002).
Mateus and Avery, "Destabilized green fluorescent protein for monitoring dynamic changes in yeast gene expression with flow cytometry," *Yeast*, 16:1313-1323 (2000).
Mathews et al., "Incorporating chemical modification constraints into a dynamic programming algorithm for prediction of RNA secondary structure," *Proc. Natl. Acad. Sci. USA*, 101:72877292 (2004).
Mathews and Turner, "Prediction of RNA secondary structure by free energy minimization," *Curr. Opin. Struct. Biol.*, 16:270-278 (2006).
Matranga et al., "Passenger-strand cleavage facilitates assembly of siRNA into Ag02—containing RNAi enzyme complexes," *Cell*, 123:607-620 (2005).
McBride et al., "Artificial miRNAs mitigate shRNA-mediated toxicity in the brain: Implications for the therapeutic development of RNAi," *PNAS*, 105:5868 (2008).
McCaffrey et al., "RNA interference in adult mice," *Nature*, 418:38-39 (2002).
McCormick, "Signalling Networks that Cause Cancer," *Trends Cell Biol.*, 9(12):M53-M56 (1999).
McManus et al., "Gene silencing using micro-RNA desianed hairpins," *RNA*, 8:842-850 (2002).
Meister et al., "Sequence-specific inhibition of microRNA- and siRNA-induced RNA silencing," *RNA*, 10:544-550 (2004).
Mendonsa and Bowser, "In Vitro Evolution of Functional DNA Using Capillary Electrophoresis," *J. Am. Chem. Soc.*, 126:20-21 (2004).
Mendonsa and Bowser, "In Vitro Selection of Aptamers with Affinity for Neuropeptide Y Using D Capillary Electrophoresis," *J. Am. Chem. Soc.*, 127:9382-9383 (2005).
Mendonsa and Bowser, "In Vitro Selection of High-Affinity DNA Ligands for Human IgE Using Capillary Electrophoresis," *Anal. Chem.*, 76:5387-5392 (2004).
Misono et al., "Selection of RNA aptamers against human influenza virus hemagglutinin using surface plasmon resonance," *Anal. Biochem.*, 342(2):312-317 (2005).
Muller et al., "Thermodynamic characterization of an engineered tetracycline-binding riboswitch," *Nucleic Acids Res.*, 34(9):2607-2617 (2006).
Nagai et al., "A variant of yellow fluorescent protein with fast and efficient maturation for cellbiological applications," *Nat. Biotechnol.*, 20:87-90 (2002).
Ng and Abelson, "Isolation and sequence of the gene for actin in *Saccharomyces cerevisiae*," *Proc. Natl. Acad. Sci. USA*, 77(7):3912-3916 (1980).
Nickols and Dervan,"Suppression of androgen receptor-mediated gene expression by a sequence-specific DNA-binding polyamide," *Proc. Natl.Acad. Sci. USA*, 104:10418-10423 (2007).
Nishiwaki et al., "Structure of the yeast HIS5 gene responsive to general control of amino acid biosynthesis," *Mol. Gen. Genet.*, 208:159-167 (1987).
Novina and Sharp, "The RNAi revolution," *Nature*, 430(6996):161-164 (2004).
Nutiu and Li, "Structure-Switching Signaling Aptamers," *J. Am. Chem. Soc.*, 125:4771-4778 (2003).
Nutiu and Li, "Structure-Switching Signaling Aptamers: Transducing Molecular Recognition into Fluorescence Signaling," *Chem. Eur. J.*, 10:1868-1876 (2004).
Ogawa and Maeda, "An artificial aptazyme-based riboswitch and its cascading system in *E. coli*," *ChemBioChem.*, 9:206-209 (2008).
Ogawa et al., "Purification, Characterization, and Gene Cloning of Purine Nucleosidase from *Ochrobactrum anthropi*," *Appl. Environ. Microbiol.*, 67(1 ):1783-1787 (2001).
Ohrt et al., "Fluorescence correlation spectroscopy and fluorescence cross-correlation spectroscopy reveal the cytoplasmic origination of loaded nuclear RISC in vivo in human cells," *Nucleic Acids Res.*, 36(20): 6439-6449 (2008).
Ohtsuka et al., "An alternative approach to deoxyoligonucleotides as hybridization probes by insertion of deoxyinosine at ambiauous codon positions," *J. Biol. Chem.*, 260:2605-2608 (1985).
Osborne and Ellington, "Nucleic Acid Selection and the Challenge of Combinatorial Chemistry," *Chem. Rev.*, 97:349-370 (1997).
Paddison et al., "Short hairpin RNAs (shRNAs) induce sequence-specific silencing in mammalian cells," *Genes Dev.*, 16:948-958 (2002).
Paddison et al., "Stable suppression of gene expression by RNAi in mammalian cells," *Proc. Natl. Acad. Sci. USA*, 99:1443-1448 (2002).
Pan et al., "A self-processing ribozyme cassette: utility against human papillomavirus 11 E6/E7 mRNA and hepatitis B virus," *Mol. Ther.*, 9(4):596-606 (2004).
Parisien and Major, "The MC-Fold and MC-Sym pipeline infers RNA structure from sequence data," *Nature*, 452:51-55 (2008).
Park et al., "Rewiring MAP kinase pathways using alternative scaffold assembly mechanisms," *Science*, 299:1061-1064 (2003).
Pelletier and Sonenberg, "Insertion mutagenesis to increase secondary structure within the 5' noncoding region of a eukaryotic mRNA reduces translational efficiency," *Cell*, 40:515-526 (1985).
Penchovsky and Breaker, "Computational design and experimental validation of oligonucleotide-sensing allosteric ribozymes," *Nat. Biotechnol.*, 23:1424-1433 (2005).
Penedo et al., "Folding of the natural hammerhead ribozyme is enhanced by interaction of auxiliary elements," *RNA*, 10(5):880-888 (2004).

(56) References Cited

OTHER PUBLICATIONS

Perry-O'Keefe et al., "Peptide nucleic acid pre-gel hybridization: an alternative to Southern hybridization," *Proc. Natl. Acad. Sci. USA*, 93:14670-14675 (1996).
Pfleger et al., "Combinatorial engineering of intergenic regions in operons tunes expression of multiple genes," *Nat. Biotech.*, 24:1027-1032 (2006).
Piganeau et al., "In vitro selection of allosteric ribozymes: theory and experimental validation," *J. Mol. Biol.*, 312:1177-1190 (2001).
Pley et al, "Three-dimensional structure of a hammerhead ribozyme," *Nature*, 372:68-74 (1994).
Qi and Elion, "MAP Kinase Pathways," *J. Cell Sci.*, 118(16):3569-3571 (2005).
Raab and Stephanopoulos, "Dynamics of gene silencing by RNA interference," *Biotechnol. Bioeng.*, 88:121-132 (2004).
Rand et al., "Argonaute2 cleaves the anti-guide strand of siRNA during RISC activation," *Cell*, 123:621-629 (2005).
Rinaudo et al., "A universal RNAi-based logic evaluator that operates in mammalian cells," *Nat. Biotechnol.*, 25:795-801 (2007).
Robertson and Ellington, "Design and optimization of effector-activated ribozyme ligases," *Nucleic Acids Res.*, 28:1751-1759 (2000).
Robertson and Ellington, "In vitro selection of an allosteric ribozyme that transduces analytes to amplicons," *Nat. Biotechnol.*, 17:62-66 (1999).
Rodionov et al., "Reconstruction of regulatory and metabolic pathways in metal-reducing δ-proteobacteria," *Genome Biol.*, 5:R90.1-R90.27 (2004).
Rossi, "Targeted cleavage: Tuneable cis-cleaving ribozymes," *PNAS*, 104(38):14881-14882 (2007).
Rossolini et al., "Use of deoxyinosine-containing primers vs degenerate primers for polymerase chain reaction based on ambiguous sequence information," *Mol. Cell Probes*, 8:91-98 (1994).
Roth and Breaker, "Selection in vitro of allosteric ribozymes," *Methods Mol. Biol.*, 252:145-164 (2004).
Roychowdhury-Saha et al., "Flavin recognition by an RNA aptamer targeted toward FAD," *Biochemistry*, 41(8):2492-2499 (2002).
Ruckman et al., "2'-Fluoropyrimidine RNA-based Aptamers to the 165-Amino Acid Form of Vascular Endothelial Growth Factor (VEGF165)," *J. Biol. Chem.*, 273(32):20556-20567 (1998).
Rusconi et al., "Blocking the Initiation of Coagulation by RNA Aptamers to Factor VIIa," *Thromb. Haemost.*, 84(5):841-848 (2000).
Saksmerprome et al., "Artificial tertiary motifs stabilizing *trans*-cleaving hammerhead ribozymes under conditions of submillimolar divalent ions and high temperatures," *RNA*, 10(12):1916-1924 (2004).
Salehi-Ashtiani and Szostak, "In vitro evolution suggests multiple origins for the hammerhead ribozyme," *Nature*, 414:82-84 (2001).
Samarsky et al., "A small nucleolar RNA:ribozyme hybrid cleaves a nucleolar RNA target in vivo with near-perfect efficiency," *Proc. Natl. Acad. Sci. USA*, 96:6609-6614 (1999).
Saran et al., "The tyranny of adenosine recognition among RNA aptamers to coenzyme A," *BMC Evol. Biol.*, 3(I):26 (2003).
Sarin et al., "Inhibition of acquired immunodeficiency syndrome virus by oligodeoxynucleoside methylphosphonates," *Proc. Natl. Acad. Sci. USA*, 85:7448-7451 (1988).
Sarver et al., "Ribozymes as potential anti-HIV-1 therapeutic agents," *Science*, 247:1222-1225 (1990).
Scherer and Rossi, "Approaches for the sequence-specific knockdown of mRNA," *Nat. Biotechnol.*, 21:1457-1465 (2003).
Scherer and Rossi, "Recent applications of RNAi in mammalian systems," *Curr. Pharm. Biotechnol.*, 5:355-360 (2004).
Scherr et al., "Specific hammerhead ribozyme-mediated cleavage of mutant N-*ras* mRNA in vitro and ex vivo," *J. Biol. Chem.*, 272(22):14304-14313 (1997).
Schneider et al, "Selective enrichment of RNA species for tight binding to *Escherichia coli* rho factor," *FASEB J.*, 7(1): 201-207 (1993).
Schwarz et al., "Evidence that siRNAs Function as Guides, Not Primers, in the *Drosophila* and Human RNAi Pathways," *Mol. Cell*, 10:537-548 (2002).

Seelig et al., "Enzyme-Free Nucleic Acid Logic Circuits," *Science*, 314:1585-1588 (2006).
Shalgi et al., "Global and Local Architecture of the Mammalian microRNA-Transcription Factor Regulatory Network," *PLoS Comput. Biol.*, 3:e131 (2007).
Shapiro and Gil, "RNA computing in a living cell," *Science*, 322:387-388 (2008).
Shapiro, "Discovering New MPA Kinase Inhibitors," *Chem. Biol.*, 13(8):807-809 (2006).
Silverman, "Rube Goldberg Goes (RIBO)Nuclear? Molecular Switches and Sensors Made from RNA," *RNA*, 9:377-383 (2003).
Smolke et al., "Controlling the metabolic flux through the carotenoid pathway using directed mRNA processing and stabilization," *Met. Eng.*, 3:313-321 (2001).
Smolke and Keasling, "Effect of gene location, mRNA secondary structures, and Rnase sites on expression of two genes in an engineered operon," *Biotech. Bioeng.*, 80:762-776 (2002).
Smolke and Keasling, "Effect of copy number and mRNA processing and stabilization on transcript and protein levels from an engineered dual-gene operon," *Biotech. Bioeng.*, 78:412-424 (2002).
Smolke et al., "Effects of transcription induction homogeneity and transcript stability on expression of two genes in a constructed operon," *Appl. Micro. Biotech.*, 57:689-696 (2001).
Smolke et al., "Coordinated, differential expression of two genes through directed mRNA cleavage and stabilization by secondary structures," *Appl. Environ. Microbiol.*, 66:5399-5405 (2000).
Smolke et al., "Molecular Switches for Cellular Sensors," *Engineering & Science*, 67(4):28-37 (2005).
Smolke, "Building outside of the box: iGEM and the BioBricks Foundation," *Nat. Biotech.*, 27:1099-1102 (2009).
Smolke, "It's the DNA that counts," *Science*, 324:1156-1157 (2009).
Sontheimer, "Assembly and Function of RNA Silencing Complexes," *Nat. Rev. Mol. Cell Biol.*, 6(2):127-138 (2005).
Soukup and Breaker, "Engineering precision RNA molecular switches," *Proc. Natl .Acad. Sci. USA*, 96:3584-3589 (1999).
Soukup and Breaker, "Relationship between internucleotide linkage geometry and the stability of RNA," *RNA*, 5:1308-1325 (1999).
Soukup and Soukup, "Riboswitches exert genetic control through metabolite-induced conformational change," *Curr. Opin. Struct. Biol.*,14:344 (2004).
Soukup et al., "Altering molecular recognition of RNA aptamers by allosteric selection," *J. Mol. Biol.*, 298:623-632 (2000).
Soukup and Breaker, "Design of allosteric hammerhead ribozymes activated by ligand-induced structure stabilization," *Structure*, 7:783-791 (1999).
Soukup et al., "Generating new ligand-binding RNAs by affinity maturation and disintegration of allosteric ribozymes," *RNA*, 7:524-536 (2001).
Soukup and Breaker, "Nucleic acid molecular switches," *Trends in Biotechnology*, 17:469-476 (1999).
Stein and Cohen, "Oligodeoxynucleotides as inhibitors of gene expression: a review," *Cancer Res.*, 48:2659-2668 (1988).
Stein et al., "Physicochemical properties of phosphorothioate oligodeoxynucleotides," *Nucl. Acids Res.*, 16:3209-3221 (1988).
Stern et al., "A system for Cre-regulated RNA interference in vivo," *Proc. Natl. Acad. Sci. USA*, 105:13895-13900 (2008).
Stojanovic et al., "A deoxyribozyme-based molecular automaton," *Nat. Biotechnol.*, 21:1069-1074 (2003).
Stojanovic and Kolpashchikov, "Modular aptameric sensors," *J. Am. Chem. Soc.*, 126:9266-9270 (2004).
Sudarsan et al., "Metabolite-binding RNAa domains are present in the genes of eukaryotes," *RNA*, 9:644-647 (2003).
Sudarsan et al., "Tandem riboswitch architectures exhibit complex gene control functions," *Science*, 314(5797):300-304 (2006).
Süel et al., "Tunability and noise dependence in differentiation dynamics," *Science*, 315:1716-1719 (2007).
Suess et al., "A theophylline responsive riboswitch based on helix slipping contois gene expression in vivo," *Nucleic Acids Res.*, 32(4):1610-1614 (2004).
Suess et al., "Conditional gene expression by controlling translation with tetracycline-binding aptamers," *Nucleic Acids Res.*, 31:1853-1858 (2003).

(56) References Cited

OTHER PUBLICATIONS

Suess and Weigand, "Engineered riboswitches: overview, problems and trends," *RNA Biol.*, 5(1):1-6 (2008).
Sui et al., "A DNA vector-based RNAi technology to suppress gene expression in mammalian cells," *Proc. Natl. Acad. Sci. USA*, 99:5515-5520 (2002).
Sun et al., "Multi-miRNA hairpin method that improves gene knockdown efficiency and provides linked multi-gene knockdown," *Biotechniques*, 41:59-63 (2006).
Tahiri-Alaoui et al., "High affinity nucleic acid aptamers for streptavidin incorporated into bispecific capture ligands," *Nucleic Acids Res.*, 30(10):e45 (2002).
Taira et al., "Construction of a novel RNA-transcript-trimming plasmid which can be used both in vitro in place of run-off and (G)-free transcriptions and in vivo as multi-sequences transcription vectors," *Nucleic Acids Res.*, 19:5125-5130 (1991).
Takeno et al., "Selection of an RNA Molecual That Specifically Inhibits the Protease Activity of Subtilisin," *J. Biochem.*, 125(6):1115-1119 (1999).
Tang and Breaker, "Rational design of allosteric ribozymes," *Chem. Biol.*, 4:453-459 (1997).
Tao and Frankel, "Arginine-binding RNAs resembling TAR identified by in vitro selection," *Biochemistry*, 35(7):2229-2238 (1996).
Thompson et al., "Group I aptazymes as genetic regulatory switches," *BMC Biotechnol.*, 2:21 (2002).
Tuerk et al., "RNA pseudoknots that inhibit human immunodeficiency virus type I reverse transcriptase," *Proc. Natl. Acad. Sci. USA*, 89:6988-6992 (1992).
Tuerk and Gold, "Systematic evolution of ligands by exponential enrichment: RNA ligands to bacteriophage T4 DNA polymerase," *Science*, 249:505-510 (1990).
Tuleuova et al., "Modulating endogenous gene expression of mammalian cells via RNA-small molecule interaction," *Biochem. Biophys. Res. Commun.*, 376:169-173 (2008).
Ulrich et al., "In vitro selection of RNA molecules that displace cocaine from the membrane-bound nicotinic acetylcholine receptor," *Proc. Natl. Acad. Sci. USA*, 95(24):14051-14056 (1998).
Urvil et al., "Selection of RNA aptamers that bind specifically to the NS3 protease of hepatitis C virus," *Eur. J. Biochem.*, 248(I):130-138 (1997).
Vacek et al., "Antisense-mediated redirection of mRNA splicing," *Cell Mol. Life Sci.*, 60:825-833 (2003).
Vaish et al., "A novel, modification-dependent ATP-binding aptamer selected from an rna library incorporating a cationic functionality," *Biochemistry*, 42(29):8842-8851 (2003).
Van Der Krol et al., "Modulation of eukaryotic gene expression by complementary RNA or DNA sequences," *Biotechniques*, 6:958-976 (1988).
Ventura et al., "Targeted Deletion Reveals Essential and Overlapping Functions of the *miR*-17~92 Family of miRNA Clusters," *Cell*, 132:875-886 (2008).
Villemaire et al., "Reprogramming Alternative Pre-Messenger RNA Splicing through the Use of Protein-binding Antisense Oligonucleotides," *Biol. Chem.*, 278(50):50031-50039 (2005).
Voigt, "Genetic parts to program bacteria," *Curr. Opin. Biotechnol.*, 17:548-557 (2006).
Vuyisich and Beal, "Controlling protein activity with ligand-regulated RNA aptamers," *Chem. Biol.*, 9:907-913 (2002).
Wagner et al., "Nucleotide sequence of the thymidine kinase gene of herpes simplex virus type 1," *Proc. Natl. Acad. Sci. USA*, 78:1441-1445 (1981).
Wagner, "Gene inhibition using antisense oligodeoxynucleotides," *Nature*, 372:333-335 (1994).
Wallace and Schroeder, "In vitro selection and characterization of streptomycin-binding RNAs: Recognition discrimination between antibiotics," *RNA*, 4(I):112-123 (1998).
Wang et al., "General and Specific Functions of Exonic Splicing Silencers in Splicing Control," *Molecular Cell.*, 23:61-70 (2006).
Wang and Wu, "MicroRNA-based therapeutics for cancer," *BioDrugs*, 23:15-23 (2009).
Wang et al., "Recent patents on the identification and clinical application of microRNAs and target genes," *Recent Pat. DNA Gene Seq.*, 1:116-124 (2007).
Wang et al., "RNA molecules that specifically and stoichiometrically bind aminoglycoside anitibiotics with high affinities," *Biochemistry*, 35(38):12338-12346 (1996).
Wang et al., "A general approach for the use of oligonucleotide effectors to regulate the catalysis of RNA-cleaving ribozymes and DNAzymes," *Nucleic Acids Res.*, 30:1735-1742 (2002).
Wang et al., "A general strategy for effector-mediated control of RNA-cleaving ribozymes and DNA enzymes," *J. Mol. Biol.*, 318:33-43 (2002).
Watkins and German, "Metabolomics and biochemical profiling in drug discovery and development," *Curr. Opin. Mol. Ther.*, 4:224-228 (2002).
Weigand and Suess, "Tetracycline aptamer-controlled regulation of pre-mRNA splicing in yeast," *Nucleic Acids Res.*, 35:4179-4185 (2007).
Weigand et al., "Screening for engineered neomycin riboswitches that control translation initiation," *RNA*, 14:89-97 (2008).
Weinberg and Rossi, "Comparative single-turnover kinetic analyses of *trans*-cleaving hammerhead ribozymes with naturally derived non-conserved sequence motifs," *FEBS Lett.*, 579(7):1619-1624 (2005).
Weinberg et al., "Effective anti-hepatitis B virus hammerhead ribozymes derived from multimeric precursors," *Oligonucleotides*, 17(1):104-112 (2007).
Weiss et al., "Antisense RNA gene therapy for studying and modulating biological processes," *Cell Mol. Life Sci.*, 55:334-358 (1999).
Welz and Breaker, "Ligand binding and gene control characteristics of tandem riboswitches in *Bacillus anthracis*," *RNA*, 13:573 (2007).
Werstuck and Green, "Controlling gene expression in living cells through small molecule-RNA interactions," *Science*, 282:296-298 (1998).
Westerhout and Berkhout, "A systematic analysis of the effect of target RNA structure on RMA landscapes of single nucleic acid hairpins," *Proc. Natl. Acad. Sci. USA*, 103:6190-6195 (2006).
Wieland and Hartig, "Improved aptazyme design and in vivo screening enable riboswitching in bacteria," *Angew Chem. Int. Ed. Eng.*, 147:2604-2607 (2008).
Wieland et al., "Artificial ribozyme switches containing natural riboswitch aptamer domains," *Angew Chem. Int. Ed. Eng.*, 148:2715-2718 (2009).
Wieland and Hartig, "Artificial riboswitches: synthetic mRNA-based regulators of gene expression," *ChemBioChem.*, 9:1873-1878 (2008).
Wilda et al., "Killing of leukemic cells with a BCRIABL fusion gene by RNA interference I (RNAi)," *Oncogene*, 21:5716-5724 (2002).
Wilson and Szostak, "In vitro selection of functional nucleic acids," *Annu. Rev. Biochem.*, 68:611-647 (1999).
Wilson et al., "Functional requirements for specific ligand recognition by a biotin-binding RNA pseudoknot," *Biochemistry*, 37:14410-14419 (1998).
Wilson et al., "The interaction of intercalators and groove-binding agents with DNA triplehelical structures: the influence of ligand structure, DNA backbone modifications and sequence," *J. Mol. Recognit.*, 7:89-98 (1994).
Win et al., "Codeine-binding RNA aptamers and rapid determination of their binding constants using a direct coupling surface plasmon resonance assay," *Nucleic Acids Res.*, 34:5670-5682 (2006).
Win et al., "Frameworks for programming biological function through RNA parts and devices," *Chem. Biol.*, 16:298-310 (2009).
Win and Smolke, "Higher-order cellular information processing with synthetic RNA devices," *Science*, 322:456-460 (2008).
Win and Smolke, "A modular and extensible RNA-based gene-regulatory platform for engineering cellular function," *PNAS*, 104:14283-14288 (2007).
Win and Smolke, "RNA as a versatile and powerful platform for engineering genetic regulatory tools," *Biotech. Genet. Eng. Revs.*, 24:311-346 (2007).
Winkler et al., "An mRNA Structure that Controls Gene Expression by Binding FMN," *PNAS*, 99:15908-15913 (2002).

(56) References Cited

OTHER PUBLICATIONS

Winkler et al., "Control of gene expression by a natural metabolite-responsive ribozyme," *Nature*, 428:281-286 (2004).
Winkler and Breaker, "Genetic Control by Metabolite-Binding Riboswitches," *ChemBioChem*, 4:1024-1032 (2003).
Winkler et al., "Thiamine derivatives bind messenger RNAs directly to regulate bacterial gene expression," *Nature*, 419:952-956 (2002).
Woodside et al., "Nanomechanical measurements of the sequence-dependent folding landscapes of single nucleic acid hairpins," *Proc. Natl. Acad. Sci. USA*, 103:6190-6195 (2006).
Xia et al., "Multiple shRNAs expressed by an inducible pol II promoter can knock down the expression of multiple target genes," *Biotechniques*, 41:64-68 (2006).
Yamamoto et al., "Identification of a functional promoter in the long terminal repeat of Rous sarcoma virus," *Cell*, 22:787-797 (1980).
Yang et al., "DNA ligands that bind tightly and selectively to cellobiose," *PNAS*, 95(10):5462-5467 (1998).
Yelin et al., "Widespread occurrence of antisense transcription in the human genome," *Nat. Biotechnol.*, 21:379-386 (2003).
Yen et al., "Exogenous control of mammalian gene expression through modulation of RNA self-cleavage," *Nature*, 431:471-476 (2004).
Yeom et al., "Characterization of DGCR8/Pasha, the essential cofactor for Drosha in primary miRNA processing," *Nucleic Acids Res.*, 34(16):4622-4629. Epub Sep. 8, 2006.
Yi et al., "Exportin-5 mediates the nuclear export of premicroRNAs and short hairpin RNAs," *Genes Dev.*, 17:3011-3016 (2003).
Yi et al., "Overexpression of exportin 5 enhances RNA interference mediated by short hairpin RNAs and microRNAs," *RNA*, 11:220-226 (2005).
Yokobayashi et al., "Directed evolution of a genetic circuit," *Proc. Natl. Acad. Sci. USA*, 99:16587-16591 (2002).
Yu et al., "RNA interference by expression of short-interfering RNAs and hairpin RNAs in mammalian cells," *Proc. Natl. Acad. Sci. USA*, 99:6047-6052 (2002).
Yunusov et al., "Kinetic capillary electrophoresis-based affinity screening of aptamer clones," *Anal. Chim. Acta.*, 631(1):102-107 (2009).
Zaug et al., "A labile phosphodiester bond at the ligation junction in a circular intervening sequence RNA," *Science*, 224:574-578 (1984).
Zaug and Cech, "The intervening sequence RNA of *Tetrahymena* is an enzyme," *Science*, 231:470-475 (1986).
Zaug et al., "The *Tetrahymena* ribozyme acts like an RNA restriction endonuclease," *Nature*, 324:429-433 (1986).
Zeng and Cullen, "Structural requirements for pre-microRNA binding and nuclear export by Exportin 5," *Nucleic Acids Res.*, 32(16):4776-4785 (2004).
Zeng et al., "Both natural and designed micro RNAs can inhibit the expression of cognate mRNAs when expressed in human cells," *Mol. Cell*, 9:1327-1333 (2002).
Zeng et al., "Efficient processing of primary microRNA hairpins by Drosha requires flanking nonstructured RNA sequences," *J. Biol. Chem.*, 280:27595-27603 (2005).
Zeng et al., "Recognition and cleavage of primary microRNA precursors by the nuclear processing enzyme Drosha," *EMBO J.*, 24:138-148 (2005).
Zeng and Cullen, "Sequence requirements for micro RNA processing and function in human cells," *RNA*, 9:112-123 (2003).
Zhou et al., "Novel Dual Inhibitory Function Aptamer—siRNA Delivery System for HIV-1 Therapy," *Mol. Ther.*, 16:1481-1489 (2008).
Zimmermann et al., "Interlocking structural motifs mediate molecular discrimination by a theophylline-binding RNA," *Nat. Struct. Biol.*, 4:644-649 (1997).
Zimmermann et al., "Molecular interactions and metal binding in the theophylline-binding core of an RNA aptamer," *RNA*, 6:659-667 (2000).
Zon, "Oligonucleotide analogues as potential chemotherapeutic agents," *Pharm. Res.*, 5:539-549 (1988).

\* cited by examiner

GENERAL COMPOSITION FRAMEWORK FOR LIGAND-CONTROLLED RNA REGULATORY SYSTEMS

CROSS-REFERENCE TO RELATED APPLICATIONS

This application is a continuation of U.S. patent application Ser. No. 12/228,665, filed on Aug. 14, 2008; which claims the benefit of the filing date under 35 U.S.C. §119(e) to U.S. Provisional Application No. 60/966,398, filed on Aug. 28, 2007, the entire content of each of which (including the specification and drawings) is incorporated herein by reference.

STATEMENT REGARDING FEDERAL FUNDING

Work described herein was funded, in whole or in part, by Grant No. NIH-R21 GM074767-01A1 awarded by the National Institute of Health (NIH), and Grant No. DoD-W81XWH-06-1-0250 awarded by the United States Department of Defense (DoD). The United States Government has certain rights in this invention.

BACKGROUND OF THE INVENTION

Basic and applied biological research and biotechnology are limited by the ability to get information into and from living systems and to act on information inside living systems. For example, there are only a small number of inducible promoter systems available to provide control over gene expression in response to exogenous molecules. Many of the molecular inputs to these systems are not ideal for broad implementation, because they can be expensive and introduce undesired pleiotropic effects. In addition, broadly applicable methods for getting information from cells noninvasively have been limited to strategies that rely on protein and promoter fusions to fluorescent proteins, which enable researchers to monitor protein levels and localization and transcriptional outputs of networks, leaving a significant amount of the cellular information content currently inaccessible.

A striking example of a biological communication and control system is the class of RNA-regulatory elements called riboswitches, comprising distinct sensor and actuation (gene-regulatory) functions, that control gene expression in response to specific ligand concentrations. Building on these natural examples, engineered riboswitch elements have been developed for use as synthetic ligand-controlled gene-regulatory systems. However, research to date has largely focused on the generation of specific instances of RNA devices, which do not necessarily guide researchers in how to translate that particular instance into other instances useful for specific systems or applications. Often times, the activity of these RNA devices is dependent on the particular system in which it was developed, including sequences immediately surrounding the regulator element, and modularity is not maintained.

As a result, these early examples of switch engineering do not address the challenges posed above, because they lack portability across organisms and systems, and their designs and construction do not support modularity and component reuse.

SUMMARY OF THE INVENTION

The invention described herein provides general design principles and methods for implementing such principles, for constructing ligand-regulated polynucleotide devices. These general design principles establish a framework to translate RNA engineering into a broadly applicable field, in that modular molecular platforms are employed to allow rapid, yet reliable construction of distinct ligand-regulated polynucleotide devices using a variety of RNA regulators which are functionally independent of the particular system in which they origin. The resulting ligand-regulated polynucleotide devices or gene-regulatory systems can be used in a wide variety of biological systems to, for example, control the expression of specific target genes in response to various effector molecules, or sense the presence/change of concentration of the effector molecules, and/or the change in status of an environmental condition (pH, temperature, ion concentration, etc.).

Specifically, the invention provides five engineering design principles (DPs) in achieving this goal: DP1, scalability (a sensing platform enabling de novo generation of ligand-binding elements for implementation within the sensor domain); DP2, portability (a regulatory element (such as ribozyme) that may be independent of cell-specific machinery or regulatory mechanisms for implementation within the actuator domain, or a regulatory element that may depend on the cell-specific machinery but is largely independent of cell type); DP3, utility (a mechanism through which to modularly couple the control system to functional level components); DP4, composability (a mechanism by which to modularly couple the actuator and sensor domains without disrupting the activities of these individual elements); and DP5, reliability (a mechanism through which to standardize the transmission of information from the sensor domain to the actuator domain).

The invention also provides a distinct or improved design for a strand displacement mechanism-based switch (ligand-controlled regulatory systems), by utilizing an improved information transmission domain (ITD). The improved ITD eliminates free-floating ends of the switching and the competing strands, and localizes competitive hybridization events to a contiguous strand of competing strand and switching strand in the switch, thereby improving the kinetics of strand-displacement. This design results in a distinct, and preferably improved strand displacement kinetics than other designs, such as certain strand-slippage mechanism (or helix slipping internal mechanism) based design used in the prior art.

Thus one aspect of the invention provides a polynucleotide comprising: (1) a modular actuator domain having one or more functional activities, wherein the modular actuator domain is not a ribozyme, (2) a modular sensor domain that detects concentration change of a molecule, or status change of an environmental condition (pH, ion concentration, temperature), and, (3) an information transmission domain between the modular actuator domain and the modular sensor domain, the information transmission domain comprising: (a) a general transmission region, (b) a switching strand, (c) a competing strand, wherein the switching strand and the competing strand are in a continuous sequence and compete to bind to the general transmission region through hybridization interactions; wherein detection of the concentration or status change by the modular sensor domain favors a conformation change in the modular actuator domain; wherein the conformation change is mediated by a strand-displacement mechanism in the information transmission domain to favor the binding of the general transmission region to one of the switching strand and the competing strand; and, wherein the conformation change modulates the functional activity of the actuator domain.

Depending on the specific identity of the actuator domain, its functional activity may include: the ability to serve as a substrate for an RNAi (RNA interference) pathway enzyme, such as Dicer or other RNase III enzyme; the ability to hybridize with a target nucleic acid and inhibit the expression of a protein encoded by the target nucleic acid; the ability to hybridize with a target nucleic acid and serve as template for nucleic acid amplification; the ability to modulate splicing; and/or the ability to become a target sequence for siRNA (small interfering RNA), miRNA (microRNA), or antisense sequence, etc. Other functional activities of the various actuator domains are described below in conjunction with the description of the various actuator domains.

In a related aspect, the invention provides a method for rational design of a modular polynucleotide, the method comprising: (1) providing a modular actuator domain having one or more functional activities, wherein the modular actuator domain is not a ribozyme, (2) providing a modular sensor domain that detects concentration change of a molecule, or status change of an environmental condition (pH, ion concentration, temperature), and, (3) providing an information transmission domain between the modular actuator domain and the modular sensor domain, the information transmission domain comprising: (a) a general transmission region, (b) a switching strand, (c) a competing strand, wherein the switching strand and the competing strand are in a continuous sequence and compete to bind to the general transmission region through hybridization interactions; wherein detection of the concentration or status change by the modular sensor domain favors a conformation change in the modular actuator domain; wherein the conformation change is mediated by a strand-displacement mechanism in the information transmission domain to favor the binding of the general transmission region to one of the switching strand and the competing strand; and, wherein the conformation change modulates the functional activity of the actuator domain.

In another related aspect, the invention provides a method for improving the design of a sensor-regulated polynucleotide, the polynucleotide comprising: (1) an actuator domain having one or more functional activities, wherein the actuator domain is not a ribozyme, and, (2) a sensor domain that detects concentration change of a molecule, or status change of an environmental condition (pH, ion concentration, temperature), the method comprising: providing an information transmission domain between the actuator domain and the sensor domain, the information transmission domain comprising: (a) a general transmission region, (b) a switching strand, (c) a competing strand, wherein the switching strand and the competing strand are in a continuous sequence and compete to bind to the general transmission region through hybridization interactions; wherein detection of the concentration or status change by the sensor domain favors a conformation change in the actuator domain; wherein the conformation change is mediated by a strand-displacement mechanism in the information transmission domain to favor the binding of the general transmission region to one of the switching strand and the competing strand; and, wherein the conformation change modulates the functional activity of the actuator domain.

In certain embodiments, the polynucleotide comprises RNA, DNA, or a combination thereof.

In certain embodiments, the polynucleotide comprises one or more modified nucleotides or nucleotide analogs.

In certain embodiments, the polynucleotide is single-stranded.

In certain embodiments, the modular actuator domain comprises an antisense sequence, an siRNA or precursor thereof, an miRNA or precursor thereof, an shRNA (short hairpin RNA) or precursor thereof, an RNase III substrate, an alternative splicing element, or an RNAi targeting sequence. For example, the conformational change may produce or remove an intramolecular double-stranded feature in the actuator domain (which includes the RNase III substrate sequence), where the double-stranded feature is the substrate for the extrinsic enzymatic activity, e.g., an RNase III enzyme activity. In certain cases, the RNase III enzyme is Dicer or Drosha. In those embodiments, the substrate sequence is selected to produce siRNA, miRNA or a precursor or metabolite thereof in an RNA interference pathway, as a product of reaction with the RNase III enzyme. In a related embodiment, the substrate sequence forms a pri-miRNA or pre-miRNA substrate for Drosha (i.e., localized in the nucleus), and the product of Drosha-mediated cleavage is an miRNA that can translocate to the cytoplasm and be acted on by Dicer, i.e., inputs into the RNA interference pathway.

In another illustration, the conformation change can be one that alters the ability of the substrate sequence to form an intermolecular double-stranded feature with a second (discrete) nucleic acid species, such as a target gene, where the double-stranded feature is the substrate for the extrinsic enzymatic activity. For instance, the second nucleic acid species can be an mRNA, and the extrinsic enzymatic activity alters the mRNA in a manner dependent on the formation of the double-stranded feature with the switch actuator domain, such as by activation of an RNase H enzyme and/or RNase P enzyme or the like.

In still other examples, ligand binding to the aptamer can induce or prevent the substrate sequence from forming a substrate for such other extrinsic enzymatic activities as polymerases, recombinases, ligases, methylases, glycosylases, or nucleases.

Similarly, the antisense sequence can be selected to alter the levels of expression of different splice variants through hybridization to transcripts in a manner that effects intron splicing.

In still other embodiments, the targeting sequence inhibits expression of the target gene through homologous recombination with the target gene, and becomes a substrate for recombinase in a manner dependent upon the ligand-induced conformational change.

In certain embodiments, the actuator domain can be selected to hybridize to an RNA transcript of the target gene and thereby reduce the amount of protein translated from the RNA transcript, and/or alter splicing of the RNA transcript. Alternatively, the targeting sequence can be selected to hybridize to a genomic sequence of the target gene and reduces the amount of RNA transcribed from the genomic sequence.

In certain embodiments, the modular actuator domain comprises a substrate for RNase III, wherein the substrate, when processed by RNase III, produces an siRNA or miRNA that targets a transcript of the target gene.

In certain embodiments, the subject switch includes a polyadenylate tail, or in the case of the expression constructs, a coding sequence that when transcribed, produces a poly-A tail on the switch transcript. It will be appreciated by those skilled in the art that the subject switch constructs can be derived from various nucleotides and nucleotide analogs, as well as utilizing various linkage chemistries, such as may be adapted for use in the present invention from the art of antisense and siRNA constructs. To further illustrate, the switch can include one or more non-naturally occurring nucleoside analogs and/or one or more non-naturally occurring backbone linkers between nucleoside residues. Such analogs and linkers can be used to alter the stability, nuclease susceptibility (or resistance) and/or bioavailability (such as cell permeability) relative to a corresponding nucleic acid of naturally occurring nucleosides and phosphate backbone linkers.

In certain embodiments, the polynucleotide is functional in vivo.

In certain embodiments, the modular actuator domain has the one or more functional activities in vivo. For example, the functional activities may comprise an ability to hybridize with a target polynucleotide, an ability to be incorporated into a RISC complex to serve as an siRNA or miRNA guide sequence, or an ability to be an RNase III substrate.

In certain embodiments, the modular sensor domain is an aptamer.

In certain embodiments, the modular sensor domain binds the molecule, preferably specifically. In certain preferred embodiments, ligand binding and the resulting macro level conformation change is dependent on the dose or concentration of the ligand, though the does-response curve is not necessarily linear.

In certain embodiments, the molecule has a molecular weight of no more than about 2000 Da, 1000 Da, 500 Da, 300 Da, 200 Da, 100 Da, or 50 Da.

In certain embodiments, the molecule/ligand is a small peptide, a nucleic acid, a carbohydrate, a fatty acid or lipid, a non-peptide hormone (such as steroid), an amino acid or precursor thereof, a nucleotide or precursor thereof, a vitamin, a metal ion, a metabolite, a post-translationally modified protein, a signal transduction second messenger, an enzyme co-factor, an enzyme substrate, a product of an enzyme-mediated reaction, or a metabolic precursor or product thereof.

Particularly for embodiments where it is intended that the subject switch be regulated using an ectopically administered ligand, the ligand is preferably one that is cell permeable.

In certain embodiments, the ligand can be a molecule produced by the cell. In other embodiments, the ligand can be a cell permeable agent that is contacted with the cell, e.g., either by ectopic addition or by diffusion from a neighboring cell.

Certain embodiments provide tissue or cell type-specific modulation of the concentration and/or activity of a ligand or the expression of a target gene. The tissue or cell type-specific modulation may be achieved by the tissue or cell type-specific presence of the ligand. For example, the aptamer domain of an aptamer-regulated nucleic acid may be responsive to a tissue or cell type-specific ligand and the effector domain targets a ligand to modulate the concentration and/or activity of the ligand. In another aspect, the aptamer domain of an aptamer-regulated nucleic acid is responsive to a tissue or cell type-specific ligand and the actuator domain targets a target gene to modulate the expression of the target gene.

In certain embodiments, the switching strand and the competing strand substantially do not overlap.

In certain embodiments, the switching strand and the competing strand have substantially the same sequence.

In certain embodiments, the switching strand and the competing strand are in tandem. For example, the switching strand and the competing strand may be directly linked with each other in the polynucleotide, optionally with a few linker nucleotides. The switching strand and the competing strand may or may not be mutually exclusive, and they may overlap by a few nucleotides (e.g., 1, 2, 3, 4, 5, 6, 7, 8, or 9 nucleotides, for example).

In certain embodiments, the switching strand and/or the competing strand are each at least 3, 4, 5, 6, 7, 8, 9, 10, 11, 12, 13, 14, 15, 16, 17, 18, 19, 20, or more nucleotides in length.

In certain embodiments, the conformation change increases the functional activities. In other embodiments, the conformation change decreases the functional activities.

In certain embodiments, the extent of the conformation change in response to ligand/molecule concentration or status change is amenable to (rational) adjustment/tuning.

For example, the adjustment/tuning may be achieved through rational sequence modification in the information transmission domain (to affect structure stability and/or to vary the energy barrier between the two adoptable conformations). Alternatively, the adjustment/tuning is effectuated by modifying base-pairing interactions among the general transmission region, the switching strand, and/or the competing strand. Alternatively, the adjustment/tuning is effectuated by changing the length of the paring base-pairs at one or both ends of the duplex formed between the general transmission region and the switching strand, and/or the duplex formed between the general transmission region and the competing strand. Alternatively, the adjustment/tuning is effectuated by changing base-pairing complementarity. Alternatively, adjustment/tuning is effectuated by changing the binding affinity between the modular sensor domain and the molecule without changing the size of the modular sensor domain. Alternatively, the adjustment/tuning is effectuated by changing the size of the modular sensor domain. Depending on specific mechanisms of action of the actuator domains, this may alter the processing efficiency of the polynucleotide (e.g., when the actuator domain is an RNase III substrate), the ability of an antisense actuator domain to bind its target sequence, or the cleavage activity of a ribozyme actuator domain, etc.

In certain embodiments, the extent of the conformation change in response to ligand/molecule concentration or status change is amenable to (rational) adjustment/tuning effectuated by any one or more of the mechanisms described above.

Thus certain embodiments provide methods of designing, selecting, or optimizing aptamer-regulated nucleic acids or aptamer domains that are responsive to one or more preselected or pre-determined ligands. Such switches may also be "tuned" so that their switching behavior is more or less responsive to ligand binding. The switches may also be "tuned" so that the binding affinity of the aptamer domain is more or less sensitive to its ligand. For instance, the thermodynamic properties of intramolecular duplex formation and other 2° and 3° structures in the subject switch may be altered so that the aptamer domain is more or less amenable to ligand binding, i.e., such as may be manifest in the dissociation constant ($K_D$) or other kinetic parameters (such as $K_{on}$ and $K_{off}$ rates). Alternatively, allosteric changes in the effector domain may be more or less responsive to ligand binding upon alterations in hybridization and other intramolecular interactions that may effect 2° and 3° structures of the subject switch. Forward engineering strategies for altering the thermodynamic properties of nucleic acid structures are well known in the art. For instance, increased complementary nucleic acid pairing may increase the stability of an actuator or aptamer domain. It is anticipated that the absolute and relative stabilities of the actuator domain and the aptamer domain will be important design parameters in tuning the switch behavior of a subject switch.

In certain embodiments, the modular actuator domain can be (reliably/predictably) exchanged for a different modular actuator domain without substantially affecting the function of the modular sensor domain and the information transmission domain.

In certain embodiments, the modular sensor domain can be (reliably/predictably) exchanged for a different modular sensor domain without substantially affecting the function of the modular actuator domain and the information transmission domain.

The invention also relates to a vector or expression construct encoding any of the subject polynucleotides.

In certain embodiments, the vector or expression construct may further comprise one or more transcriptional regulatory sequences that regulate transcription from the vector or expression construct in a cell containing the vector or expression construct.

In certain embodiments, the cell is a mammalian cell, a human cell, a rodent cell, a yeast cell, an insect cell, a worm cell, or a bacterium.

The invention also relates to a cell engineered to include any of the subject polynucleotides, or any of the subject vector or expression constructs.

In other aspects, the invention provides a cell comprising: a metabolic pathway of one or more reactions that are regulated at least in part by a target gene; and one or more subject polynucleotides that act as control elements on the metabolic pathway by regulating expression of the target gene through the modular actuator domain, wherein binding of the molecule to the modular sensor domain (e.g., aptamer) causes a change in the intramolecular interaction of information transmission domain, such that there is a change in the regulation of the target gene by the modular actuator domain, at a rate dependent upon the presence or absence of the molecule.

Each of the subject polynucleotide can include (i) an aptamer sequence that selectively binds to a ligand selected from an enzyme co-factor, a reactant, a substrate or a product of a reaction in the metabolic pathway, (ii) an actuator domain, such as a gene silencing sequence for reducing expression of a target gene encoding a protein involved in the metabolic pathway. These may be proteins that act as enzymes in the pathway, or may be proteins that act as regulatory subunits or have other effects on the pathway (such as transcription factors or repressors that control expression of components of the metabolic pathway). In these embodiments, ligand binding to the aptamer causes a change in the regulated nucleic acid between two conformation states, in one of which the regulated nucleic acid inhibits expression of the target gene in a manner dependent on the gene silencing sequence, and in the other of which the regulated nucleic acid does not inhibit expression of the target gene. Thus, the metabolic pathway can be regulated at least in part by the regulated nucleic acid. In certain preferred instances, the metabolic pathway includes at least one reaction mediated by an enzyme, and at least one of the regulated nucleic acid regulates expression of the enzyme.

Another aspect of the invention provides a library of aptamer-regulated nucleic acids, such as libraries having a variegated population of nucleic acids having different aptamers and/or different actuator regions (such as substrate sequences, antisense sequences or targeting sequences as described above). These libraries may have diversity among the aptamers with respect to the types of ligands that can be bound (specificity) and/or the variation in affinity for the same ligand.

In other aspects, the invention provides a method for regulating expression of a recombinant gene, comprising: (i) providing a cell engineered to include any of the subject polynucleotides, or any of the subject vector or expression constructs, (ii) contacting the cell with the molecule in an amount that alters the activity of the modular actuator domain. Preferably, the cell is contacted with the molecule/ligand in an amount that alters the activity of the modular actuator domain to a desired level. The relationship between the activity of the actuator domain and the input molecule concentration may be titrated in vitro or in vivo. The resulting titration curve may be used to provide precise regulation of actuator activity with specific ligand concentration.

Another aspect of the invention provides a method for rendering expression of a target gene in a cell dependent on the presence or absence of a molecule, comprising introducing into the cell a subject polynucleotide comprising a modular actuator domain comprising a substrate for RNase III, wherein the substrate, when processed by RNase III, produces an siRNA or miRNA that targets a transcript of the target gene, wherein, binding of the molecule to the modular sensor domain (e.g., aptamer) causes a change in the intramolecular interaction of the information transmission domain, such that the substrate is processed by RNase III to produce the siRNA or miRNA to target the transcript, at a rate dependent upon the presence or absence of the molecule.

In certain embodiments, the molecule is produced by the cell.

In certain embodiments, the molecule is a cell permeable agent that is contacted with the cell.

Another aspect of the invention provides a method of determining the amount of an analyte in a cell which expresses a reporter gene, comprising: (1) introducing into the cell a subject polynucleotide comprising a modular actuator domain comprising a substrate for RNase III, wherein the substrate, when processed by RNase III, produces an siRNA or miRNA that targets a transcript of the reporter gene, wherein binding of the analyte to the modular sensor domain (e.g., aptamer) causes a change in the intramolecular interaction of the information transmission domain, such that the substrate is processed by RNase III to produce the siRNA or miRNA to inhibit expression of the reporter gene, at a rate dependent upon the presence or absence of the analyte; (2) measuring the amount of expression of the reporter gene; and (3) correlating the amount of expression of the reporter gene with the amount of analyte, thereby determining the amount of the analyte in the cell.

Another aspect of the invention provides a method for treating or preventing infection by a pathogenic agent, comprising administering to a patient a sufficient amount of a subject polynucleotide, wherein the molecule is produced as a consequence of infection by the pathogenic agent, and wherein the modular actuator domain inhibits the function of one or more genes essential for successful infection (e.g., maintenance, replication, or spread of pathogenic infection) by the pathogenic agent. Specifically, binding of the ligand to the aptamer domain favors a conformational change in the nucleic acid that alters the ability of the actuator domain to inhibit the expression of the target gene. The nucleic acid is administered in a sufficient amount to inhibit the expression of pathogen and/or host genes that are important for the maintenance, replication, or spread of pathogenic infection. For example, the aptamer domain of an aptamer-regulated nucleic acid can bind and respond to infection products (e.g., HIV gag, p24, p6, p7, p17, gp120, gp41, pol, env, tat, rev, nef, vif, vpr, vpu, and tev proteins) that are generated upon pathogen infection. Ligand binding to the aptamer domain favors a conformational change in the nucleic acid so that the actuator domain is available to target pathogen and/or host genes that are important for the maintenance or spread of pathogenic infection. Pathogens include, viral, eukaryotic and prokaryotic organisms, including pathogenic viruses, bacteria, and fungi.

Still another aspect of the present invention provides a method of conducting a pharmaceutical business comprising: (a) identifying a subject aptamer-regulated nucleic acid which, depending on specific use, when switched "on" (e.g., when the actuator domain becomes functional or has an increased functional activity) or "off" (e.g., when the actuator domain becomes non-functional or has a decreased functional activity) inhibits proliferation of target cells in vivo and reduces the effects of a disorder involving unwanted proliferation of the target cells; (b) conducting therapeutic profiling of the aptamer-regulated nucleic acid identified in step (a) for efficacy and toxicity in animals; and (c) formulating a pharmaceutical preparation including one or more of the aptamer-regulated nucleic acids identified in step (b) as having an acceptable therapeutic profile.

The method of conducting a pharmaceutical business may further comprise an additional step of establishing a distribution system for distributing the pharmaceutical preparation for sale, and optionally, establishing a sales group for marketing the pharmaceutical preparation.

Yet still another aspect of the present invention provides a method of conducting a pharmaceutical business comprising: (a) identifying a subject aptamer-regulated nucleic acid which, when switched "on," inhibits proliferation of target cells in vivo and reduces the effects of a disorder involving unwanted proliferation of the target cells; (b) (optionally) conducting therapeutic profiling of an aptamer-regulated nucleic acid identified in step (a) for efficacy and toxicity in animals; and (c) licensing, to a third party, the rights for further development of the aptamer-regulated nucleic acid.

The skilled artisan recognizes that an aptamer-regulated nucleic acid that is useful for treating any disorder, including, but not limited to inhibiting pathogenic replication and/or infection, regulation of the immune response, or modulation of the cellular state of a cell, may be used in the methods of conducting a pharmaceutical business.

Another aspect of the invention provides a method for causing phenotypic regulation of cell growth, differentiation or viability in cells of a patient, comprising introducing into cells in the patient a subject polynucleotide, where the modular sensor domain (e.g., aptamer) binds to the molecule, the concentration of which is dependent on cellular phenotype, wherein binding of the molecule to the modular sensor domain favors a conformational change that increases (or decreases) the functional activities of the modular actuator domain, and the increased or decreased functional activities of the modular actuator domain modulates expression of a target gene essential for altering the regulation of cell growth, differentiation or viability in the cells.

Merely for illustration, the method can be used to prevent the growth of hyperplastic or tumor cells, or even the unwanted proliferation of normal cells. It can be used to induce the death of fat cells. It can also be used to regulate growth and differentiation of stem cells, or to regulate activation of an immune response.

In certain embodiments, the method may be used to induce cell death in a manner dependent on the presence of the molecule.

In certain embodiments, the method is used to prevent cell death in a manner dependent on the presence of the molecule.

In certain embodiments, the method may be used to induce differentiation in a manner dependent on the presence of the molecule.

In certain embodiments, the method may be used to inhibit differentiation in a manner dependent on the presence of the molecule.

In certain embodiments, the method is used to prevent the growth of hyperplastic or tumor cells.

In certain embodiments, the method is used to reduce fat cells in the patient.

In certain embodiments, the method is used to regulate growth and differentiation of stem cells.

In certain embodiments, the method is used to regulate activation of an immune response.

In certain embodiments, the polynucleotide, or an expression construct for transcribing the polynucleotide, are introduced ex vivo into cells which are transplanted into the patient.

In certain embodiments, the aptamer-regulated nucleic acid is introduced to cells, in vivo, by contacting the cells with an expression vector having a nucleic acid coding sequence that is transcribed to produce one or more products that produce the aptamer-regulated nucleic acid in the treated cells. In other embodiments, the aptamer-regulated nucleic acid is introduced to cells ex vivo. For example, the aptamer-regulated nucleic acid may be introduced to cells outside of a subject by contacting the cells with an expression vector having a nucleic acid coding sequence that is transcribed to produce one or more products that produce the aptamer-regulated nucleic acid in the treated cells. The cells that are transfected (e.g., stably transfected) with the aptamer-regulated nucleic acid can then be introduced into a subject for treatment. The cells used in ex vivo treatment strategies may be derived from the subject to be treated, from a donor, or from a previously generated stock of maintained cells. Cells that may be used in ex vivo treatment strategies include, but are not limited to, stem cells, somatic cells, and immune cells (e.g., T cells). In a specific embodiment, the invention provides a method for modulating the differentiation of a stem cell, comprising transfecting a stem cell with an aptamer-regulated nucleic acid of the invention, wherein the aptamer-regulated nucleic acid comprises an aptamer domain and an actuator domain (e.g., an effector RNA domain). The aptamer domain is responsive to the binding of a ligand and the effector domain is targeted to a molecule or gene that is sufficient to modulate the differentiation of a stem cell. Stem cells may be differentiated into any cell type (e.g., a dermal cell, a hepatocyte, a retinal cell, etc.).

Another aspect of the invention provides a pharmaceutical preparation comprising a subject polynucleotide, or an expression construct which, when transcribed, produces an RNA including the polynucleotide, and a pharmaceutically acceptable carrier suitable for use administration to a human or non-human patient.

Another aspect of the invention provides a method of using the sequence of an shRNA switch to facilitate the prediction of the relative expression level of a target gene ($f_{model}$) in vivo at the presence of the shRNA switch, the method comprising: (1) using an RNA secondary structure prediction algorithm to provide a first active conformation and a second inactive conformation of the shRNA switch, based on the sequence of the shRNA switch; (2) using a stem method to calculate the free energy difference ($\Delta G_{method}$) between the inactive conformation and the active conformation, wherein the stem method only accounts for the energetics of the major stem(s) in each conformation; (3) calculating the partitioning coefficient between the active and the inactive conformations ($K_{Comp}$) based on $\Delta G_{method}$ obtained in (2); (4) providing a predicted relationship between the relative expression level of target gene and ligand concentration based on $K_{Comp}$ obtained in (3); and, (5) outputting the predicted relationship to a user on an output device, or verifying the predicted relationship with in vitro and/or in vivo experiments at one or more ligand concentration(s), wherein the shRNA switch comprises: (a) a duplex stem region that can be processed to siRNA or miRNA to antagonize the expression of the target gene; (b) an aptamer that can bind a ligand over a range of ligand concentrations, wherein the aptamer is within the loop region of the shRNA; (c) a switching strand within the loop region of the shRNA, and between the duplex stem region and the aptamer, wherein in the first active conformation, the aptamer does not bind the ligand, and the duplex stem region can be processed to the siRNA or miRNA; wherein in the second inactive conformation, the aptamer binds the ligand and stabilizes the second inactive conformation, and the switching strand disrupts the duplex stem region via a strand-displacement mechanism to abolish processing of the duplex stem region to the siRNA or miRNA.

In certain embodiments, suitable output device includes any suitable display, such as computer monitor, any printed material, any data medium (CD, DVD, SD, memory card, hard drive, magnetic tape, etc).

In certain embodiments, in step (3):

$$K_{Comp} = \sqrt[h]{\frac{e \cdot f_{shRNA}}{C_1} \left[ C_2 + \exp\left(-\frac{\Delta G_{method}}{k_B N_A T}\right)\right]^{C_3}} - 1. \quad (5)$$

wherein:

e is the processing efficiency of the duplex stem region to siRNA or miRNA by in vivo RNAi pathway, and is calculated from the basal expression levels from several related shRNA switches differing only in the switching strand sequence and strongly preferring the first active conformation;

$f_{shRNA}$ is an experimentally obtained value of the relative knockdown of target gene expression by a corresponding shRNA having the same duplex stem region but without the aptamer and the switching strand;

$C_1$-$C_3$ are fit constants obtained from fitting $\Delta G_{method}$ and the basal expression levels for the several related shRNA switches using a least-square analysis of $$f_{fit} = 1 - C_1 \left[ C_2 + \exp\left(-\frac{\Delta G_{method}}{k_B N_A T}\right)\right]^{-C_3}, \quad (2)$$

wherein $f_{fit}$ is the basal expression of the target gene for the fit curve of Eq. (2);

$k_B$ is the Boltzmann constant;

$N_A$ is Avogadro's number;

T is temperature (in K); and, h is the Hill coefficient that accounts for non-linearity between siRNA concentration and the relative target gene expression level, and is obtained by generating a ligand response curve with one shRNA switch having negligible knockdown of the target gene expression at the highest ligand concentration, and best fitting the curve with a least-square analysis.

In certain embodiments, the predicted relationship is represented by:

$$f_{model} = \frac{1}{1 - e \cdot f_{shRNA} \left[1 + \left[\sqrt[h]{\frac{e \cdot f_{shRNA}}{C_1}\left[C_2 + \exp\left(-\frac{\Delta G_{method}}{k_B N_A T}\right)\right]^{C_3}} - 1\right]^{-h}\right]}{(1 + K_{Apt} \cdot L)} \quad (6)$$

wherein:

$K_{Apt}$ is the association constant between the ligand and the aptamer;

L is ligand concentration;

e is the processing efficiency of the duplex stem region to siRNA or miRNA by in vivo RNAi pathway, and is calculated from the basal expression levels from several related shRNA switches differing only in the switching strand sequence and strongly preferring the first active conformation;

$f_{shRNA}$ is an experimentally obtained value of the relative knockdown of target gene expression by a corresponding shRNA having the same duplex stem region but without the aptamer and the switching strand;

$C_1$-$C_3$ are fit constants obtained from fitting $\Delta G_{method}$ and the basal expression levels for the several related shRNA switches using a least-square analysis of $$f_{fit} = 1 - C_1 \left[ C_2 + \exp\left(-\frac{\Delta G_{method}}{k_B N_A T}\right)\right]^{-C_3}, \quad (2)$$

wherein $f_{fit}$ is the basal expression of the target gene for the fit curve of Eq. (2);

$k_B$ is the Boltzmann constant;

$N_A$ is Avogadro's number;

T is temperature (in K); and, h is the Hill coefficient that accounts for non-linearity between siRNA concentration and the relative target gene expression level, and is obtained by generating a ligand response curve with one shRNA switch having negligible knockdown of the target gene expression at the highest ligand concentration, and best fitting the curve with a least-square analysis.

In certain embodiments, in step (2), (i) the major stem for the first active conformation spans the entire duplex stem region, and, (ii) the major stem for the second inactive conformation includes base-pairs formed between the switching strand and nucleotides in the duplex stem region, excluding common regions in (i) and (ii).

In certain embodiments, the three-parameter curve fit of the $\Delta G_{method}$ values calculated with the stem method and the relative basal expression levels of the target gene has a coefficient of determination ($R^2$) of at least about 0.80 or 0.90.

The embodiments and practices of the present invention, other embodiments, and their features and characteristics, will be apparent from the description, figures and claims that follow, with all of the claims hereby being incorporated by this reference into this Summary.

It is contemplated that any embodiments described herein, including those only described under one of the many aspects of the invention, can be combined with any other embodiments described under any aspects of the invention whenever appropriate.

Figure 1A:
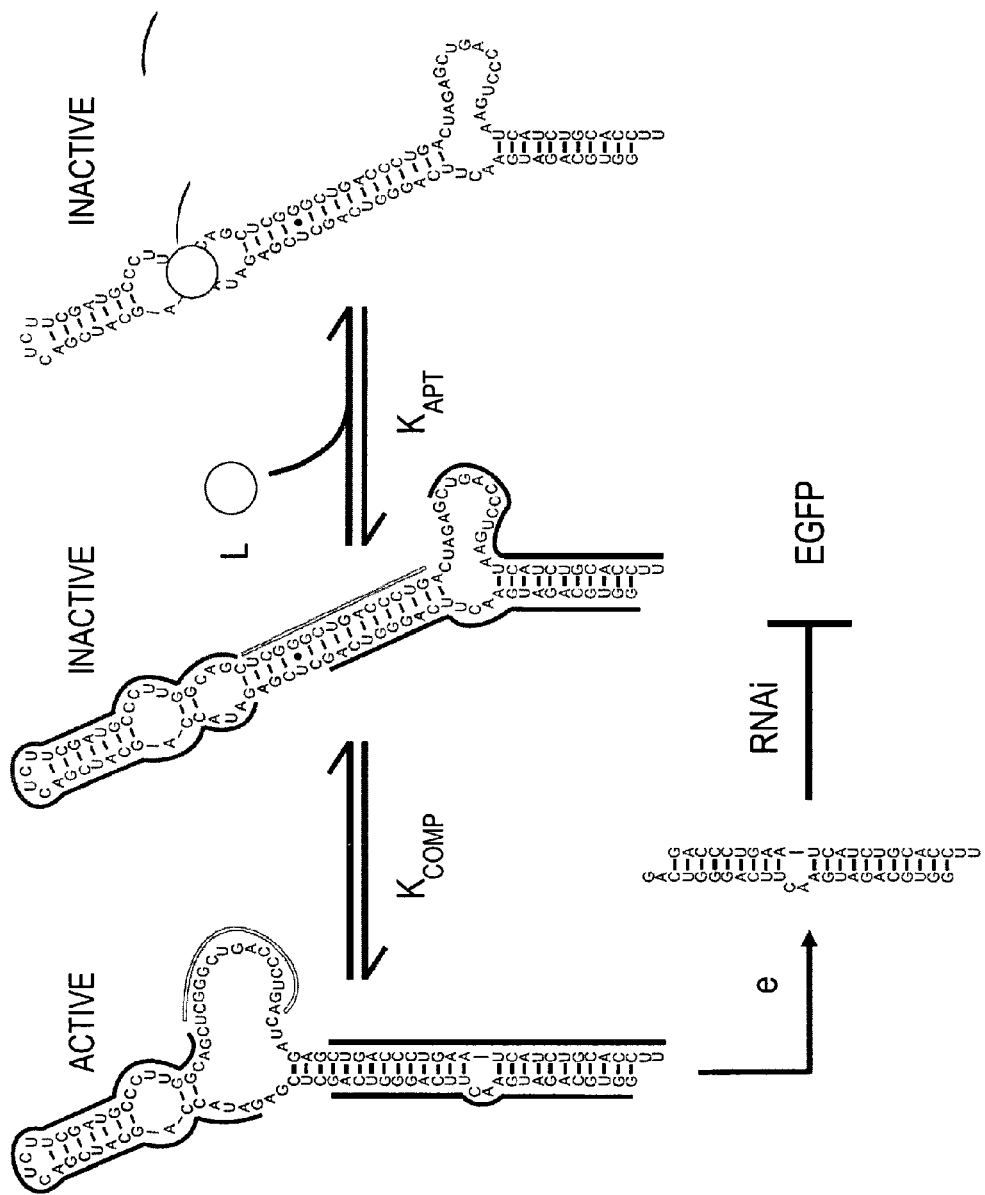
FIG. 1 shows design and characterization of an exemplary shRNA switch platform. The shRNA stem (or actuator domain, shown as the double-stranded region with a 2-nt bulge in the middle of one strand), the aptamer domain (shown as the outlined stem-loop region in the top part of the polynucleotide in FIG. 1A), and the switching strand (shown as the outlined sequence in the loop part of the polynucleotide in FIG. 1A) are outlined. The competing strand (not outlines) overlaps with part of the actuator domain in the example shown in FIG. 1A. (A) Sequence and structure of shRNA switch S1 and proposed mechanism for ligand control of RNAi-mediated gene silencing. $K_{Comp}$, $K_{Apt}$, and e are parameters from the mathematical model; L denotes ligand.

(B) In-line probing of S4t under the following theophylline concentrations (μM): 0.001, 0.01, 0.1, 1, 10, 100, 1000, and 8000. S4t was also resolved as unreacted (NR), partially digested with the G-specific RNase T1 (T1), and under basic conditions (OH). The included secondary structure of S4t is representative of the inactive conformation. Band quantification (right) is aligned with the resolved gel image. Nucleotides undergoing constant (medium gray shade), increased (light gray shade), or decreased (dark gray shade) cleavage in the presence of theophylline are shown. (C) Sequence and structure of shRNA switch S1 and associated controls. (D) Component transfer functions of S1 and switch controls. Dependence of GFP levels on theophylline concentration for HEK293T tTA-d2EGFP cells transfected with plasmids harboring the indicated constructs in the presence of varying theophylline concentrations. Median fluorescence values from flow cytometry analysis were normalized to that of untransfected cells in the same well. Error bars represent one standard deviation from duplicate transfected wells.

FIG. 2 is a model that predicts tuning of the shRNA switch transfer function through variation of identified tuning parameters. Model predictions for the effect on the component transfer function of varying $K_{Comp}$ (A), $K_{Apt}$ (B), or e (C). (D) Effect of e on the dependence of basal expression levels on $K_{Comp}$. Lines designate the minimal basal expression set by $f_{shRNA}$ (-) and the transfer function that fits the S1 theophylline-response curve from FIG. 10 (—): $K_{Comp}$=0.17, $K_{Apt}$=0.016 $\mu M^{-1}$, e=0.85, $f_{shRNA}$=0.94, and h=1.33.

FIG. 3 shows experimental validation of switching strand tuning strategies. (A) Designated strategies for physical modulation of the tuning parameters. Three strategies pertain to the switching strand (light gray) and reflect changes in $K_{Comp}$, and two strategies pertain to the aptamer domain (dark gray) and reflect changes in $K_{Apt}$ and e. (B-G) Tuned theophylline response curves as described in FIG. 1D and associated RNA sequences. Each family of curves represents iterative nucleotide modifications under a single tuning strategy within the competing strand: 3' end (B), 5' end (D), and complementarity to the shRNA stem (F). Indicated sequence variants are swapped into the equivalent box in (A), which designates the applied tuning strategy for each family of curves. Error bars represent one standard deviation from duplicate transfected wells.

FIG. 4 shows experimental validation of aptamer tuning strategies. (A) Theophylline aptamer variants swapped into the equivalent box in FIG. 3A. Dissociation constants ($K_D$) as previously reported (Zimmermann et al, 2000) are indicated for each aptamer. (B) Tuned theophylline response curves as described in FIG. 1D for shRNA switches that incorporate aptamers from (A). (C) Relationship between aptamer size and the lower limit of basal expression levels estimated by shRNA switches primarily adopting the active conformation (see Materials and Methods for Examples 1-7). HEK293T tTA-d2EGFP cells were transfected with switches containing the following aptamer: none (-), xanthine aptamer (xa), smaller theophylline aptamer ($th_S$), larger theophylline aptamer ($th_L$), or tetracycline aptamer (tc). The original shRNA targeting EGFP (sh) represents the lower theoretical limit in this cellular context. Values represent the average of at least one switch for each aptamer. (D, E) Modular replacement of aptamer imparts new ligand dependence while maintaining switch functionality. Hypoxanthine response curves were generated for shRNA switches incorporating the xanthine aptamer as described in FIG. 1D, except cells were grown in the presence of varying concentrations of hypoxanthine. Indicated sequence variants are swapped into the equivalent box in FIG. 3A. (F, G) Preservation of switching strand tuning strategies for shRNA switches containing the xanthine aptamer. Variation targeted the length of the 3' end of the switching strand. Error bars represent one standard deviation from duplicate transfected wells.

Figure 5A:
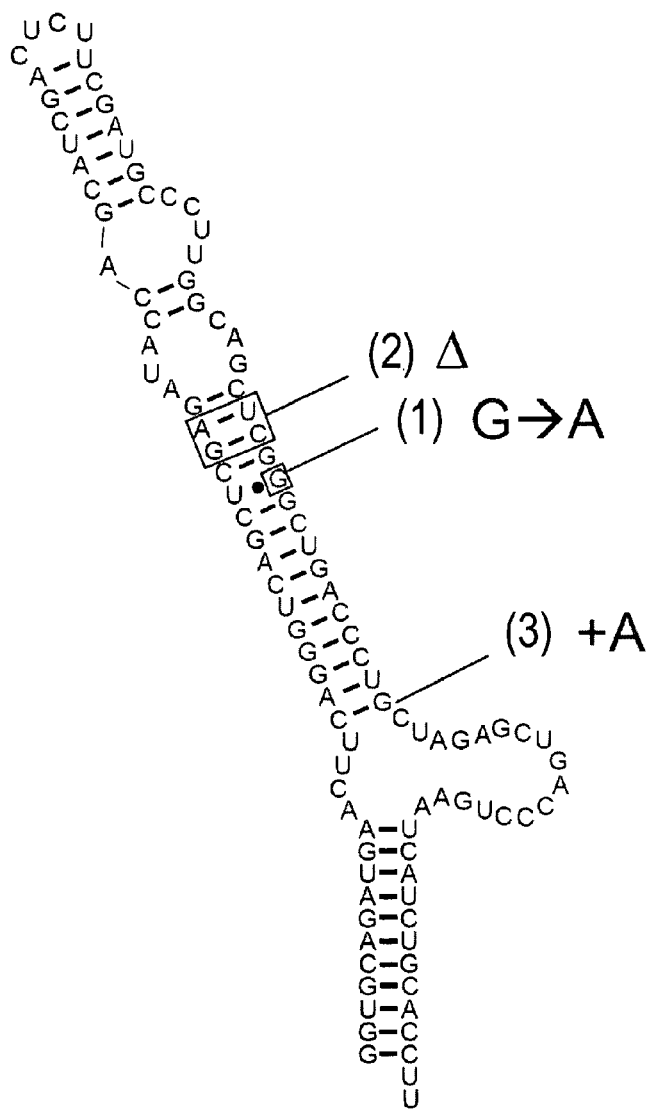
Figure 5A:
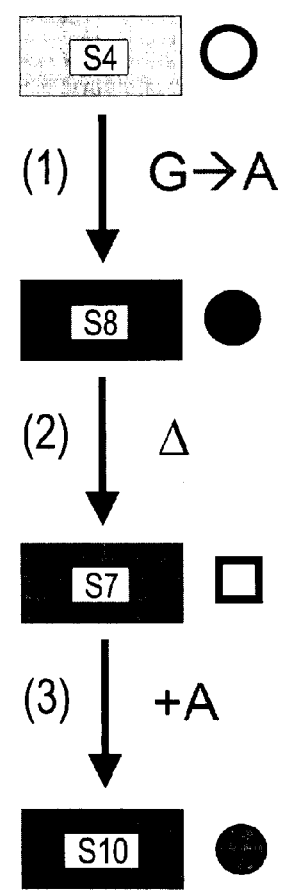
Figure 5B:
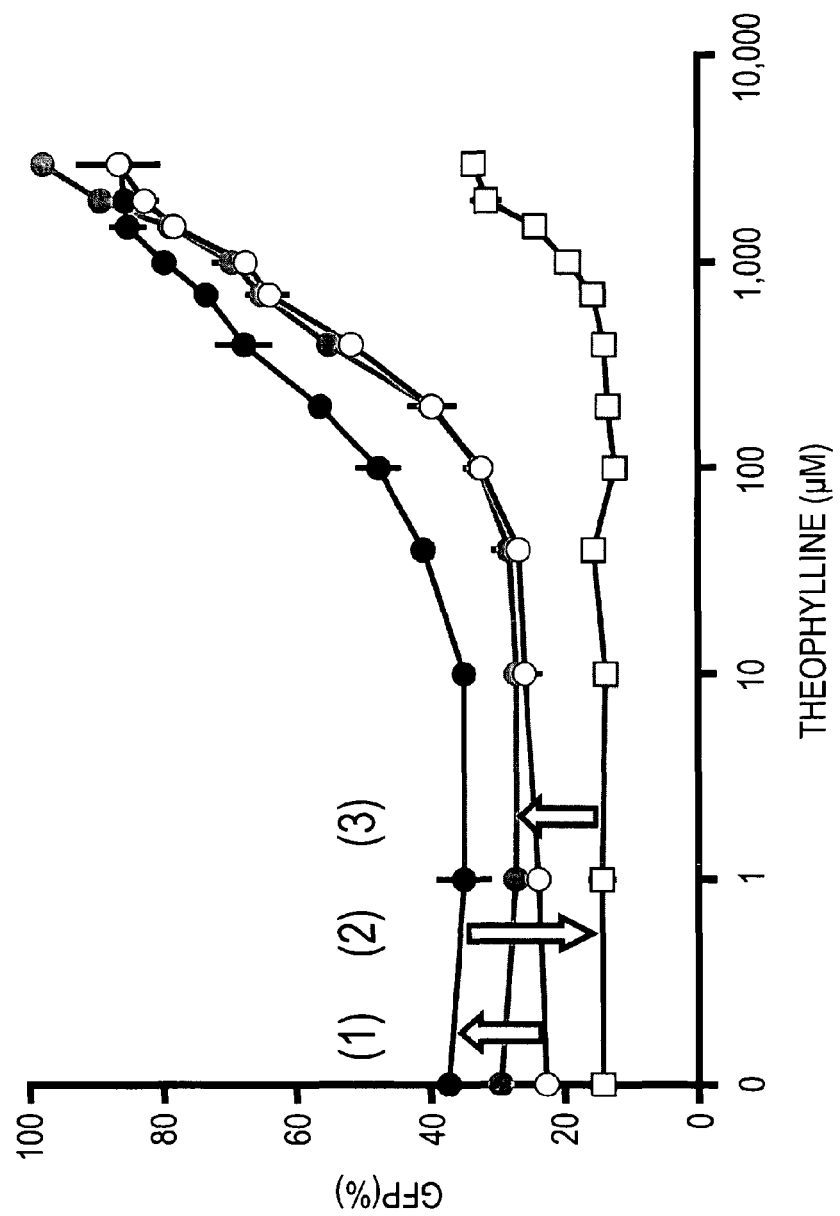

FIG. 5 shows exemplary programming of transfer functions through combinatorial design strategies. (A) Combinatorial tuning strategies enable fine tuning of the component transfer function. Step-wise nucleotide changes were made to S4, where each change fell under a different switching strand tuning strategy. (B) Tuned theophylline response curves as described in FIG. 1D. Arrows depict the systematic modifications designated in (A).

FIG. 6 is an extended model that enables sequence-to-transfer function prediction and guides the forward design of optimized shRNA switches. (A) General process to convert shRNA switch sequence information into a predicted transfer function. RNA secondary structure algorithms and the method displaying the highest correlation strength (stems method; and FIG. 11) were used to calculate the free energy difference between active and inactive conformations ($\Delta G_{method}$). This value is subsequently used to calculate $K_{Comp}$, which is inserted into the extended model to yield the predicted relationship between ligand concentration and target gene expression levels. (B) Predicted relationship between basal expression levels and calculated free energy difference ($\Delta G_{model}$) between active and inactive conformations. (C) Sequence-function relationship for shRNA switches under the stems method. This method links sequence information to basal expression levels with the aid of RNA secondary structure prediction algorithms. $\Delta G$ was calculated ($\Delta G_{method}$) according to this method for shRNA switch sequences S1-10 and plotted with the associated measured basal expression levels. The strength of the three-parameter curve fit was evaluated based on the coefficient of determination ($R^2$). Each data point represents one shRNA switch. (D) Extended model predictions for the relationship between $\Delta G_{method}$ and dynamic range ($\eta$). $\eta$ is defined as the ratio of GFP (%) at high (3 mM) and low (1 μM) theophylline concentrations. Curves represent shRNA switches containing the smaller theophylline aptamer (dark line; e=0.94, $K_{Apt}$=0.015 $\mu M^{-1}$) or the larger theophylline aptamer (light line; e=0.85, $K_{Apt}$=0.016 $\mu M^{-1}$), respectively. (E) Values of $\eta$ for shRNA switches containing the larger theophylline aptamer (S1-10; ○) or the smaller theophylline aptamer (S11-25; ■) as a function of $\Delta G_{method}$. Each data point represents one shRNA switch. S13 (the optimized shRNA switch) and S1 (the original shRNA switch) are marked. (F, G) Flow cytometry data for HEK293T tTA-d2EGFP cells transfected with S1 (F) or S13 (G) in the presence (●, filled) or absence (○) of 3 mM theophylline. Histograms from untransfected cells (□) or cells transfected with the original shRNA targeting EGFP (•) are included.

Figure 7:
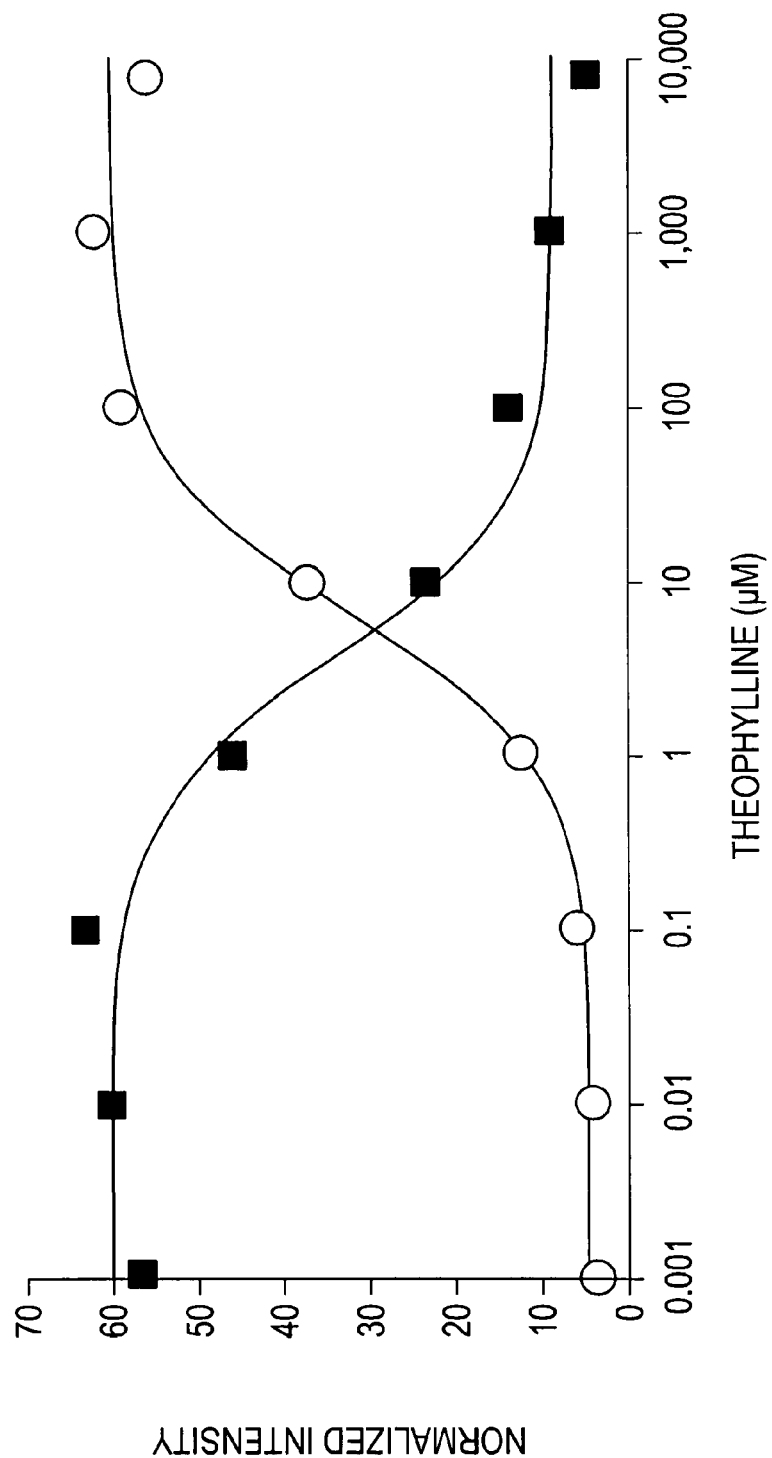

FIG. 7 shows theophylline dependence of in-line cleavage at C56 (●) and C74 (○) of S4t. Individual bands from the in-line gel (FIG. 1B) were quantified and normalized to an adjacent constant region to remove bias from inconsistent well loading. C56 bands were normalized to U47 bands, while C74 bands were normalized to U100-G102 bands. Curves were fit using a standard Michaelis-Menten model, with determined $K_D$ values of 3.6 μM and 6.8 μM for C56 and C74, respectively.

Figure 8:
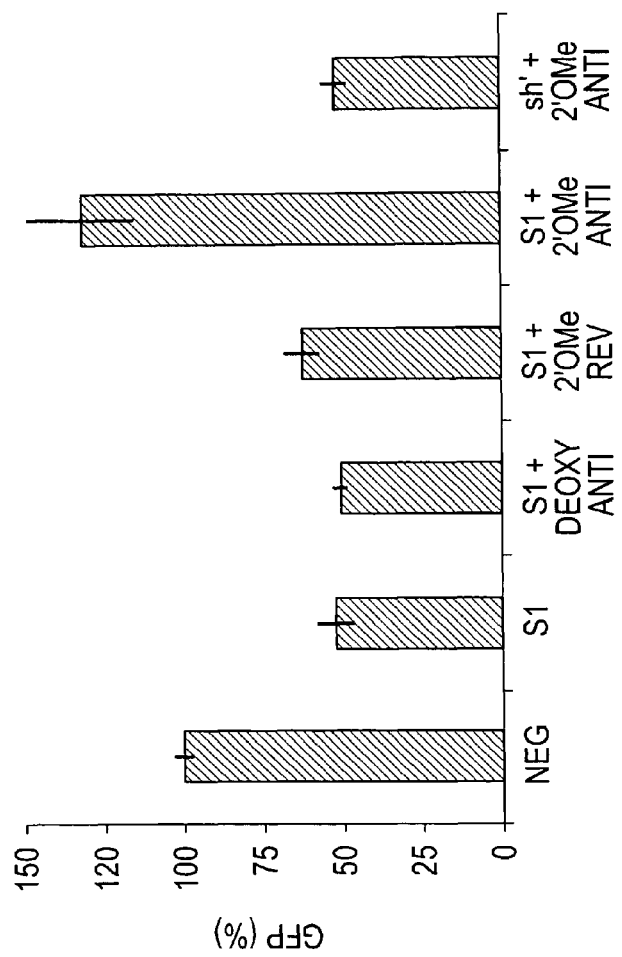

FIG. 8 shows that antisense inhibition of guide strand activity represses RNAi-mediated silencing of GFP. Cells stably expressing EGFP were cotransfected with the designated oligo and a plasmid that expresses a scrambled shRNA (neg), shRNA switch S1, or an shRNA targeting a different region of the EGFP mRNA (sh'). Mean fluorescence relative to negative based on flow cytometry measurements of transfected cells. The guide strands are "S1" and "sh'"; the 2'-O-Methyl nucleotides are "2'OMe anti" and "2'OMe rev"; and all the nucleotides except for the three 3'-end nucleotides in "deoxy anti" are deoxynucleotides. Error bars represent one standard deviation from duplicate transfected wells.

Figure 9:
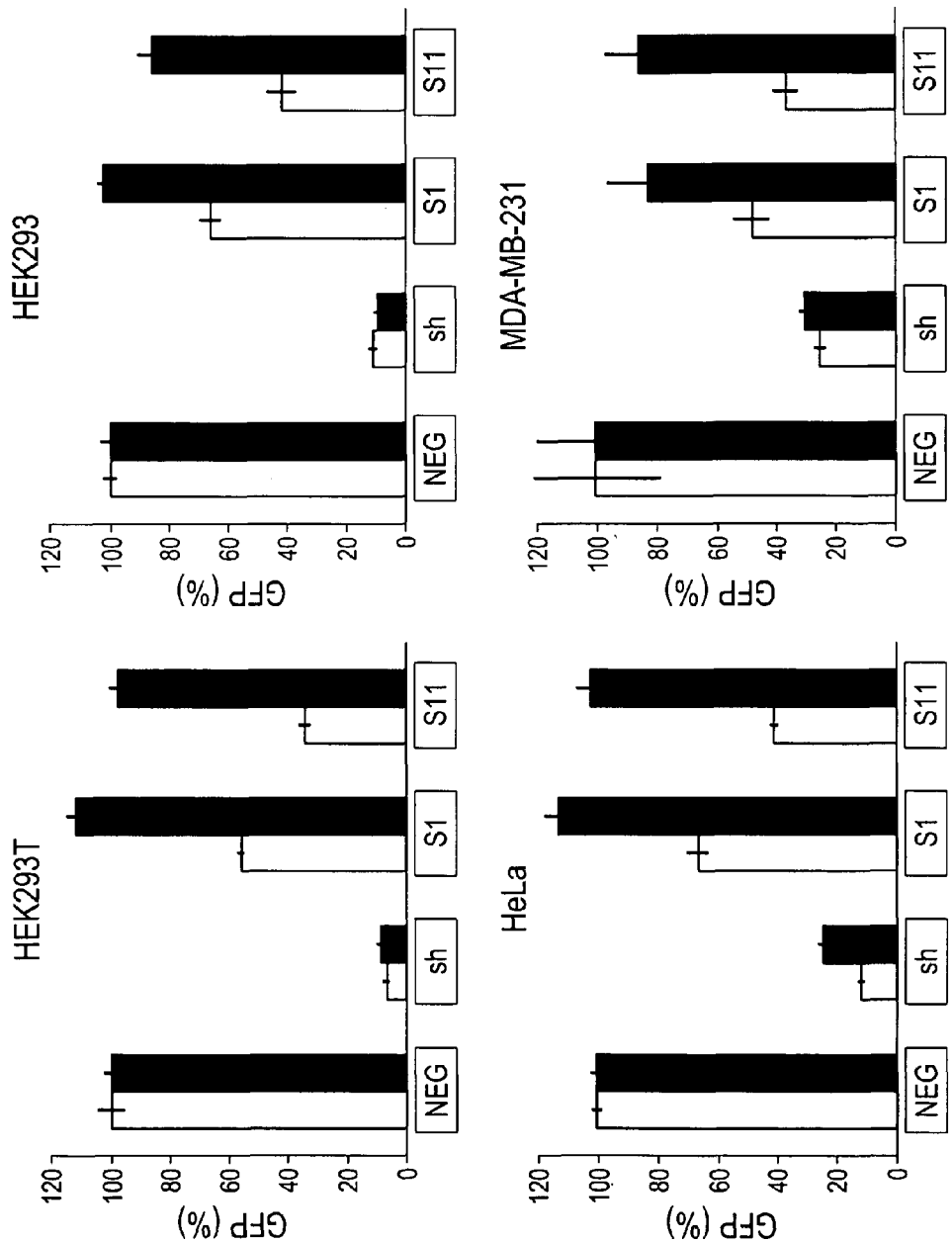

FIG. 9 shows functionality of shRNA switches in different cell lines. Cells lacking endogenous EGFP expression were cotransfected with the shRNA construct and an EGFP expression plasmid in the presence (●) or absence (□) of 3 mM theophylline. Mean fluorescence values were normalized to red fluorescence values (DsRed-Express) contributed by the shRNA construct. These values were then normalized to those of cells transfected with a scrambled shRNA (neg). Error bars represent one standard deviation from triplicate transfected wells.

Figure 10:
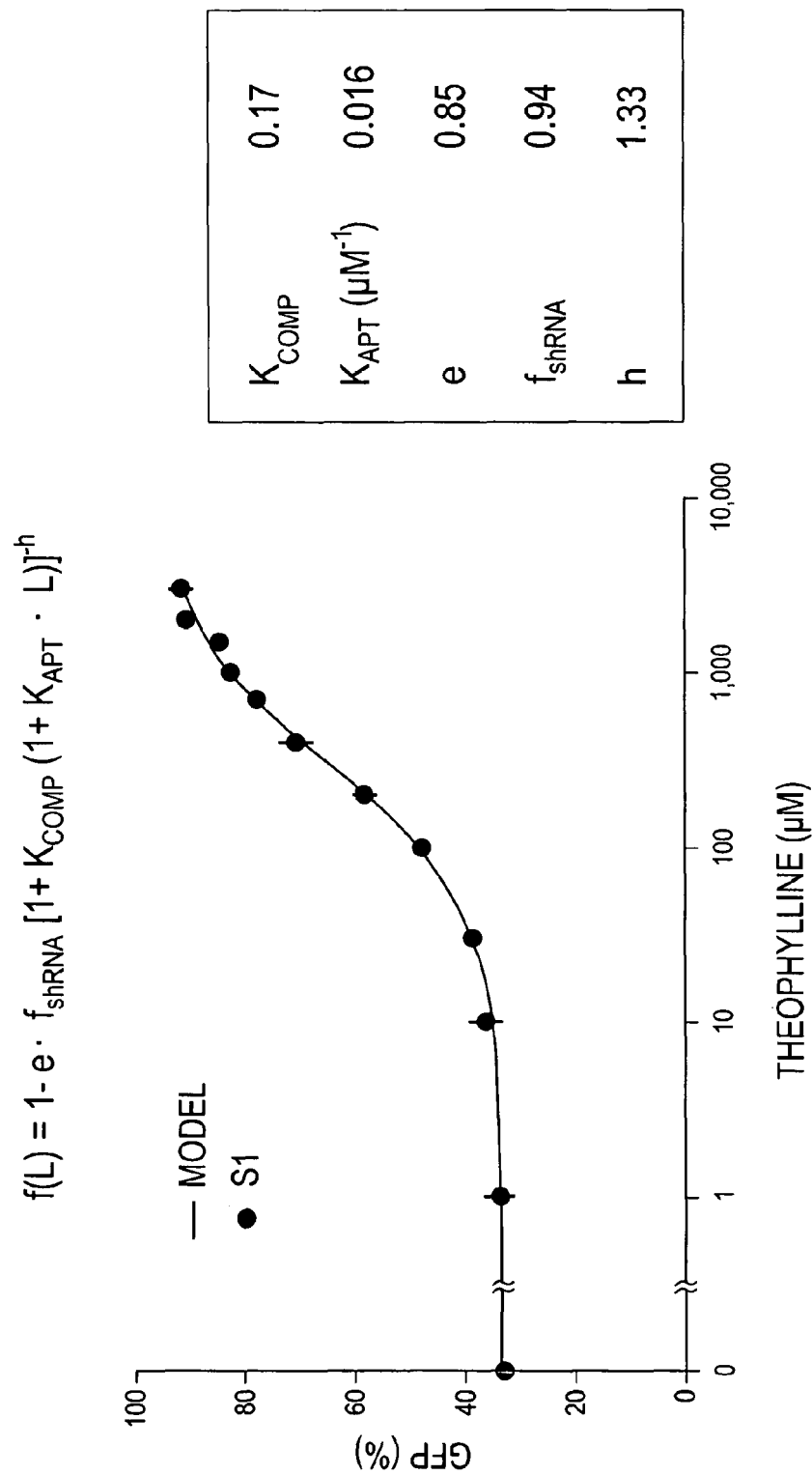

FIG. 10 shows the derived model equation and model fit of the theophylline response curve for S1 data. The value of $f_{shRNA}$ was set by a separate transfection experiment with the original shRNA targeting EGFP (sh) under the same conditions. The value of e was determined from the average basal expression levels of shRNA switches that highly favor the active conformation (S5, S7, S9, S10). Parameters $K_{Comp}$, $K_{Apt}$ and h were produced by a least-squares fit (—) to the S1 data (•). Parameter values are reported to the right of the plot.

Figure 11:
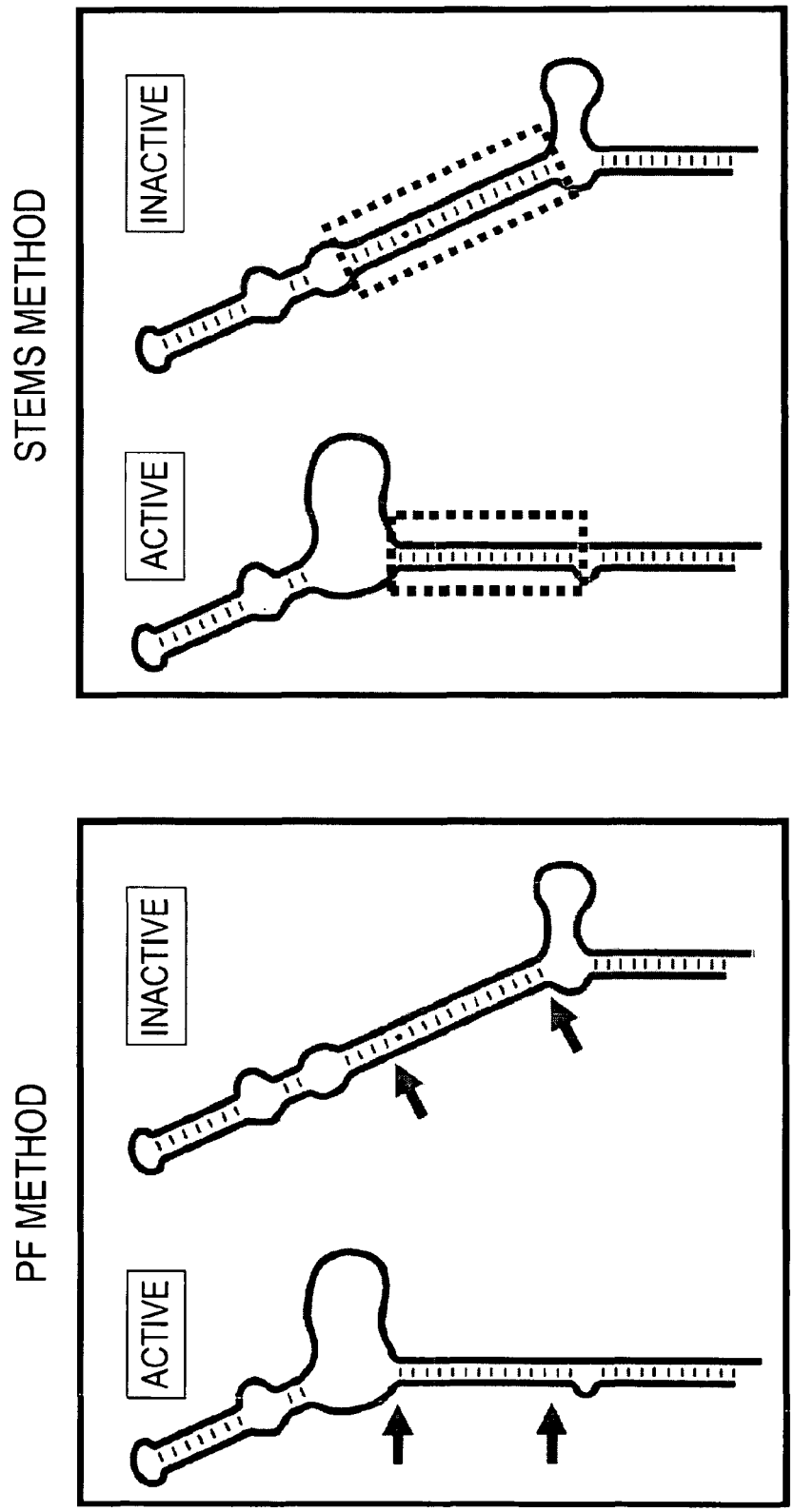

FIG. 11 depicts methods to calculate ΔG from shRNA switch sequence information. Base-pairing probabilities of base-pairs designated by arrows were used for the PF method. The boxed sections designate the major stem in the active and inactive conformations used under the Systems method.

Figure 12:
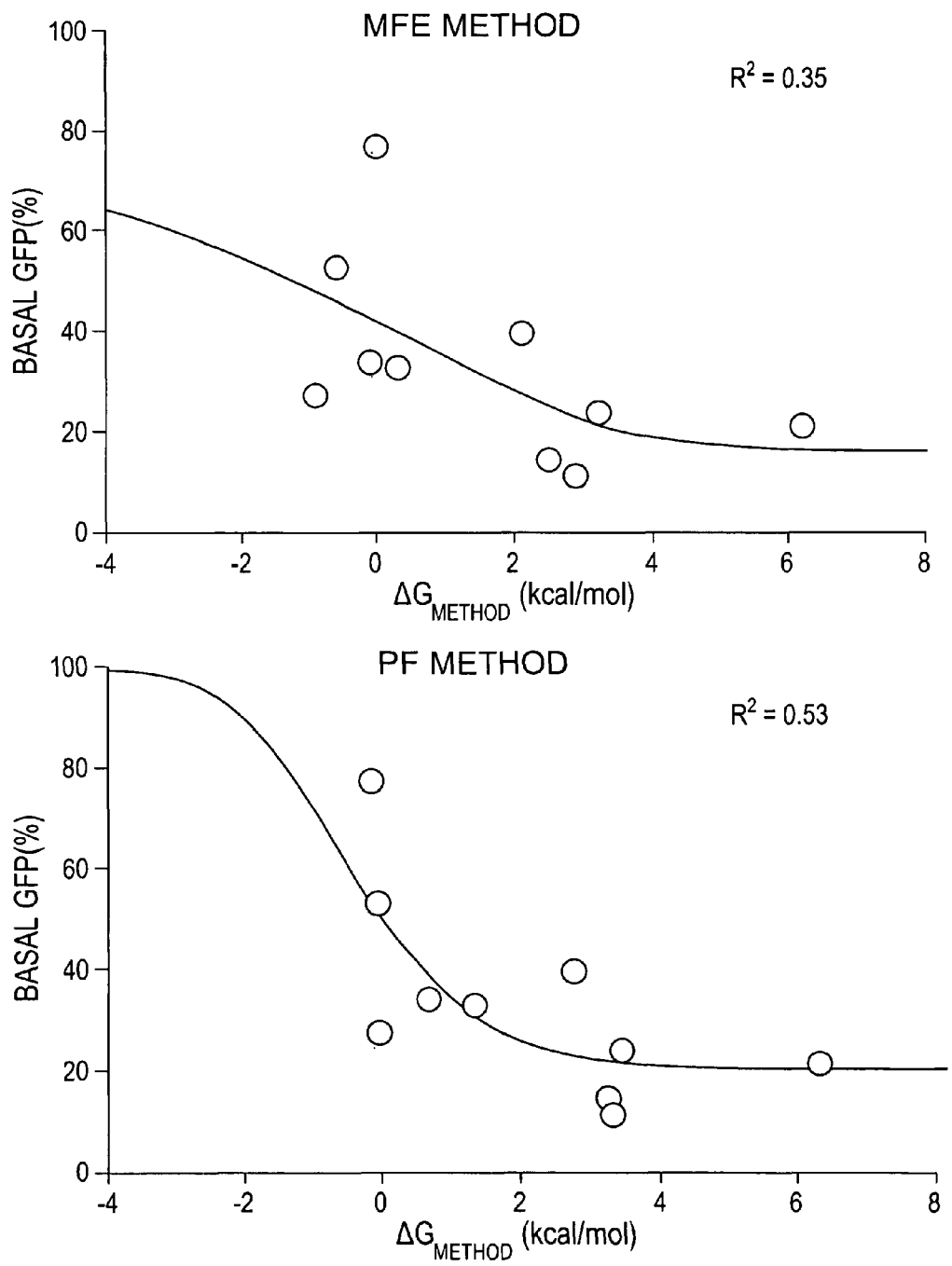

FIG. 12 shows the use of alternative methods for relating shRNA switch sequence and in vivo basal expression levels. ΔG was calculated ($\Delta G_{method}$) for shRNA switches S1-10 using RNA secondary structure prediction algorithms. Plots relating $\Delta G_{method}$ and measured basal expression level for shRNA switches S1-10, where ΔG was calculated using the MFE method or the PF method. A three-parameter equation with the same mathematical form as the model was fit by least-squares analysis to each data set.

Figure 13:
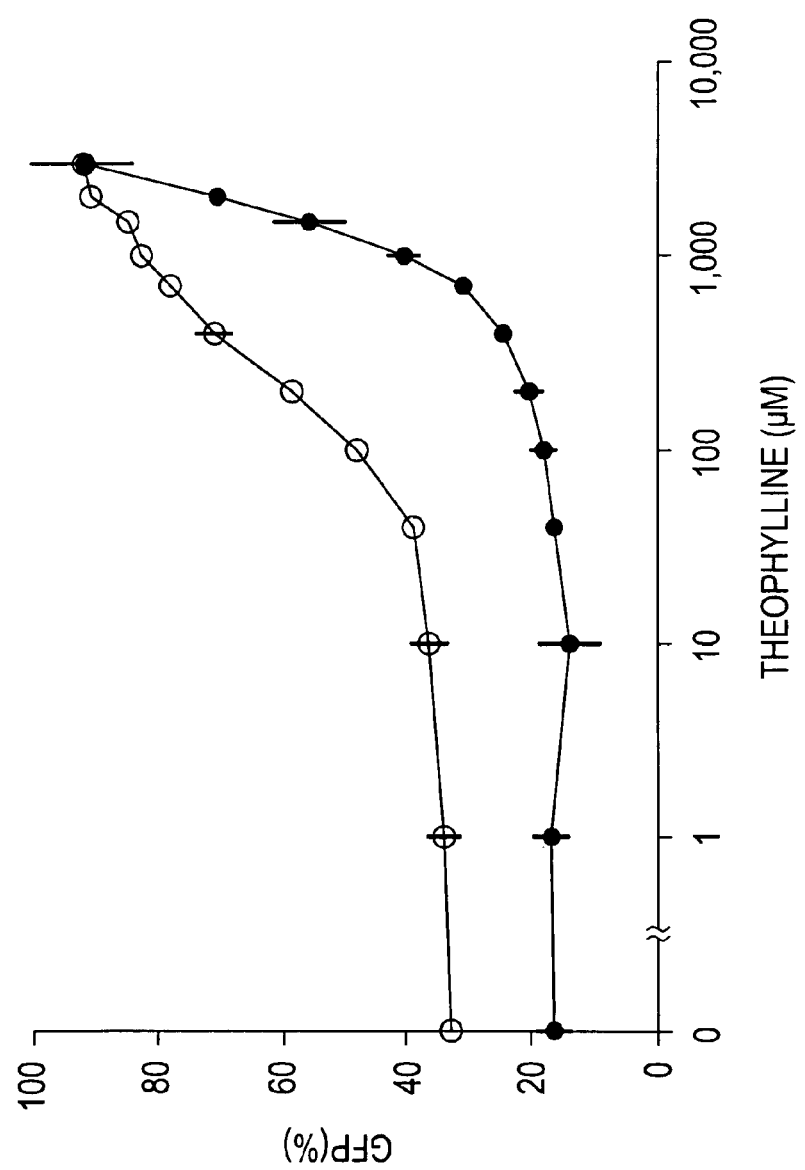
Figure 14A:
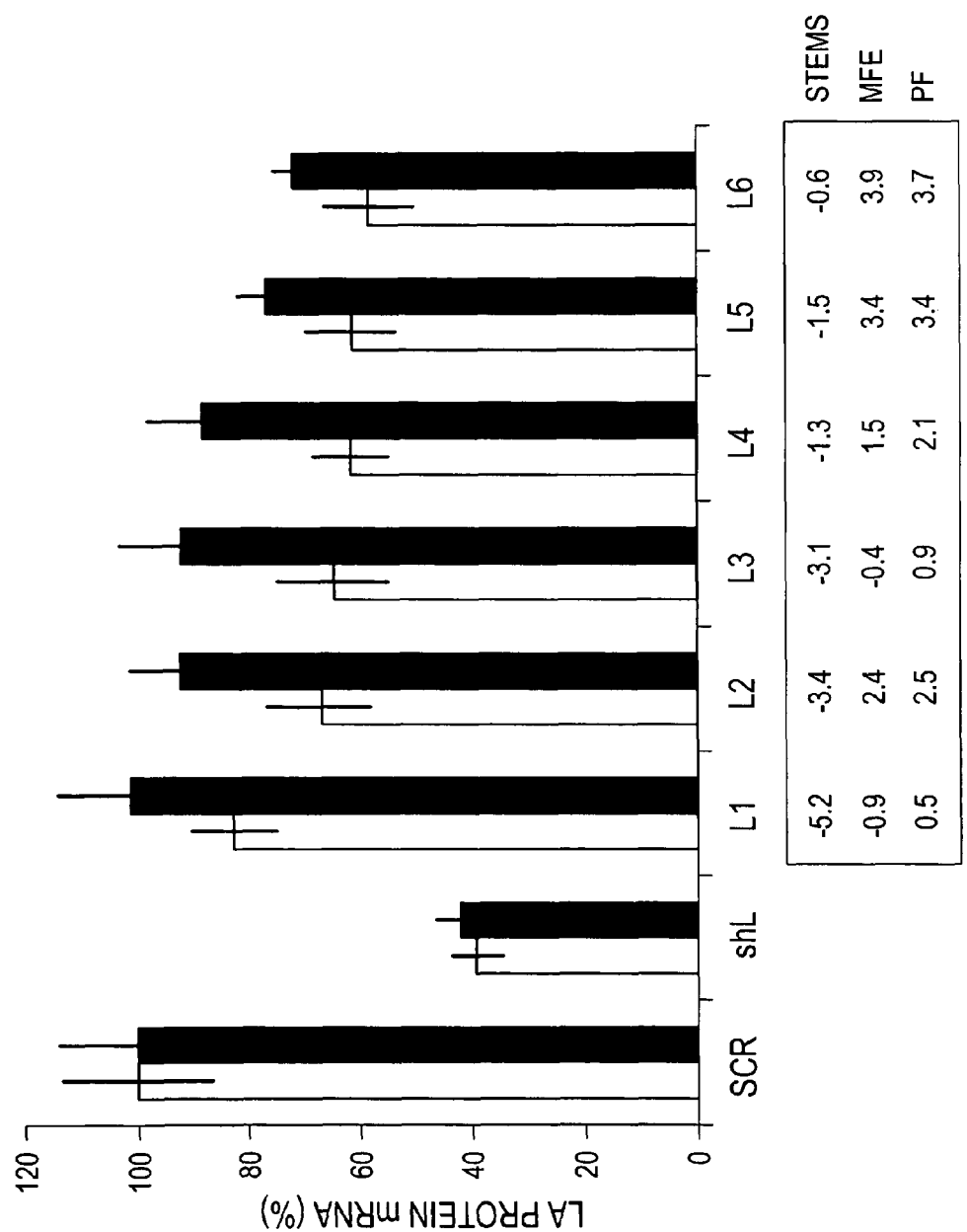
Figure 14B:
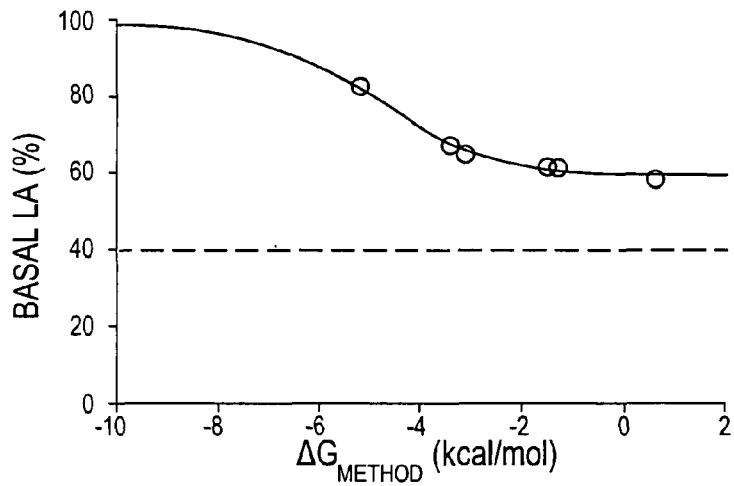
Figure 14C:
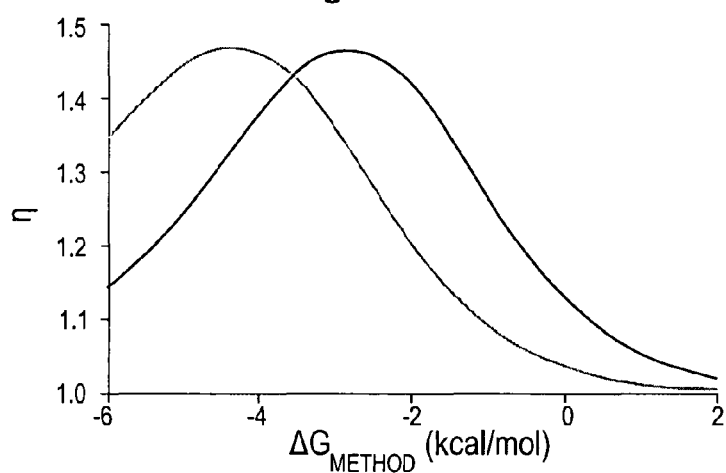
Figure 14D:
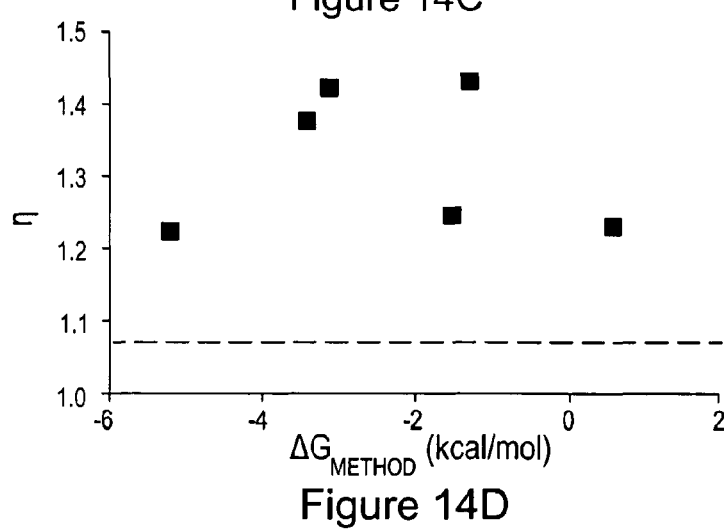

FIG. 13 shows theophylline response curves for the initial (S1, •) and optimized (S13, •) shRNA switches. Median fluorescence values from flow cytometry analysis were normalized to that of untransfected cells in the same well. Error bars represent one standard deviation from duplicate transfected wells.

FIG. 14 shows theophylline-mediated regulation of endogenous La protein with shRNA switches. (A) qRT-PCR of La protein mRNA from HEK293T tTA-d2EGFP cells transfected in the presence (●) or absence (□) of 1.5 mM theophylline. Calculated free energy differences from the stems, minimal free energy (MFE) and partition function (PF) method are displayed below each shRNA switch. Error bars represent quadruplicate qRT-PCR measurements. (B) Curve fit to extrapolate empirical parameters C1-3. Dashed line marks knockdown achieved by base shRNA. (C) Model predictions for dynamic range using empirical parameter values for the GFP experiments along with $f_{shRNA}$=0.6 and e=0.72 (gray curve) and extrapolated values from the La experiments (black curve). (D) Relationship between dynamic range (η) and the free energy difference. The dashed line represents the apparent increase in La mRNA levels upon theophylline addition observed for the base shRNA (shL).

Figure 15:
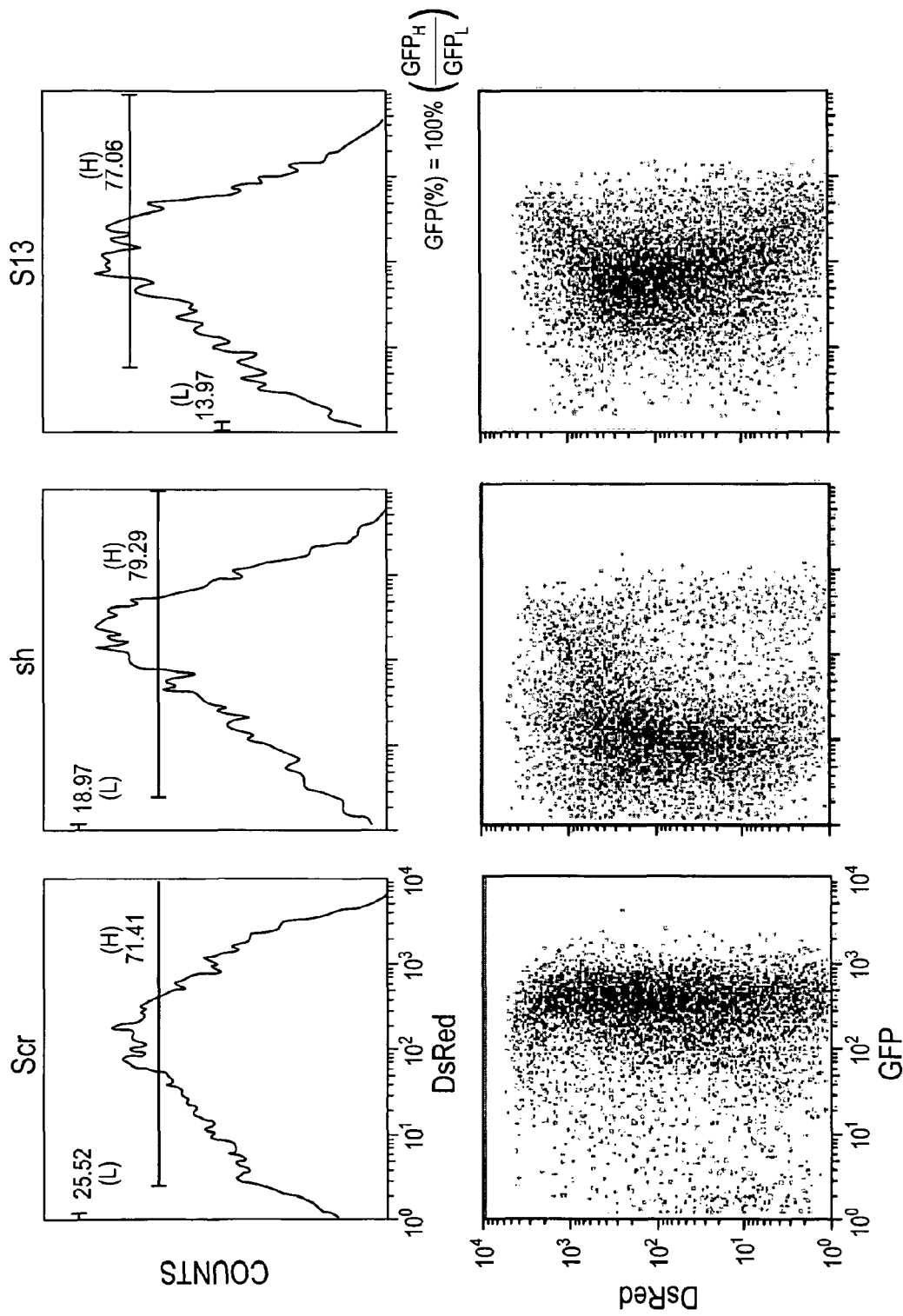

FIG. 15 shows representative histograms (top row) and dot plots (bottom row) for HEK293T tTA-d2EGFP cells transiently transfected with a plasmid expressing DsRed-Express and either a scrambled shRNA (Scr), the base shRNA targeting EGFP (sh), or shRNA switch S13. Gates in the histogram capture the transfected (H) and untransfected (L) populations in each well. The calculation of GFP (%) used in the main text is shown on the right. Median GFP levels of each transfected population were normalized to that of untransfected cells in the same well, thereby reducing well-to-well variability.

DETAILED DESCRIPTION OF THE INVENTION

1. Overview

The present invention provides a universal and extensible polynucleotide-based platform for engineering ligand-controlled gene regulatory systems that exhibit tunable regulation of gene expression, design modularity, and target specificity. The invention also provides polynucleotides engineered based on these design principles.

Specifically, the application describes a framework for the reliable de novo construction of modular, portable, and scalable control systems that can be used to achieve flexible regulatory properties, such as up- and down-regulation of target expression levels and tuning of regulatory response to fit application-specific performance requirements, thereby expanding the utility of our platforms to a broader range of applications. For example, these switch platforms may be applied to the construction of transgenic regulatory control systems that are responsive to cell permeable, exogenous molecules of interest for a given network. In regulating sets of functional proteins, these switches can act to rewire information flow through cellular networks and reprogram cellular behavior in response to changes in the cellular environment. In regulating reporter proteins, the subject regulated nucleic acids (or switches) can serve as synthetic cellular sensors to monitor temporal and spatial fluctuations in the levels of diverse input molecules. The switch platforms described here represent powerful tools for constructing ligand-controlled gene regulatory systems tailored to respond to specific effector molecules and enable regulation of target genes in various living systems. The design principles described herein enable the de novo design of such versatile switches. Due to their general applicability, our platforms offer broad utility for applications in synthetic biology, biotechnology, and health and medicine.

Thus one aspect of the invention relates to a sensor domain-regulated (e.g., aptamer-regulated) nucleic acid and methods and compositions comprising these nucleic acids for modulating (e.g., attenuating) gene expression in a cell. Another aspect relates to sensor domain-regulated (e.g., aptamer-regulated) nucleic acids that may be employed as in vivo sensors to detect the presence, absence, or amount of a molecule in a sample. For example, such nucleic acids may be used to sense changes in an intracellular condition, such as changes in ligand concentration, pH, temperature, etc. After sensing the change, an output signal from a reporter gene (such as expression of a fluorescent protein, or activity of an enzyme) may be used to monitor the changes. In certain embodiments, the sensor domain-regulated (e.g., aptamer-regulated) nucleic acid may alter the detected change in the condition through the coupled actuator domain, thus providing a feedback regulation.

The sensor domain-regulated (e.g., aptamer-regulated) nucleic acids may be either trans-acting or cis-acting. By trans-acting, it is meant that the switches of the present inventions exert their ligand-dependent activity on a molecule, e.g. another nucleic acid, that is different from the switch, e.g. not linker through a phosophodiester (or equivalent) backbone linker, and even more preferably not covalently linked to the switch at all. By cis-acting, it is meant that the switches of the present inventions exert their ligand-dependent activity on itself, or an otherwise heterologous molecule that is covalently linked to the switch, e.g., through a phosphodiester (or equivalent) backbone linker.

Thus, one aspect of the present invention provides engineered, sensor domain (aptamer) regulated nucleic acids that are powerful, allosteric regulators of gene expression. A general design of such nucleic acids is based on conformational dynamics of nucleic acid folding to create a modular molecule comprising a modular actuator domain, a modular sensor (aptamer) domain, and an information transmission domain (ITD) that functionally couples the actuator domain and the sensor (aptamer) domain such that the latter two domains can remain truly modular (see definition below). In contrast to the strand-slippage mechanism (see definition below) based information transmission domain, the ITD of the subject invention is based on the strand-displacement mechanism (see definition below) that is amenable to rational design. Such a strand-displacement mechanism uses competitive binding of two nucleic acid sequences (e.g., the competing strand and the switching strand) to a general transmission region of the switch (e.g., the base stem of the aptamer) to result in disruption or restoration of the actuator domain in response to restoration of the sensor domain.

A further feature of the subject information transmission domain is that the switching strand and the competing strand of the ITD are in a continuous strand of sequence (e.g., the switching strand may be within a loop structure in at least one conformation of the sensor domain-regulated nucleic acid, and does not have a free 5'-OH or 3'-OH group). This design feature eliminates any free-floating ends of the switching strand and/or the competing strand and localizes the competitive hybridization event to two strands that are continuous/linked, thereby improving the kinetics of strand-displacement.

The subject sensor domain-regulated nucleic acids are preferably designed such that it can adopt at least two distinct conformations. In one conformation, the sensor domain is capable of binding to a ligand, and the actuator domain may resume one activity state (e.g., more active state or less active state). In the other conformation, the sensor domain is incapable of binding to the ligand, and the actuator domain may resume another activity state. The conformation change of the sensor domain may be transmitted through the information transmission domain to the coupled actuator domain, so that the actuator domain adopts one of the two activity states depending on whether the sensor domain can or cannot bind the ligand.

While not wishing to be bound by any particular theory, the molecule distributes between two conformations, partly based on the free energy differences between the two conformations. Ligand binding to one of the two conformations provides additional stability to the complex, thus shifting the distribution towards the conformation capable of ligand-binding, and thus favoring the active state of the actuator domain associated with the ligand-binding sensor domain. Thus at the macro level, it appears that ligand-binding has caused a conformation change from one conformation to the other, and "conformation change" may be used herein to describe the ligand binding-induced shift in partitioning between the two conformations.

The subject regulated nucleic acid platform is flexible, enabling both positive and negative regulation as a function of ligand concentration. For example, the ligand-bound sensor domain may be associated with the more active form of the actuator domain, or with the less active form of the actuator domain.

The switching dynamics of aptamer-regulated nucleic acids are amenable to tuning by forward engineering design strategies based on thermodynamic properties of nucleic acids. Altering the free energy of the actuator domain and/or the sensor domain alters the conformational dynamics of these molecules in a predictable fashion. Specifically, decreasing the stability of the actuator domain associated with one activity state (by, for example, reducing the length of perfectly matched base pairs in a stem structure within the actuator domain, or lower the quality of base-pairing) may favor a shift in partitioning between the two conformations to the other activity state of the actuator domain (and its associated sensor domain conformation), thus increasing or decreasing the ligand concentration necessary to induce the equilibrium shift between the two conformations. This may also change the dynamic range of the switch in addition to ligand concentration dependence). On the other hand, changing the size of the sensor domain does not necessarily alter the conformational change between the two conformations, but may change the efficiency with which the switch is processed (by RNase III, for example, when the actuator domain is a Dicer substrate). Likewise, changing the affinity of the sensor (aptamer) domain for the ligand provides yet another fine tuning strategy for the subject sensor-regulated polynucleotides. These fine tuning strategies may be used in combination to provide flexible yet predictable changes in activity of the subject sensor domain-regulated nucleic acids in response to different ligand concentrations or environmental condition changes.

In addition, the aptamer-regulated nucleic acid platform is fully modular, enabling ligand response and actuator function (e.g., transcript targeting) to be engineered by swapping domains within the subject regulated nucleic acid. This provides a platform for the construction of tailor-made sensor domain regulated nucleic acids for a variety of different ligands. Ligand binding of the aptamer domain in aptamer-regulated nucleic acids is designed separately from the targeting capability of the actuator domain by swapping only the aptamer domain. Likewise, the targeting capability of the actuator domain can be designed separately from the ligand binding of the aptamer domain by swapping the effector domain so that a different gene or molecule is targeted without affecting the aptamer domain. This feature is made possible by the unique property of the subject information transmission domain that employs the strand displacement mechanism. Thus, the subject sensor domain-regulated nucleic acids present a powerful, flexible method of tailoring spatial and temporal gene expression in both natural and engineered contexts.

The subject sensor domain-regulated nucleic acids are novel, allosteric regulators of gene expression that can potentially function across a diverse range of organisms, from prokaryotes to humans, making them extremely useful in many different applications. For example, the subject regulated nucleic acids presents a powerful tool for gene therapy applications, where one would like to target specific transcripts in response to specific cellular environments that are indicative of a diseased state (Watkins et al., *Curr Opin Mol Ther* 4, 224-8 (2002)). As emerging technologies enable the metabolic profiling of disease states (Koch, *J Biol Chem* 219, 181-8 (1956)), aptamer-regulated nucleic acids can be designed to respond to various metabolic markers, or a specific concentration range of a metabolic marker, partly owning to the susceptibility of the subject sensor domain-regulated nucleic acids to the various fine-tuning strategies. For instance, aptamer-regulated nucleic acids can be constructed to inhibit genes necessary for cell growth and division in response to oncogenic proteins or isoforms. One can also anticipate an exogenously delivered aptamer-regulated nucleic acid comprising an actuator domain that is an antisense construct or RNase III substrate acting as a therapeutic molecule, similar to exogenously delivered antisense oligonucleotides or RNAi therapeutic agents, thereby extending the functionality of current antisense/RNAi therapies by introducing ligand-specific or cell type-specific action to an already highly targeted therapy.

The subject regulated nucleic acids can further be used to engineer novel regulatory pathways and control loops for applications in metabolic engineering (Khosla et al., *Nat Rev Drug Discov* 2, 1019-25 (2003)) and synthetic circuit design (Kobayashi et al., *Proc Natl Acad Sci USA* 101, 8414-9 (2004)) by enabling the cell to sense and respond to intracellular metabolite levels and environmental signals. Because the regulated nucleic acids activity is tunable over a range of ligand concentrations, switches can be designed to inhibit or activate genes only when certain metabolites exceed or go below certain concentrations. Balancing heterologous gene expression in biosynthetic pathways (Berens et al., *Bioorg Med Chem* 9, 2549-56 (2001)) to maximize product yield can be achieved with aptamer-regulated nucleic acids that regulate expression of biosynthetic genes in response to pathway intermediate levels. Synthetic gene circuits have recently been used to understand and model cellular networks (Nagai et al., *Nat Biotechnol* 20, 87-90 (2002)) and to achieve cellular control as a step towards "programmable" cell behavior (Watkins et al., *Curr Opin Mol Ther* 4, 224-8 (2002)). Gene circuits can be built using combinations of aptamer-regulated nucleic acids as regulators for precise control schemes. Aptamer-regulated nucleic acids will be useful tools in building and characterizing circuits that accurately model natural regulatory pathways and yield further insight into these prevalent regulation schemes.

Finally, sensor domain-regulated nucleic acids present new tools for cellular imaging, measuring, and detection strategies enabling programmable concentration-specific detection of intracellular molecules. Such nucleic acids offer a unique platform to create tailor-made cellular sensors and "smart" regulators that potentially can target any gene in response to any target ligand, creating new avenues for cellular control and engineering.

2. Definitions

"Actuator domain" refers to a switch domain that encodes the system control function. In certain embodiments, the actuator domain encodes the gene-regulatory function, and the actuator domain is not a ribozyme, such as a hammerhead ribozyme.

As used herein, a "bulge" is a sequence of nucleotides that is not paired with another strand and is flanked on both sides by double-stranded nucleic acid sequences. In certain embodiments, a bulge is located within a stem. When a bulge is located within a stem, the nucleotides of the bulge are considered to be part of the stem. In certain embodiments, a stem may comprise more than one bulge. In certain embodiments, one or both strands of the stem contain a bulge.

"Communication module" refers to a sequence element that typically forms an imperfectly paired double-stranded stem that can adopt different base pairs between nucleotides through a "slip-structure" mechanism. A communication module may be a type of information transmission domain that transmits the binding state of the aptamer domain to the adjacent actuator domain through a helix-slipping mechanism. A communication module does not generally act in a modular fashion with other switch domains.

"Competing strand" refers to the nucleic acid sequence within a strand-displacement domain that is bound to the general transmission region of the switch when the sensor domain is in one conformation, such as the restored conformation (i.e., in the presence of ligand in this hypothetical situation). The competing strand competes for binding with the switching strand, which is initially bound to this transmission region (for example, in the absence of ligand).

"Complementary" refers to a nucleotide or nucleotide sequence that hybridizes to a given nucleotide or nucleotide sequence. For instance, for DNA, the nucleotide A is complementary to T, and vice versa, and the nucleotide C is complementary to G, and vice versa. For instance, in RNA, the nucleotide A is complementary to the nucleotide U, and vice versa, and the nucleotide C is complementary to the nucleotide G, and vice versa. Complementary nucleotides include those that undergo Watson and Crick base pairing and those that base pair in alternative modes. For instance, as used herein for RNA, the nucleotide G is complementary to the nucleotide U and vice versa, and the nucleotide A is complementary to the nucleotide G and vice versa. Therefore, in an RNA molecule, the complementary base pairs are A and U, G and C, G and U, and A and G. Other combinations, e.g., A and C, A and A, G and G, or C and U, are considered to be non-complementary base pairs.

Due to the binding energy differences between different base pairs, the "quality of complementarity" also varies, and may be explored to fine tune the free energy differences between different conformations of the subject regulated polynucleotides. For example, the G-C base pair exhibits the highest binding affinity, and thus is said to have a higher quality of binding than that of an A-T or A-U pair, or a G-U pair, etc. Depending on specific needs, a Watson-Crick base pair may be replace by another (stronger or weaker) Watson-Crick base pair, or a wobble base pair to alter the quality of complementarity of any region in the subject regulated nucleic acid.

A "complementary sequence" comprises individual nucleotides that are complementary to the individual nucleotides of a given sequence, where the complementary nucleotides are ordered such that they will pair sequentially with the nucleotides of the given sequence. Such a complementary sequence is said to be the "complement" of the given sequence. For example, complements of the given sequence, 5'-ACUAGUC-3', include 3'-UGAUCAG-5' and 3'-UGGACGG-3', among others. In the latter sequence, the third and sixth base pairs are both non-Watson and Crick G/U complementary base pairs.

"Component" is a part of a system that encodes a distinct activity or function.

"Composability" refers to a property of a system that indicates its ability to be comprised of components that can be selected and assembled in a modular fashion to achieve a desired system performance. For example, in certain embodiments, composability refers to the ability of the individual domains of the control system to be modularly linked without disrupting their activities.

"Do/does not bind" as used herein to describe aptamer-ligand binding, does not mean that there is absolutely no binding at all. Compared to an aptamer that does bind the ligand (a "binding aptamer"), the $K_{Apt}$ (association constant for binding between ligand and aptamer) for the aptamer that "does not bind" the ligand is at least about 10-fold, 100-fold, 1000-fold or more larger than that of the binding aptamer, and thus its binding affinity for the ligand is at least about 10-fold, 100-fold, 1000-fold or more weaker than that of the binding aptamer.

"Engineering design principle" refers to a required property of a constructed system that enables use by others.

"Framework" refers to a basic conceptual structure that is used to solve a complex product design issue. As used here, the framework is used to reliably design and construct specific instances of RNA switches. The conceptual structure of the subject framework comprises specified engineering design principles and design strategies that enable extensible and reusable system design.

"Helix-slipping domain" refers to a subset of information transmission domains that act through a helix-slipping mechanism. The helix-slipping domain is also referred to as the communication module.

"Helix-slipping mechanism" refers to an information transmission mechanism that is based on an information transmission domain that functions through a helix-slipping event and does not allow for rational design. Such a helix-slipping event uses a communication module (or helix-slipping domain) within the general transmission region of the switch (e.g., the base stem of the aptamer) to result in disruption or restoration of the actuator domain in response to restoration of the sensor domain.

"Information transmission domain" refers to a switch domain that encodes the function of transmitting information between the sensor domain and the actuator domain.

"Information transmission mechanism" refers to a general mechanism for transmitting information between the sensor domain and the actuator domain of a switch. In certain embodiments, this mechanism regulates the activity of the actuator domain in response to the binding state of the sensor domain.

"Loop" refers to a sequence of nucleotides that is not paired with another strand. In certain embodiments, a loop is between 1 to 20 nucleotides long, 2-10 nucleotides long, or 3-8 nucleotides long.

"Modular" refers to a property of a system composed of modules that indicates whether the modules can by interchanged as parts without changing the interface between modules or the modules themselves.

"Module" refers to a self-contained system component that has a well defined interface with other system components.

"Nucleotide" refers to naturally- and non-naturally-occurring nucleotides and nucleotide analogs. Nucleotides include, but are not limited to, adenosine, cytosine, guanosine, thymidine, uracil, 4-acetylcytosine, 8-hydroxy-N6-methyladenosine, aziridinyl-cytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine and 2,6-diaminopurine.

"Nucleic acid," "nucleic acid sequence," "nucleic acid molecule," and "polynucleotide" refer to a DNA sequence or analog thereof, or an RNA sequence or analog thereof. Nucleic acids are formed from nucleotides, including, but not limited to, the nucleotides listed above.

"Platform" refers to a general framework on which specific applications can be implemented. In certain embodiments, the platform enables specific instances of switches to be built in a standardized manner.

"Portability" refers to a property of a system that indicates its ability to be implemented in environments different from that in which it was originally designed. In certain embodiments, portability refers to the ability of the control system to be implemented in different organisms.

"Reliability" refers to a property of a system that indicates its ability to perform and maintain its functions under a set of specified conditions. In certain embodiments, reliability refers to the ability of the information transmission domain to standardize the transmission of information between the sensor and actuator domains.

"Scalability" refers to a property of a system that indicates its ability to handle increasing work. In certain embodiments, scalability refers to the ability of the control system to be implemented across broad application space by being able to forward design its response to different molecular information.

A "stem" is a double-stranded nucleic acid motif formed by inter- or intra-molecular base pairing, which may or may not include mismatched base pairs or "bulges." In certain embodiments, a stem comprises 2 to about 40, or 2 to about 20 complementary base pairs. In certain embodiments, a stem comprises 3, 4, 5, 6, 7, 8, 9, 10, 11, 12, 13, 14, 15, 16, 17, 18, 19, 20, or 21 complementary base pairs.

In certain embodiments, at least 30% of the nucleotides in a stem are part of a complementary base pair. The remaining base pairs may be mismatched, non-complementary base pairs, or may be part of a bulge. In certain embodiments, at least 40%, 50%, 60%, 70%, 80%, 90%, 95%, 99%, or 100% of the nucleotides in the stem are part of a complementary base pair.

"Switch" refers to a molecule that can adopt at least two different conformational states, where each state is associated with a different activity of the molecule. Often a ligand can bind to one or more conformations of the switch, such that the presence of the ligand shifts the distribution or equilibrium across the adoptable conformations and therefore regulates the activity of the switch molecule. In certain embodiments, switch refers to an RNA molecule that can adopt different structures that correspond to different gene regulatory activities. An RNA switch is an exemplary embodiment of the subject ligand-controlled gene-regulatory system.

"Switch domain" refers to a component of a switch that encodes a distinct activity or function.

"Switching strand" refers to the nucleic acid sequence within a strand displacement domain that is bound to the general transmission region of the switch when the sensor domain is, for example, in the disrupted conformation (i.e., in the absence of ligand in this hypothetical situation). The switching strand is displaced by the competing strand in, for example, the presence of ligand (in this hypothetical situation).

"Sensor domain" refers to a switch domain that encodes a ligand-binding function. In certain embodiments, the sensor domain comprises an RNA aptamer sequence.

"Strand-displacement domain" refers to a subset of information transmission domains that act through a strand-displacement mechanism.

"Strand-displacement mechanism" refers to an information transmission mechanism that is based on the rational design of an information transmission domain that functions through a strand-displacement event. Such a strand-displacement event uses competitive binding of two nucleic acid sequences (e.g., the competing strand and the switching strand) to a general transmission region of the switch (e.g., the base stem of the aptamer) to result in disruption or restoration of the actuator domain in response to restoration of the sensor domain.

"Universal" refers to a system property that indicates its ability to maintain function across different applications, environments, and component interfaces. In certain embodiments, a universal system is composed of the five engineering design principles (scalability, portability, utility, composability, and reliability) and results in the specified extensible platform for RNA switch construction.

"Utility" refers to a property of a system that indicates its ability to be of practical use. In certain embodiments, utility refers to the ability of the control system to interface with different functional level components to enable forward design of the function that is being controlled by the system.

Other terms used herein and in the claims adopt their plain meanings as would have been understood by one of skill in the relevant art, that are not inconsistent with the usages in the instant specification.

3. Sensor-Regulated Polynucleotides

The sensor-regulated polynucleotides of the invention comprise a modular actuator domain, a modular sensor domain, and an information transmission domain. Such polynucleotides may comprise DNA or RNA, or a combination thereof. The polynucleotides may also be single-stranded or double-stranded. The single-stranded polynucleotide may comprise one or more double-stranded regions (or stems) due to intramolecular interaction (e.g., RNA secondary structure). If one or more phosphodiester linkage between the nucleotides are broken, the folded polynucleotide may in fact be double-stranded while maintaining substantially the same secondary structure.

The sensor-regulated polynucleotides may further comprise a functional group or a functional agent, e.g., an intercalator or an alkylating agent. The sensor-regulated polynucleotides may comprise synthetic or non-natural nucleotides and analogs (e.g., 6-mercaptopurine, 5-fluorouracil, 5-iodo-2'-deoxyuridine and 6-thioguanine) or may include modified nucleic acids. Exemplary modifications include cytosine exocyclic amines, substitution of 5-bromouracil, backbone modifications, methylations, and unusual base-pairing combinations. Additional analogs include at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

The sensor-regulated polynucleotides may also include labels, such as fluorescent, radioactive, chemical, or enzymatic labels.

In certain preferred embodiments, the modular sensor domain comprises an aptamer that responds to ligand binding to favors an allosteric change in the modular actuator domain, and alters the ability of the actuator domain to interact with its target molecule. Ligand binding, therefore, switches the actuator domain from "off" to "on," or vice versa. The sensor-regulated polynucleotides, therefore, act as a switch whose activity is turned "off" and "on" in response to ligand binding.

The response of the sensor (aptamer) domain to the ligand may also depend on the ligand identity and/or the amount or concentration of ligand exposed to the sensor (aptamer) domain. For example, an aptamer may bind small molecules, such as drugs, metabolites, intermediates, cofactors, transition state analogs, ions, metals, nucleic acids, and toxins. Alternatively, an aptamer may bind natural and synthetic polymers, including proteins, peptides, nucleic acids, polysaccharides, glycoproteins, hormones, receptors and cell surfaces such as cell walls and cell membranes.

In certain other embodiments, the sensor domain of the subject ligand controlled, sensor-regulated polynucleotide is responsive to environmental changes. Environmental changes include, but are not limited to changes in pH, temperature, osmolarity, or salt concentration.

Aptamers

An "aptamer" may be a nucleic acid molecule, such as RNA or DNA that is capable of binding to a specific molecule with high affinity and specificity (Ellington et al., *Nature* 346, 818-22 (1990); and Tuerk et al., *Science* 249, 505-10 (1990)). Exemplary ligands that bind to an aptamer include, without limitation, small molecules, such as drugs, metabolites, intermediates, cofactors, transition state analogs, ions, metals, nucleic acids, and toxins. Aptamers may also bind natural and synthetic polymers, including proteins, peptides, nucleic acids, polysaccharides, glycoproteins, hormones, receptors and cell surfaces such as cell walls and cell membranes. The binding of a ligand to an aptamer, which is typically RNA, causes or favors a conformational change in the actuator domain and alters its ability to interact with its target molecule. Therefore, ligand binding affects the actuator domain's ability to mediate gene inactivation, transcription, translation, or otherwise interfere with the normal activity of the target gene or mRNA, for example.

An aptamer will most typically have been obtained by in vitro selection for binding of a target molecule. However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants ($K_D$) of the aptamer for its ligand as compared to the dissociation constant of the aptamer for other materials in the environment or unrelated molecules in general. A ligand is one which binds to the aptamer with greater affinity than to unrelated material. Typically, the $K_D$ for the aptamer with respect to its ligand will be at least about 10-fold less than the $K_D$ for the aptamer with unrelated material or accompanying material in the environment. Even more preferably, the $K_D$ will be at least about 50-fold less, more preferably at least about 100-fold less, and most preferably at least about 200-fold less. An aptamer will typically be between about 10 and about 300 nucleotides in length. More commonly, an aptamer will be between about 30 and about 100 nucleotides in length.

The terms "nucleic acid molecule" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used interchangeably with oligonucleotide, gene, cDNA, and mRNA encoded by a gene.

Aptamers are readily made that bind to a wide variety of molecules. Each of these molecules can be used as a modulator of gene expression using the methods of the invention. For example, organic molecules, nucleotides, amino acids, polypeptides, target features on cell surfaces, ions, metals, salts, saccharides, have all been shown to be suitable for isolating aptamers that can specifically bind to the respective ligand. For instance, organic dyes such as Hoechst 33258 have been successfully used as target ligands for in vitro aptamer selections (Werstuck and Green, *Science* 282:296-298 (1998)). Other small organic molecules like dopamine, theophylline, sulforhodamine B, and cellobiose have also been used as ligands in the isolation of aptamers. Aptamers have also been isolated for antibiotics such as kanamycin A, lividomycin, tobramycin, neomycin B, viomycin, chloramphenicol and streptomycin. For a review of aptamers that recognize small molecules, see Famulok, *Science* 9:324-9 (1999).

In certain embodiments, the ligand of the aptamer of an aptamer-regulated nucleic acid of the invention is a cell-permeable, small organic molecule. Small organic molecules which do not have a general inhibitory effect on translation are preferred as ligands. The small molecule preferably also exhibits in vivo persistence sufficient for achieving the desired level of inhibition of translation. The molecules also can be screened to identify those that are bioavailable after, for example, oral administration. In certain embodiments of the invention, the ligand is nontoxic. The ligand may optionally be a drug, including, for example, a steroid. However, in some of the methods of controlling gene expression, it is preferable that the ligand be pharmacologically inert. In some embodiments, the ligand is a polypeptide whose presence in the cell is indicative of a disease or pathological condition. In other embodiments, the ligand for an aptamer is an antibiotic, such as chloramphenicol. In an alternative embodiment, the ligand of the aptamer is an organic dye such as Hoeschst dye 33258. In still another embodiment, the ligand may be a metal ion. In a specific embodiment, the aptamer domain of an aptamer-regulated nucleic acid responds to binding to caffeine.

The aptamer-regulated nucleic acid of the invention can be composed entirely of RNA. In other embodiments of the invention, however, the aptamer-regulated nucleic acid can instead be composed entirely of DNA, or partially of DNA, or partially of other nucleotide analogs. To specifically inhibit translation in vivo, aptamer-regulated RNAs are preferred. Such aptamer-regulated RNAs are preferably introduced into a cell as a DNA that encodes the aptamer-regulated nucleic acid sequence such that transcription results in the aptamer-regulated RNA. Alternatively, an aptamer-regulated RNA itself can be introduced into a cell.

Aptamers are typically developed to bind particular ligands by employing known in vivo or in vitro (most typically, in vitro) selection techniques known as SELEX (Ellington et al., *Nature* 346, 818-22 (1990); and Tuerk et al., *Science* 249, 505-10 (1990)). Methods of making aptamers are also described in, for example, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291.

Generally, in their most basic form, in vitro selection techniques for identifying aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present invention, the aptamer is preferably selected for ligand binding in the presence of salt concentrations and temperatures which mimic normal physiological conditions.

An improved aptamer selection scheme is described in the co-owned and co-pending U.S. application Ser. No. 12/218,628, filed on Jul. 16, 2008, the entire content of which is incorporated herein by reference.

One can generally choose a suitable ligand without reference to whether an aptamer is yet available. In most cases, an aptamer can be obtained which binds the ligand of choice by someone of ordinary skill in the art. The unique nature of the in vitro selection process allows for the isolation of a suitable aptamer that binds a desired ligand despite a complete dearth of prior knowledge as to what type of structure might bind the desired ligand.

For an aptamer to be suitable for use in the present invention, the binding affinity of the aptamer for the ligand must be sufficiently strong and the structure formed by the aptamer when bound to its ligand must be significant enough so as to switch an aptamer-regulated nucleic acid of the invention between "on" and "off" states of an aptamer-regulated nucleic acid.

The association constant for the aptamer and associated ligand is preferably such that the ligand functions to bind to the aptamer and have the desired effect at the concentration of ligand obtained upon administration of the ligand. For in vivo use, for example, the association constant should be such that binding occurs well below the concentration of ligand that can be achieved in the serum or other tissue, preferably well below the concentration of ligand that can be achieved intracellularly since cellular membranes may not be sufficiently permeable to allow the intracellular ligand concentration to approach the level in the serum or extracellular environment. Preferably, the required ligand concentration for in vivo use is also below that which could have undesired effects on the organism.

Actuator/Effector Domain

An actuator/effector nucleic acid domain may comprise an antisense nucleic acid or a DNA. An effector nucleic acid domain may also comprise a sequence that can be used as an RNAi sequence or precursor that gives rise to siRNA or miRNA. Yet other actuator domains can be an shRNA or precursor thereof, an RNase III substrate, an alternative splicing element, or an RNAi targeting sequence. In certain embodiments, the actuator of the invention does not include ribozymes or other catalytic nucleic acids.

In preferred embodiments, ligand binding at the sensor (aptamer) domain mediates a change in the conformational dynamics of these molecules that allows or prevents the actuator domain to interact with a target nucleic acid, for example, an mRNA.

In one embodiment, the actuator domain of an aptamer-regulated nucleic acid interacts with a target gene by nucleic acid hybridization. For instance, an aptamer-regulated nucleic acid may comprise an actuator domain that comprises a hybridization sequence that hybridizes to a target sequence of a gene and an aptamer domain that binds to a ligand. The binding of the ligand to the aptamer domain favors a conformational change in the aptamer-regulated nucleic acid that alters the ability (such as availability and/or $T_m$) of the hybridization sequence of the actuator domain to hybridize to a target sequence. Furthermore, an actuator domain may modulate the expression or activity of its target by any method known in the art. In one embodiment, the actuator domain of an aptamer-regulated nucleic acid comprises an antisense sequence and acts through an antisense mechanism in modulating expression of a target gene. For instance, an aptamer-regulated nucleic acid may comprise an actuator domain that comprises an antisense sequence for inhibiting expression of a target gene and an aptamer domain that binds to a ligand. The binding of the ligand to the aptamer domain causes a conformational change in the aptamer-regulated nucleic acid that alters the ability of the antisense sequence of the actuator domain to inhibit expression of the target sequence.

In another embodiment, the actuator domain of an aptamer-regulated nucleic acid comprises an actuator domain that comprises an RNAi sequence and acts through an RNAi or miRNA mechanism in modulating expression of a target gene. For instance, an aptamer-regulated nucleic acid may comprise an actuator domain that comprises a miRNA or siRNA sequence for inhibiting expression of a target gene and an aptamer domain that binds to a ligand. The binding of the ligand to the aptamer domain causes a conformational change in the aptamer-regulated nucleic acid that alters the ability of the miRNA or siRNA sequence of the actuator domain to inhibit expression of the target sequence. In one embodiment, an effector domain comprises a miRNA or siRNA sequence that is between about 19 nucleotides and about 35 nucleotides in length, or preferably between about 25 nucleotides and about 35 nucleotides. In certain embodiments, the actuator domain is a hairpin loop that may be processed by RNase III enzymes (e.g., Drosha and Dicer). As used herein, the term "RNAi" means an RNA-mediated mechanism for attenuating gene expression and includes small RNA-mediated silencing mechanisms. RNA-mediated silencing mechanisms include inhibition of mRNA translation and directed cleavage of targeted mRNAs. Recent evidence has suggested that certain RNAi constructs may also act through chromosomal silencing, i.e., at the genomic level, rather than, or in addition to, the mRNA level. Thus, the sequence targeted by the actuator domain can also be selected from untranscribed sequences that regulate transcription of a target gene at the genomic level.

The methods described herein may employ an expression vector having a coding sequence that is transcribed to produce one or more transcriptional products that produce an aptamer-regulated nucleic acid in the treated cells. Expression vectors appropriate for producing an aptamer-regulated nucleic acid are well-known in the art. For example, the expression vector is selected from an episomal expression vector, an integrative expression vector, and a viral expression vector. In another preferred embodiment, the aptamer-regulated nucleic acid comprises a hairpin RNA which is processed to an siRNA in the treated cells.

In certain embodiments, the expression construct can be designed to include one or more subject regulated polynucleotides in an RNA transcript, such as in the 3' untranslated region (3'-UTR), so as to regulate transcription, stability and/or translation of that RNA transcript in a manner dependent on the ligand. To further illustrate, the expression construct can include a coding sequence for a polypeptide such that the mRNA transcript includes both the polypeptide coding sequence as well as one or more of the regulated polynucleotides of the invention. In this way, expression of the polypeptide can be rendered dependent on the ligand to which the aptamer binds.

The invention further provides a class of in vivo nucleic acid sensors, for example, aptamer-regulated nucleic acids that directly sense the presence or amount an intracellular molecule through changes in nucleic acid conformation upon ligand binding to the aptamer domain of an aptamer-regulated nucleic acid. For example, a ligand that interacts with the aptamer domain of an aptamer-regulated nucleic acid switches "on" the actuator domain of the aptamer-regulated nucleic acid. The activated actuator domain then targets a "reporter" molecule. The reporter molecule is activated or repressed by its interaction with the actuator domain. The amount or activity of the reporter molecule, therefore, correlates with the amount or concentration of the ligand of interest. Exemplary reporter molecules include, without limitation, fluorescent reporter proteins such as green fluorescent protein (GFP or any of its art-recognized variants) or luciferase, enzymatic reporters such as alkaline phosphatase, or colorimetric reporters such as lacZ.

Antiswitches

An aptamer-regulated nucleic acid of the invention may comprise an actuator domain that comprises an antisense sequence and acts through an antisense mechanism for inhibiting expression of a target gene. As used herein, such aptamer-regulated nucleic acids are also referred to as "antiswitches." Antisense technologies have been widely utilized to regulate gene expression (Buskirk et al., *Chem Biol* 11, 1157-63 (2004); and Weiss et al., *Cell Mol Life Sci* 55, 334-58 (1999)). As used herein, "antisense" technology refers to administration or in situ generation of molecules or their derivatives which specifically hybridize (e.g., bind) under cellular conditions, with the target nucleic acid of interest (mRNA and/or genomic DNA) encoding one or more of the target proteins so as to inhibit expression of that protein, e.g., by inhibiting transcription and/or translation, such as by steric hindrance, altering splicing, or inducing cleavage or other enzymatic inactivation of the transcript. The binding may be by conventional base pair complementarity, or, for example, in the case of binding to DNA duplexes, through specific interactions in the major groove of the double helix. In general, "antisense" technology refers to the range of techniques generally employed in the art, and includes any therapy that relies on specific binding to nucleic acid sequences.

An aptamer-regulated nucleic acid that comprises an antisense effector domain of the present invention can be delivered, for example, as a component of an expression plasmid which, when transcribed in the cell, produces an effector domain which is complementary to at least a unique portion of the target nucleic acid. Alternatively, the aptamer-regulated nucleic acid that comprises an antisense effector domain can be generated outside of the target cell, and which, when introduced into the target cell causes inhibition of expression by hybridizing with the target nucleic acid. Aptamer-regulated nucleic acids may be modified so that they are resistant to endogenous nucleases, e.g. exonucleases and/or endonucleases, and are therefore stable in vivo. Exemplary nucleic acid molecules for use in aptamer-regulated nucleic acids are phosphoramidate, phosphothioate and methylphosphonate analogs of DNA (see also U.S. Pat. Nos. 5,176,996; 5,264, 564; and 5,256,775). General approaches to constructing oligomers useful in antisense technology have been reviewed, for example, by van der Krol et al. (1988) Biotechniques 6:958-976; and Stein et al. (1988) Cancer Res 48:2659-2668.

Several considerations may be taken into account when constructing antisense actuator domains for use in the compositions and methods of the invention: (1) antisense actuator domains preferably have a GC content of 50% or more; (2) generally, avoid sequences with stretches of 3 or more Gs; and (3) antisense actuator domains preferably should not be longer than 25-26 mers when in their "on" state and modulating a target gene. When testing an antisense actuator domain, a mismatched control can be constructed. The controls can be generated by reversing or scrambling the sequence order of the corresponding antisense oligonucleotide in order to conserve the same ratio of bases.

Antisense approaches involve the design of actuator domains (either DNA or RNA) that are complementary to a target nucleic acid encoding a protein of interest. The antisense effector domain may bind to an mRNA transcript and prevent translation of a protein of interest. Absolute complementarity, although preferred, is not required. In the case of double-stranded antisense actuator domains, a single strand of the duplex DNA may thus be tested, or triplex formation may be assayed. The ability to hybridize will depend on both the degree of complementarity and the length of the antisense sequence. Generally, the longer the hybridizing nucleic acid, the more base mismatches with a target nucleic acid it may contain and still form a stable duplex (or triplex, as the case may be). One skilled in the art can ascertain a tolerable degree of mismatch by use of standard procedures to determine the melting point of the hybridized complex.

Antisense actuator domains that are complementary to the 5' end of an mRNA target, e.g., the 5' untranslated sequence up to and including the AUG initiation codon, should work most efficiently at inhibiting translation of the mRNA. However, sequences complementary to the 3' untranslated sequences of mRNAs have recently been shown to be effective at inhibiting translation of mRNAs as well (Wagner, R. 1994. *Nature* 372:333). Therefore, antisense actuator domains complementary to either the 5' or 3' untranslated, non-coding regions of a target gene could be used in an antisense approach to inhibit translation of a target mRNA. Antisense actuator domains complementary to the 5' untranslated region of an mRNA should include the complement of the AUG start codon. Antisense oligonucleotides complementary to mRNA coding regions are less efficient inhibitors of translation but could also be used in accordance with the invention. Whether designed to hybridize to the 5', 3', or coding region of mRNA, antisense nucleic acids should be at least six nucleotides in length, and are preferably less than about 100, and more preferably less than about 50, 25, 17 or 10 nucleotides in length.

Regardless of the choice of target sequence, it is preferred that in vitro studies are first performed to quantitate the ability of the antiswitch to inhibit expression of a target gene. It is preferred that these studies utilize controls that distinguish between antisense gene inhibition and nonspecific biological effects of antiswitches. It is also preferred that these studies compare levels of the target RNA or protein with that of an internal control RNA or protein. Additionally, it is envisioned that results obtained using the antiswitch are compared with those obtained using a control antiswitch. It is preferred that the control antiswitch is of approximately the same length as the test antiswitch and that the nucleotide sequence of the control antiswitch differs from the antisense sequence of interest no more than is necessary to prevent specific hybridization to the target sequence.

Antiswitches can be DNA or RNA or chimeric mixtures or derivatives or modified versions thereof, single-stranded or double-stranded. Antiswitches can be modified at the base moiety, sugar moiety, or phosphate backbone, for example, to improve stability of the molecule, hybridization, etc. Antiswitches may include other appended groups such as peptides (e.g., for targeting host cell receptors), or agents facilitating transport across the cell membrane (see, e.g., Letsinger et al., 1989, *Proc Natl Acad. Sci. USA* 86:6553-6556; Lemaitre et al., 1987, *Proc Natl Acad. Sci. USA* 84:648-652; PCT Publication No. WO88/09810, published Dec. 15, 1988) or the blood-brain barrier (see, e.g., PCT Publication No. WO89/ 10134, published Apr. 25, 1988), hybridization-triggered cleavage agents. (See, e.g., Krol et al., 1988, *BioTechniques* 6:958-976) or intercalating agents. (See, e.g., Zon, *Pharm. Res.* 5:539-549 (1988)). To this end, an antiswitch may be conjugated to another molecule, e.g., a peptide, hybridization triggered cross-linking agent, transport agent, hybridization-triggered cleavage agent, etc.

An antiswitch may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

An antiswitch may also comprise at least one modified sugar moiety selected from the group including but not limited to arabinose, 2-fluoroarabinose, xylulose, and hexose.

An antiswitch can also contain a neutral peptide-like backbone. Such molecules are termed peptide nucleic acid (PNA)-oligomers and are described, e.g., in Perry-O'Keefe et al. (1996) *Proc. Natl. Acad. Sci. USA* 93:14670 and in Eglom et al. (1993) *Nature* 365:566. One advantage of PNA oligomers is their capability to bind to complementary DNA essentially independently from the ionic strength of the medium due to the neutral backbone of the DNA. In yet another embodiment, an antiswitch comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, an antiswitch is an anomeric oligonucleotide. An anomeric oligonucleotide forms specific double-stranded hybrids with complementary RNA in which, contrary to the usual units, the strands run parallel to each other (Gautier et al., 1987, *Nucl. Acids Res.* 15:6625-6641). The oligonucleotide is a 2'-O-methylribonucleotide (Inoue et al., 1987, *Nucl. Acids Res.* 15:6131-6148), or a chimeric RNA-DNA analogue (Inoue et al., 1987, *FEBS Lett.* 215:327-330).

Aptamer-regulated nucleic acids of the invention, including antiswitches, may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. *Nucl. Acids Res.* 16:3209 (1988)), methylphosphonate oligonucleotides can be prepared by use of controlled pore glass polymer supports (Sarin et al., *Proc. Natl. Acad. Sci. USA* 85:7448-7451 (1988)), etc.

While antisense sequences complementary to the coding region of an mRNA sequence can be used, those complementary to the transcribed untranslated region and to the region comprising the initiating methionine are most preferred.

Antiswitch nucleic acid molecules can be delivered to cells that express target genes in vivo. A number of methods have been developed for delivering nucleic acids into cells; e.g., they can be injected directly into the tissue site, or modified nucleic acids, designed to target the desired cells (e.g., antiswitches linked to peptides or antibodies that specifically bind receptors or antigens expressed on the target cell surface) can be administered systematically.

However, it may be difficult to achieve intracellular concentrations of the antiswitch sufficient to attenuate the activity of a target gene or mRNA or interest in certain instances. Therefore, another approach utilizes a recombinant DNA construct in which the antiswitch or other aptamer-regulated nucleic acid is placed under the control of a strong pol III or pol II promoter. The use of such a construct to transfect target cells in the patient will result in the transcription of sufficient amounts of antiswitches that will form complementary base pairs with the target gene or mRNA and thereby attenuate the activity of the protein of interest. For example, a vector can be introduced in vivo such that it is taken up by a cell and directs the transcription of an antiswitch. Such a vector can remain episomal or become chromosomally integrated, as long as it can be transcribed to produce the desired antiswitch. Such vectors can be constructed by recombinant DNA technology methods standard in the art. Vectors can be plasmid, viral, or others known in the art, used for replication and expression in mammalian cells. A promoter may be operably linked to the sequence encoding the antiswitch. Expression of the sequence encoding the antiswitch can be by any promoter known in the art to act in mammalian, preferably human cells. Such promoters can be inducible or constitutive. Such promoters include but are not limited to: the SV40 early promoter region (Bernoist and Chambon, *Nature* 290:304-310 (1981)), the promoter contained in the 3' long terminal repeat of Rous sarcoma virus (Yamamoto et al., *Cell* 22:787-797 (1980)), the herpes thymidine kinase promoter (Wagner et al., *Proc. Natl. Acad. Sci. USA* 78:1441-1445 (1981)), the regulatory sequences of the metallothionine gene (Brinster et al, *Nature* 296:3942 (1982)), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

RNAi-Based Switch Constructs (with siRNA or miRNA Actuator Domains)

RNA interference (RNAi) is a phenomenon describing double-stranded (ds)RNA-dependent gene specific posttranscriptional silencing. Initial attempts to harness this phenomenon for experimental manipulation of mammalian cells were foiled by a robust and nonspecific antiviral defense mechanism activated in response to long dsRNA molecules. Gil et al. Apoptosis 2000, 5:107-114. The field was significantly advanced upon the demonstration that synthetic duplexes of 21 nucleotide RNAs could mediate gene specific RNAi in mammalian cells, without invoking generic antiviral defense mechanisms. Elbashir et al. Nature 2001, 411:494-498; Caplen et al. Proc Natl Acad Sci 2001, 98:9742-9747. As a result, siRNAs and miRNAs have become powerful tools to dissect gene function. The chemical synthesis of small RNAs is one avenue that has produced promising results. Numerous groups have also sought the development of DNA-based vectors capable of generating such siRNA within cells. Several groups have recently attained this goal and published similar strategies that, in general, involve transcription of short hairpin (sh)RNAs that are efficiently processed to form siRNAs within cells. Paddison et al. PNAS 2002, 99:1443-1448; Paddison et al. Genes & Dev 2002, 16:948-958; Sui et al. PNAS 2002, 8:5515-5520; and Brummelkamp et al. Science 2002, 296:550-553. These reports describe methods to generate siRNAs capable of specifically targeting numerous endogenously and exogenously expressed genes.

Accordingly, the present invention provides an aptamer-regulated nucleic acid comprising an actuator domain that comprises an RNAi sequence and acts through an RNAi or miRNA mechanism to attenuate expression of a target gene. For instance, an aptamer-regulated nucleic acid may comprise an actuator domain that comprises a miRNA or siRNA sequence or precursor thereof. In one embodiment, an actuator domain comprises a miRNA or siRNA sequence that is between about 19 nucleotides and about 75 nucleotides in length, or preferably, between about 25 base pairs and about 35 base pairs in length. In certain embodiments, the actuator domain is a hairpin loop that may be processed by RNase III enzymes (e.g., Drosha and Dicer).

An RNAi construct contains a nucleotide sequence that hybridizes under the physiologic conditions of the cell to the nucleotide sequence of at least a portion of the mRNA transcript for the gene to be inhibited (i.e., the "target" gene). The double-stranded RNA only needs to be sufficiently similar to natural RNA for its ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may abolish cleavage of the target RNA. In contrast, nucleotides at the 3' end of the siRNA strand that is complementary to the target RNA do not significantly contribute to specificity of the target recognition. However, certain miRNA designs, such as the mir-30 based miRNA designs, may feature a bulge of about a few nucleotides in the middle of the guide sequence.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of aptamer-regulated nucleic acids that comprise an actuator domain comprising RNAi sequences can be carried out by any of the methods for producing aptamer-regulated nucleic acids described herein. For example, an aptamer-regulated nucleic acid can be produced by chemical synthetic methods or by recombinant nucleic acid techniques. Endogenous RNA polymerase of the treated cell may mediate transcription in vivo, or cloned RNA polymerase can be used for transcription in vitro. Aptamer-regulated nucleic acids, including antiswitches or those that modulate target gene activity by RNAi mechanisms may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. Aptamer-regulated nucleic acids may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, chimeric methylphosphonate-phosphodiesters, phosphodithioates, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "siRNAs." These nucleic acids are between about 19-35 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex or translation is inhibited. In a particular embodiment, the 21-23 nucleotides siRNA molecules comprise a 3' hydroxyl group.

In other embodiments, the subject RNAi constructs are "miRNAs." microRNAs (miRNAs) are small non-coding RNAs that direct post transcriptional regulation of gene expression through interaction with homologous mRNAs. miRNAs control the expression of genes by binding to complementary sites in target mRNAs from protein coding genes. miRNAs are similar to siRNAs. miRNAs are processed by nucleolytic cleavage from larger double-stranded precursor molecules. These precursor molecules are often hairpin structures of about 70 nucleotides in length, with 25 or more nucleotides that are base-paired in the hairpin. The RNase III-like enzymes Drosha and Dicer (which may also be used in siRNA processing) cleave the miRNA precursor to produce an miRNA. The processed miRNA is single-stranded and incorporates into a protein complex, termed RISC or miRNP. This RNA-protein complex targets a complementary mRNA. miRNAs inhibit translation or direct cleavage of target mRNAs. (Brennecke et al., Genome Biology 4:228 (2003); Kim et al., Mol. Cells. 19:1-15 (2005).

In certain embodiments, miRNA and siRNA constructs can be generated by processing of longer double-stranded RNAs, for example, in the presence of the enzymes Dicer or Drosha. Dicer and Drosha are RNAse III-like nucleases that specifically cleave dsRNA. Dicer has a distinctive structure which includes a helicase domain and dual RNAse III motifs. Dicer also contains a region of homology to the RDE1/QDE2/ Argonaute family, which have been genetically linked to RNAi in lower eukaryotes. Indeed, activation of, or overexpression of Dicer may be sufficient in many cases to permit RNA interference in otherwise non-receptive cells, such as cultured eukaryotic cells, or mammalian (non-oocytic) cells in culture or in whole organisms. Methods and compositions employing Dicer, as well as other RNAi enzymes, are described in U.S. Pat. App. Publication No. 20040086884.

In one embodiment, the *Drosophila* in vitro system is used. In this embodiment, an aptamer-regulated nucleic acid is combined with a soluble extract derived from *Drosophila* embryo, thereby producing a mixture, which is maintained under conditions in which the dsRNA is processed to RNA molecules of about 21 to about 23 nucleotides.

The miRNA and siRNA molecules can be purified using a number of techniques known to those of skill in the art. For example, gel electrophoresis can be used to purify such molecules. Alternatively, non-denaturing methods, such as non-denaturing column chromatography, can be used to purify the siRNA and miRNA molecules. In addition, chromatography (e.g., size exclusion chromatography), glycerol gradient centrifugation, affinity purification with antibody can be used to purify siRNAs and miRNAs.

In certain preferred embodiments, at least one strand of the siRNA sequence of an effector domain has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA sequence, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In certain embodiments, an aptamer-regulated nucleic acid is in the form of a hairpin structure (named as hairpin RNA). The hairpin RNAs can be synthesized exogenously or can be formed by transcribing from RNA polymerase II or III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that miRNAs and siRNAs can be produced by processing a hairpin RNA in the cell.

In yet other embodiments, a plasmid is used to deliver the double-stranded RNA, e.g., as a transcriptional product. After the coding sequence is transcribed, the complementary RNA transcripts base-pair to form the double-stranded RNA.

4. Exemplary Formulations

The aptamer-regulated nucleic acids of the invention may also be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption. The subject aptamer-regulated nucleic acids can be provided in formulations also including penetration enhancers, carrier compounds and/or transfection agents.

Representative United States patents that teach the preparation of such uptake, distribution and/or absorption assisting formulations which can be adapted for delivery of switch molecules include, but are not limited to, U.S. Pat. Nos. 5,108,921; 5,354,844; 5,416,016; 5,459,127; 5,521,291; 51,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

Aptamer-regulated nucleic acids of the invention also encompass any pharmaceutically acceptable salts, esters or salts of such esters, or any other compound which, upon administration to an animal including a human, is capable of providing (directly or indirectly) the biologically active metabolite or residue thereof. Accordingly, for example, the disclosure is also drawn to aptamer-regulated nucleic acids and pharmaceutically acceptable salts, and other bioequivalents.

Pharmaceutically acceptable base addition salts are formed with metals or amines, such as alkali and alkaline earth metals or organic amines. Examples of metals used as cations are sodium potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of the acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids. Preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

Other formulations, delivery methods, and routes of administration are also provided, such as those described in U.S. Pat. App. Publication No. 20040063654.

5. Exemplary Uses

One aspect of the invention provides a method of modulating the amount and/or activity of a ligand in a cell. The method may comprise designing and selecting an aptamer responsive to the ligand and providing an aptamer-regulated nucleic acid comprising the selected aptamer and an effector RNA, and the effector RNA is targeted to a molecule, a signaling and/or metabolic pathway in the cell that involves the ligand, for example, as a metabolite or an intermediate molecule (or the ligand-associated signaling and/or metabolic pathway). The method may further comprise contacting a cell with the aptamer-regulated nucleic acid in an amount and/or for a time period sufficient for modulating the concentration and/or activity of the ligand in the cell when switched "on."

Also provided is a method of modulating a biological or biochemical response of a cell to the presence, amount and/or activity of a ligand in a cell. The method may comprise designing and selecting an aptamer responsive to the ligand and providing an aptamer-regulated nucleic acid comprising the selected aptamer and an effector RNA, and the effector RNA is targeted to a gene that modulates a biological or biochemical response of the cell to the presence, amount and/or activity of the ligand in the cell. The method may further comprise contacting a cell with the aptamer-regulated nucleic acid in an amount and/or for a time period sufficient for modulating the biological or biochemical response of the cell when switched "on."

Certain embodiments are also directed to a method of establishing a conditional genetic network, as described herein. The method may comprise providing an aptamer-regulated nucleic acid that comprises an aptamer domain and an effector domain; the aptamer domain is responsive to a ligand, while the effector domain is targeted to a molecule that is independent of the ligand-associated signaling pathway. The method further comprises contacting the cell with the aptamer-regulated nucleic acid in an effective amount and/or for a sufficient time period, when switched "on," that modulates expression of the target molecule, thereby establishing a conditional genetic network.

In a further aspect, a method of the invention is used to inhibit, or at least reduce, unwanted growth of cells in vivo, and particularly the growth of transformed cells. In certain embodiments, the subject method utilizes one or more aptamer-regulated nucleic acids of the invention to selectively inhibit the expression of genes encoding proliferation-regulating proteins. For instance, the subject method can be used to inhibit expression of a gene product that is essential to mitosis in the target cell, and/or which is essential to preventing apoptosis of the target cell. The aptamer-regulated nucleic acids of the present invention, in particular, the effector domains, can be designed to correspond to the coding sequence or other portions of mRNAs encoding the targeted proliferation-regulating protein. When treated with the aptamer-regulated nucleic acid, the loss-of-expression phenotype which results in the target cell causes the cell to become quiescent or to undergo apoptosis.

In certain embodiments, the subject aptamer-regulated nucleic acids are selected to inhibit expression of gene products which stimulate cell growth and mitosis. One class of genes which can be targeted by the method of the present invention are those known as oncogenes. As used herein, the term "oncogene" refers to a gene which stimulates cell growth and, when its level of expression in the cell is reduced, the rate of cell growth is reduced or the cell becomes quiescent. In the context of the present invention, oncogenes include intracellular proteins, as well as extracellular growth factors which may stimulate cell proliferation through autocrine or paracrine function. Examples of human oncogenes against which switch molecules can designed include c-myc, c-myb, mdm2, PKA-I (protein kinase A type I), Abl-1, Bcl2, Ras, c-Raf kinase, CDC25 phosphatases, cyclins, cyclin dependent kinases (cdks), telomerase, PDGF/sis, erb-B, fos, jun, mos, and src, to name but a few. In the context of the present invention, oncogenes also include a fusion gene resulted from chromosomal translocation, for example, the Bcr/Abl fusion oncogene.

In certain embodiments, the cell is a transformed cell so that the aptamer-regulated nucleic acid is used for the treatment of hyperplastic cell growth, including treatment of a cancer. In other embodiments, the aptamer-regulated nucleic acid is used for inhibiting activation of lymphocytes, including treatment or prophylaxis of immune-mediated inflammatory disorders. In still other embodiments, the aptamer-regulated nucleic acid is used for inhibiting proliferation of smooth muscle cells, including treatment or prophylaxis of restenosis. In yet other embodiments, the aptamer-regulated nucleic acid is used for inhibiting proliferation of epithelial cells (e.g., as a component of cosmetic preparations).

In certain preferred embodiments, the subject aptamer-regulated nucleic acids are selected by their ability to inhibit expression of a gene(s) essential for proliferation of a transformed cell, and particularly of a tumor cell. Such that the aptamer-regulated nucleic acids can be used as part of the treatment or prophylaxis for neoplastic, anaplastic and/or hyperplastic cell growth in vivo, including as part of a treatment of a tumor. The c-myc protein is deregulated in many forms of cancer, resulting in increased expression. Reduction of c-myc RNA levels in vitro results in induction of apoptosis. An antisense, siRNA, miRNA, or RNAi effector domain complementary to c-myc can therefore potentially be used as therapeutic for anti-cancer treatment. Preferably, the subject aptamer-regulated nucleic acids can be used in the therapeutic treatment of chronic lymphatic leukemia. Chronic lymphatic leukemia is often caused by a translocation of chromosomes 9 and 12 resulting in a Bcr/Abl fusion product. The resulting fusion protein acts as an oncogene; therefore, specific elimination of Bcr/Abl fusion mRNA may result in cell death in the leukemia cells. Indeed, transfection of siRNA molecules specific for the Bcr/Abl fusion mRNA into cultured leukemic cells, not only reduced the fusion mRNA and corresponding oncoprotein, but also induced apoptosis of these cells (see, for example, Wilda et al., Oncogene, 2002, 21:5716-5724).

In other embodiments, the subject aptamer-regulated nucleic acids are selected by their ability to inhibit expression of a gene(s) essential for activation of lymphocytes, e.g., proliferation of B-cells or T-cells, and particularly of antigen-mediated activation of lymphocytes. Such aptamer-regulated nucleic acids can be used as immunosuppressant agents, e.g., as part of the treatment or prophylaxis for immune-mediated inflammatory disorders.

Alternatively, in other embodiments, the subject aptamer-regulated nucleic acids are selected by their ability to regulate activation of immune cells in response to particular exogenous or endogenous signals (such as cytokines or small molecules) in, for example, cell-based immunotherapy applications.

In certain embodiments, the methods described herein can be employed for the treatment of autoimmune disorders. For example, the subject aptamer-regulated nucleic acids are selected for their ability to inhibit expression of a gene(s) which encode or regulate the expression of cytokines. Accordingly, constructs that cause inhibited or decreased expression of cytokines such as TNF-alpha, IL-1 alpha, IL-6 or IL-12, or a combination thereof, can be used as part of a treatment or prophylaxis for rheumatoid arthritis. Similarly, constructs that cause inhibited or decreased expression of cytokines involved in inflammation can be used in the treatment or prophylaxis of inflammation and inflammation-related diseases, such as multiple sclerosis.

In other embodiments, the subject aptamer-regulated nucleic acids are selected for their ability to inhibit expression of a gene(s) implicated in the onset or progression of diabetes. For example, experimental diabetes mellitus was found to be related to an increase in expression of p21WAF1/CIP1 (p21), and TGF-beta 1 has been implicated in glomerular hypertrophy (see, for example, Al-Douahji, et al. Kidney Int. 56:1691-1699). Accordingly, constructs that cause inhibited or decreased expression of these proteins can be used in the treatment or prophylaxis of diabetes.

In other embodiments, the subject aptamer-regulated nucleic acids are selected for their ability to inhibit expression of ICAM-1 (intracellular adhesion molecule). An antisense nucleic acid that inhibits expression of ICAM-1 is being developed by Isis pharmaceutics for psoriasis. Additionally, an antisense nucleic acid against the ICAM-1 gene is suggested for preventing acute renal failure and reperfusion injury and for prolonging renal isograft survival (see, for example, Halier et al. (1996) Kidney Int. 50:473-80; Dragun et al. (1998) Kidney Int. 54:590-602; Dragun et al., (1998) Kidney Int. 54:2113-22). Accordingly, the present invention contemplates the use of aptamer-regulated nucleic acids comprising similar antisense effector RNA domains, siRNA, miRNA, or RNAi effector domains targeting ICAM-1 gene in the above-described diseases.

In other embodiments, the subject aptamer-regulated nucleic acids are selected by their ability to inhibit expression of a gene(s) essential for proliferation of smooth muscle cells or other cells of endothelium of blood vessels, such as proliferating cells involved in neointima formation. In such embodiments, the subject method can be used as part of a treatment or prophylaxis for restenosis.

Merely to illustrate, aptamer-regulated nucleic acids applied to the blood vessel endothelial cells after angioplasty can reduce proliferation of these cells after the procedure. Merely to illustrate, a specific example is an siRNA complementary to c-myc (an oncogene). Down-regulation of c-myc inhibits cell growth. Therefore, an effector domain comprising an siRNA sequence can be prepared by including the following sequence in an effector domain:

```
5'-UCCCGCGACGAUGCCCCUCATT-3'    (SEQ ID NO: 1)

3'-TTAGGGCGCUGCUACGGGGAGU-5'    (SEQ ID NO: 2)
```

All bases are ribonucleic acids except the thymidines shown in bold, which are deoxyribose nucleic acids (for more stability). Double-stranded RNA can be prepared by mixing the oligonucleotides at equimolar concentrations in 10 mM Tris-Cl (pH 7.0) and 20 mM NaCl, heating to 95° C., and then slowly cooling to 37° C. Alternatively, the sequence can be included in a hairpin structure. The resulting nucleic acid can then be purified by agarose gel electrophoresis and delivered to cells either free or complexed to a delivery system such as a cyclodextrin-based polymer. For in vitro experiments, the effect of the aptamer-regulated nucleic acid can be monitored by growth curve analysis, RT-PCR or western blot analysis for the c-myc protein.

It is demonstrated that antisense oligodeoxynucleotides directed against the c-myc gene inhibit restenosis when given by local delivery immediately after coronary stent implantation (see, for example, Kutryk et al. (2002) J Am Coll Cardiol. 39:281-287; Kipshidze et al. (2002) J Am Coll Cardiol. 39:1686-1691). Therefore, the present invention contemplates delivering an aptamer-regulated nucleic acid against the c-Myc gene (i.e., c-Myc antisense or RNAi construct) to the stent implantation site with an infiltrator delivery system (Interventional Technologies, San Diego, Calif.). Preferably, the c-Myc-targeting aptamer-regulated nucleic acid is directly coated on stents for inhibiting restenosis. Similarly, the c-Myc-targeting aptamer-regulated nucleic acid can be delivered locally for inhibiting myointimal hyperplasia after percutaneous transluminal coronary angioplasty (PTCA) and exemplary methods of such local delivery can be found, for example, Kipshidze et al. (2001) Catheter Cardiovasc Interv. 54:247-56. In certain embodiments, the aptamer-regulated nucleic acids are chemically modified with, for example, phosphorothioates or phosphoramidate.

Early growth response factor-1 (i.e., Egr-1) is a transcription factor that is activated during mechanical injury and regulates transcription of many genes involved with cell proliferation and migration. Therefore, down-regulation of this protein may also be an approach for prevention of restenosis. An effector domain of an aptamer-regulated nucleic acid directed against the Egr-1 gene can be prepared by including the following sequence in the effector domain:

```
5'-UCGUCCAGGAUGGCCGCGGTT-3'    (SEQ ID NO: 3)

3'-TTAGCAGGUCCUACCGGCGCC-5'    (SEQ ID NO: 4)
```

Again, all bases are ribonucleic acids except the thymidines shown in bold, which are deoxyribose nucleic acids. The effector domains and thereby the aptamer-regulated nucleic acids can be prepared from these sequences and introduced into cells as described herein.

A further aspect of invention relates to applications of a ligand controlled nucleic acid molecule in different fields. For example, an aptamer-regulated nucleic acid can be employed to detect the presence or absence or the amount of a target molecule in a sample. The target molecule may be a metabolite, an ion, a peptide, a nucleic acid, etc. An aptamer-regulated nucleic acid can similarly be employed for imaging purposes. Further, an aptamer-regulated nucleic acid can be employed to target the effector nucleic acid domain to certain environments, e.g., a particular intracellular location or cell membrane.

An aptamer-regulated nucleic acid of the invention can function as a tool to sense and detect metabolite levels in a cell, which can be noninvasive. The imaging or detection can be used for quantification of one or more metabolites of interest. Alternatively, it can be used to regulate certain enzymes in a signaling pathway for control over flux through a pathway and product formation or to alter that metabolic state by targeting levels of proteins or enzymes in a cell.

In one embodiment, the invention provides a method of modulating the concentration and/or activity of a ligand in a cell. The method may comprise designing and selecting an aptamer responsive to the ligand and providing an aptamer-regulated nucleic acid comprising the selected aptamer and an effector RNA, wherein the effector RNA is targeted to a molecule, a signaling pathway, or a metabolic pathway in a cell that involves the ligand (e.g., a metabolite or an intermediate molecule). The methods of the invention may be used, for example, to respond to the accumulation of a toxic intermediate, to attenuate the activity of a signaling or metabolic pathway, or to alter the growth, survival, or differentiation of treated cells.

In another embodiment, a method is provided for modulating the concentration and/or activity of a target gene that is in a different signaling and/or metabolic pathway than that of the ligand. According to this method, aptamer-regulated nucleic acids may be used to establish conditional genetic networks. The method may comprise designing and selecting an aptamer responsive to a ligand and providing an aptamer-regulated nucleic acid comprising the selected aptamer and an effector RNA that is targeted to a molecule, a signaling pathway, or a metabolic pathway in a cell that is independent of the ligand-associated signaling pathway. Accordingly, aptamer-regulated nucleic acids may be used to engineer intracellular gene networks by sensing endogenously generated signals (e.g., ligands) and responding to these signals by affecting the expression of a gene in signaling pathways independent of the ligand. Aptamer-regulated nucleic acids may be used to allow cells to appropriately respond to the buildup of toxic intermediates and compounds, or to alter the physiology of a cell (e.g., growth, survival, or differentiation).

In a related embodiment, the methods and compositions of the invention may be adapted to monitor the concentration of metabolites. The method may comprise a sensor aptamer-regulated nucleic acid wherein the aptamer domain of the switch is responsive to the metabolite. By measuring changes in metabolite concentrations, aptamer-regulated nucleic acids may be used to determine the full range of biochemical effects induced, for example, by a therapeutic intervention. Aptamer-regulated nucleic acids can further be used to diagnose or predict disease by monitoring metabolite concentrations.

In other embodiments, aptamer-regulated nucleic acids can serve as tools for interfacing with the environment including both intracellular environment and extracellular environment. For example, an aptamer-regulated nucleic acid can be used to "transport" a target RNA to the cell membrane or other cellular locations, potentially by the aptamer domain that recognizes a signal peptide, and alternatively, a particular target.

EXAMPLES

Having generally described the invention, Applicants refer to the following illustrative examples to help to understand the generally described invention. These specific examples are included merely to illustrate certain aspects and embodiments of the present invention, and they are not intended to limit the invention in any respect. Certain general principles described in the examples, however, may be generally applicable to other aspects or embodiments of the invention.

Progress in constructing biological networks will rely on the development of more advanced components that can be predictably modified to yield optimal system performance. Applicants have engineered an RNA-based platform ("shRNA switch" as used herein) that provides for integrated ligand control of RNA interference (RNAi) by modular coupling of an aptamer, switching strand, and small hairpin (sh) RNA stem into a single component that links ligand concentration and target gene expression levels. The follow Examples 1-9 illustrate a combined experimental and mathematical modeling approach that have identified multiple tuning strategies, and moves toward a predictable framework for the forward rational design of switches, such as shRNA switches. The utility of this general platform is highlighted by the demonstration of fine tuning, and model-guided design of shRNA switches with an optimized dynamic range, although other switches based on ribozyme or antisense sequences can also be designed based on the same principle with minor modification. Thus, such switches can serve as an advanced component for the construction of complex biological systems and offer a controlled means of activating various actuator domains (such as RNAi substrates) in disease therapeutics.

Example 1

Design and Characterization of a Modular shRNA Switch Platform

Applicants have developed a framework for the construction of shRNA switches that mediate ligand control of RNAi across diverse mammalian cell types. The platform utilizes a strand displacement strategy, where the functions of ligand binding, translation of the binding interaction into reduced processing by the RNAi machinery, and RNAi activation are isolated to individual domains, which demonstrates the generality of the method in other switch platforms (e.g., ribozyme-based switch and antisense-based switch, etc.), and the ease of successful domain swapping and subsequent broad application in these switch platforms.

In addition, Applicants used the shRNA switch platform as a model to systematically investigate tunability of the switch transfer function through a combined experimental and mathematical modeling approach that resulted in the identification of five generally applicable tuning strategies. Standard RNA folding algorithms (Mathews et al, 2004) were employed to establish a quantitative sequence-to-function relationship. These efforts highlight the current limitations of these broadly-used algorithms for the design of RNAs that function in vivo and offer a framework for optimizing RNA switch behavior in silico. By demonstrating combinatorial tuning strategies, and model-guided forward design of shRNA switches with an optimized dynamic range within a specified context, Applicants show that polynucleotide switches (such as the shRNA switch used in these experiments) can be used in the construction of complex biological systems by modularly and rationally combining the number of available components. The resulting switches can be used as a regulatory tool for gene expression.

Applicants engineered a complex RNAi substrate that encodes a ligand-controlled gene regulatory function by replacing the loop of a small hairpin (sh)RNA with two domains: an aptamer and a switching strand (FIG. 1A). A competing strand (not marked), continuous with the switching strand, forms part of the shRNA stem. The shRNA switch molecule is designed to adopt distinct "active" and "inactive" conformations due to complementarity between the switching strand and the shRNA stem. In the active conformation, irreversible processing by the RNAi machinery of the formed shRNA stem results in small interfering (si)RNA production and subsequent RNAi-mediated silencing of the target gene. In the inactive conformation, base-pairing by the switching strand disrupts the shRNA stem, which is predicted to inhibit processing by the RNAi machinery (Macrae et al, 2006; Zeng and Cullen, 2004). This base-pairing coincides with formation of the aptamer domain, such that ligand binding stabilizes the inactive conformation and indirectly reduces siRNA production, thereby linking intracellular ligand concentration to target protein levels through a component transfer function. To decrease the activation energy separating the two conformations, Applicants removed two nucleotides in the passenger strand, thereby mimicking the bulge from the microRNA (miRNA) mir-30a (Griffiths-Jones, 2004; Griffiths-Jones et al, 2006).

The three domains that comprise an shRNA switch perform distinct functions: the shRNA stem encodes the guide strand that activates RNAi-mediated silencing of the target gene, the aptamer detects the molecular input concentration through a ligand-binding interaction, and the switching strand translates the binding interaction into a decrease in regulatory activity by affecting processing by the RNAi machinery. Based on the action of the switching strand that is complementary to the shRNA stem, the sequences of the shRNA stem and aptamer domains are independent of one another. Therefore, the shRNA stem and aptamer domains can be independently modified without altering the functionality of the opposing domain or requiring sequence reassignment.

Figure 1B:
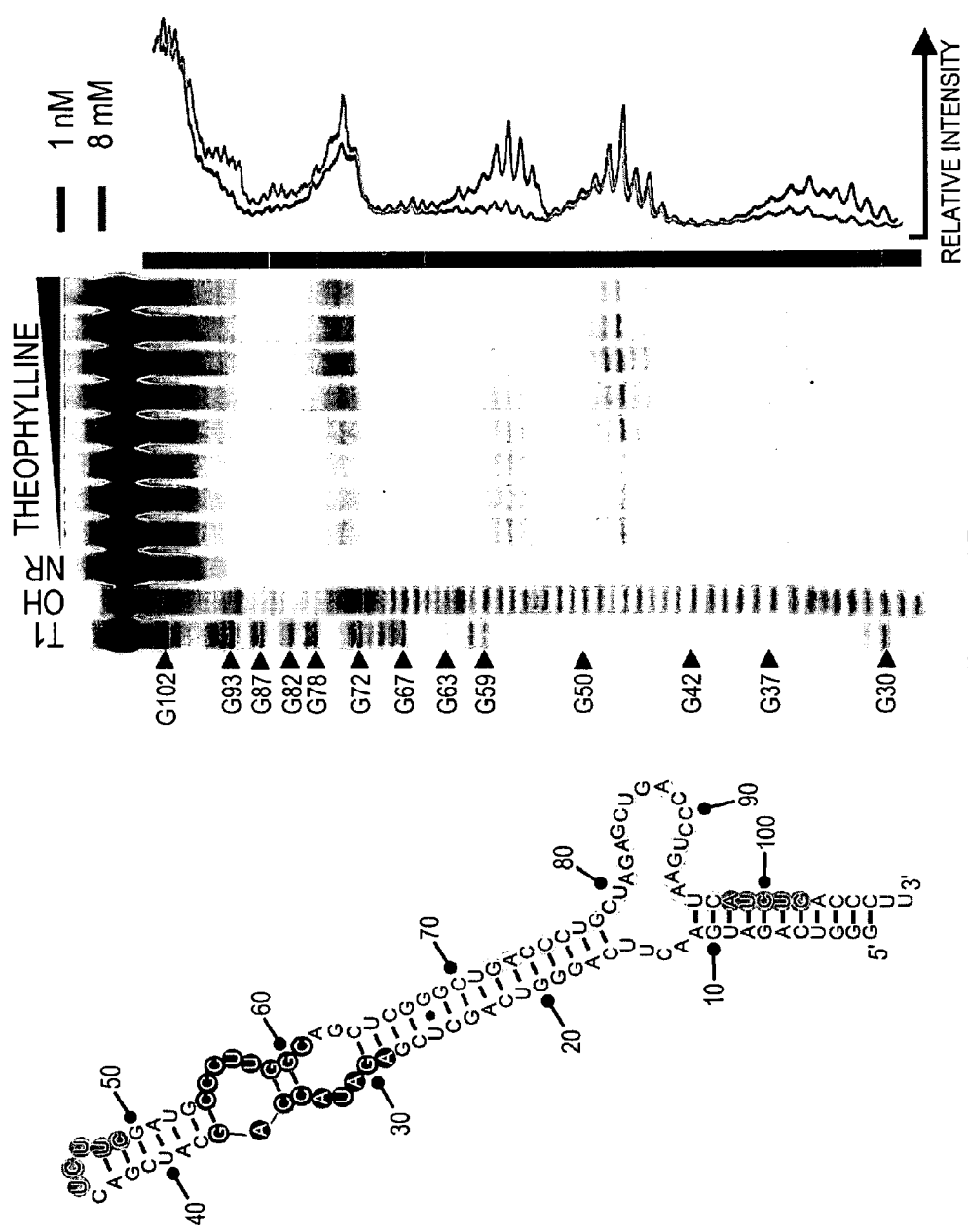

Applicants designed an initial shRNA switch (S1) to target EGFP and respond to theophylline by incorporating an EGFP-targeting guide strand and the theophylline aptamer (Zimmermann et al, 2000) into our switch platform (FIG. 1A). Applicants used in-line probing (Soukup and Breaker, 1999, incorporated herein by reference, and briefly described below) to assess the structural characteristics of a T7-transcribed variant similar to S1 (S4t; FIG. 1B). In-line probing provides structural information from the ligand dependence of spontaneous RNA cleavage. See Materials and Methods section below.

For increasing theophylline concentrations, stabilization of the aptamer domain coincided with destabilization of the switching strand and the downstream shRNA stem sequence. The results suggest that theophylline binding promotes structural changes within and outside of the aptamer domain. The apparent dissociation constant ($K_D$) of ~5 µM, which was determined by quantifying the cleavage products at two positions (FIG. 7), is an order-of-magnitude larger than that of the aptamer alone ($K_D$≈0.29 µM) (Zimmermann et al, 2000). The observed increase in $K_D$ is in agreement with the proposed mechanism (see below), where only the inactive conformation provides a formed aptamer that can bind ligand. Since shRNA switches can occupy both conformations, the apparent affinity will be lower because ligand can only bind the inactive conformation that is transiently present in a fraction of the shRNA switch population.

Figure 1C:
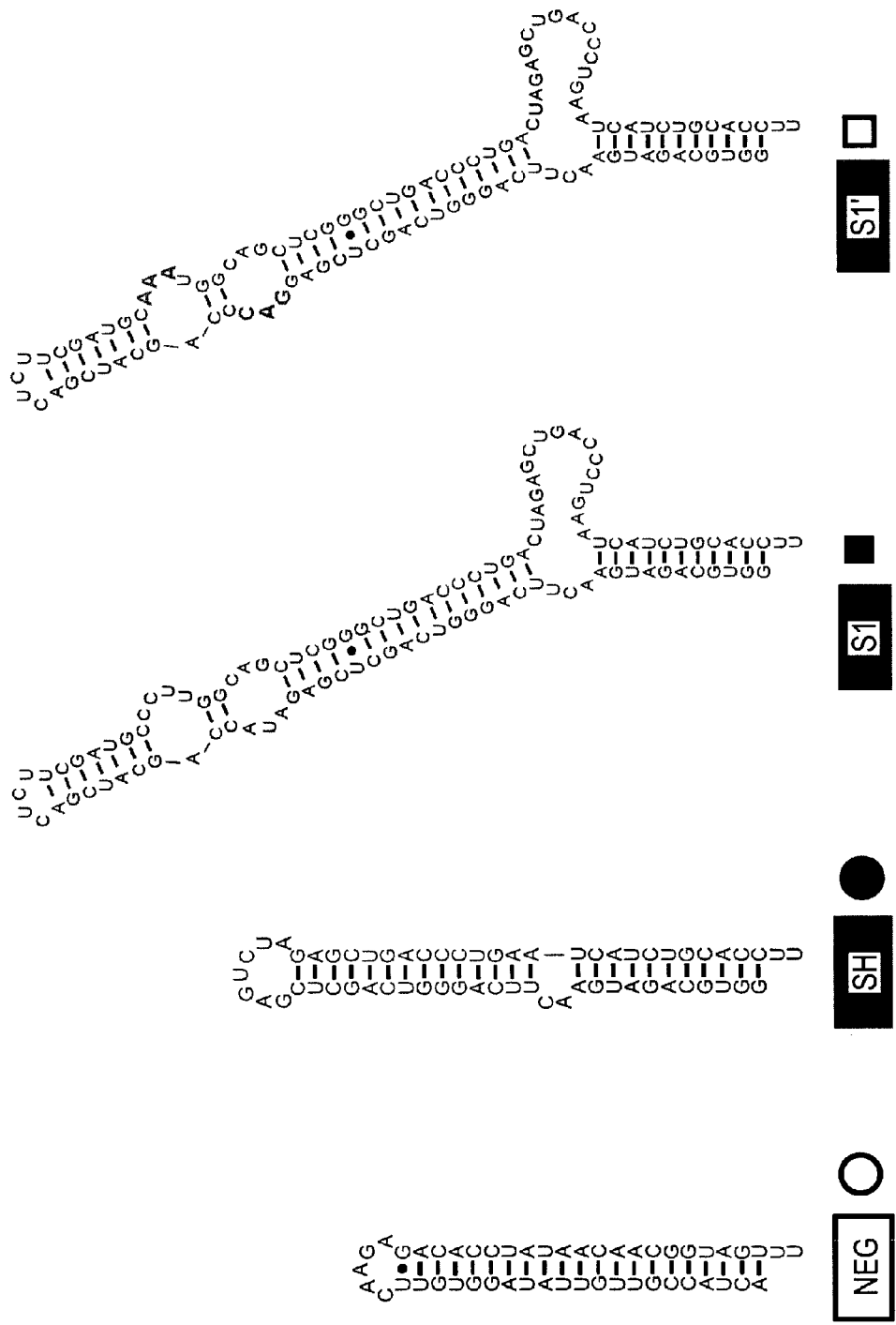

The functionality of shRNA switches was assessed in mammalian cell culture. Applicants transiently transfected plasmids harboring S1 and various switch controls transcribed from a U6 promoter into HEK293T cells stably expressing EGFP (Abbas-Terki et al, 2002). Flow cytometry analysis revealed that S1 elicits intermediate knockdown of EGFP as compared to the original shRNA targeting EGFP (sh) and a scrambled shRNA (neg) (FIGS. 1C & 1D), where the observed silencing by S1 can be attributed to activation of RNAi based on antisense inhibition of guide strand activity (Hutvagner et al, 2004; Meister et al, 2004) (FIG. 8). In the presence of theophylline, GFP levels increased in a dose-dependent manner for S1 but not for the control shRNAs. The effective concentration to achieve 50% activity ($EC_{50}$) for S1 of ~300 µM was much larger than the $K_D$ of 5 µM measured in vitro, which can be primarily attributed to a concentration drop in theophylline across the cellular membrane (Koch, 1956) (J Liang, J Michener, C Smolke, unpublished data, 2007). Mutating the aptamer core of S1 (S1') greatly reduced the observed theophylline dependence without perturbing basal expression levels.

Figure 1D:
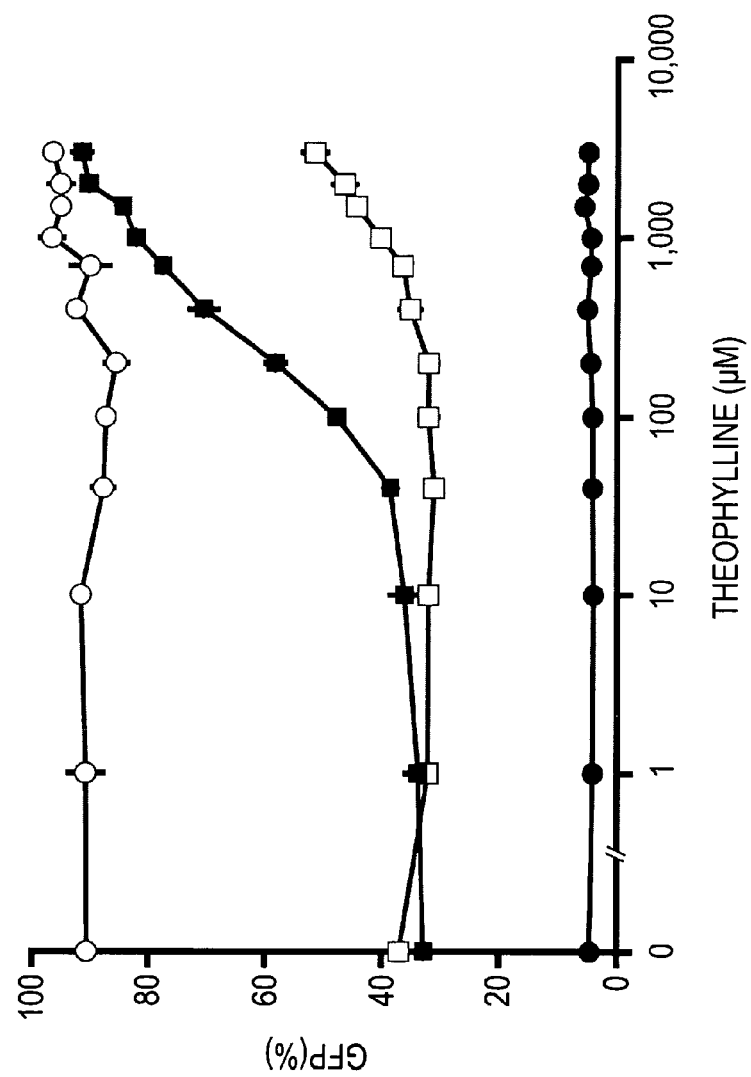

Taken together, S1 links theophylline concentration to GFP levels in vivo through a relationship described by a component transfer function (FIG. 1D). Applicants obtained qualitatively similar results when shRNA switches targeting EGFP were transiently transfected into other cell lines (FIG. 9), suggesting that shRNA switches can be broadly applied in different cell lines and types.

Example 2

Mathematical Modeling Offers Tuning Parameters to Predicatively Modulate Component Transfer Functions In this example, Applicants systematically evaluated the tuning capabilities of shRNA switches with the aid of a mathematical model relating ligand concentration and target gene expression levels. Standard model parameters were incorporated to represent each chemical step from the proposed mechanism (Example 7). Applicants assumed the two adopted conformations are at thermodynamic equilibrium, ligand only binds the inactive conformation, and the active conformation is solely processed to a siRNA with a reduced efficiency as compared to the original shRNA. These assumptions yield the following relationship between relative expression levels of the target gene (f; output) and exogenous ligand concentration (L; input):

$$f = 1 - e \cdot f_{shRNA}[1 + K_{Comp}(1 + K_{Apt} \cdot L)]^{-h}, \quad (1)$$

where e is the processing efficiency, $f_{shRNA}$ is the relative knockdown achieved by the original shRNA (sh), $K_{Comp}$ is the partitioning coefficient between active and inactive conformations, $K_{Apt}$ is the association constant for binding between ligand and the formed aptamer, and h is the hill coefficient to account for nonlinearity between siRNA concentration and target expression levels.

Figure 2A:
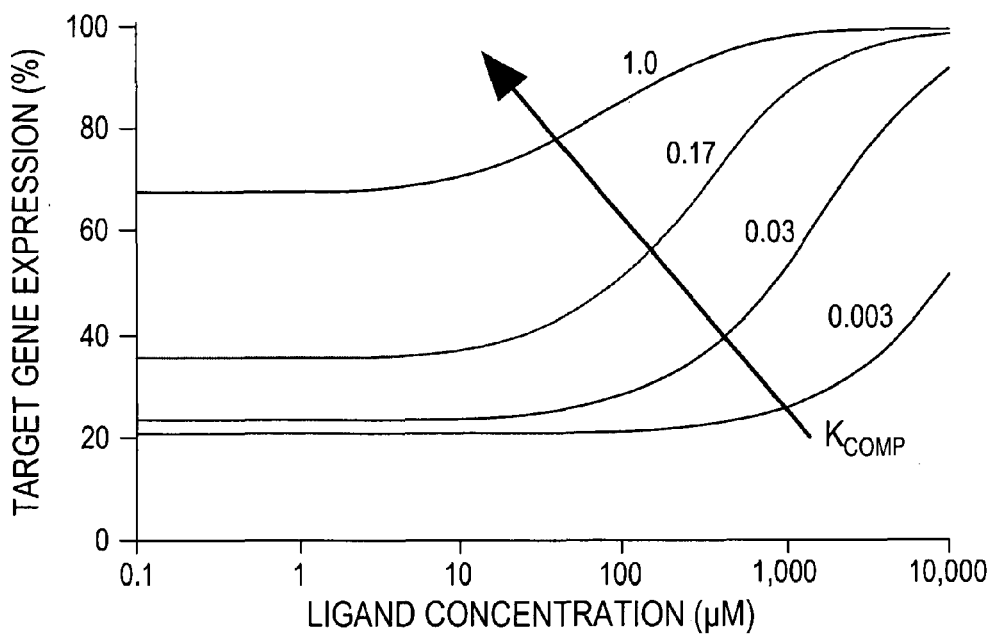
Figure 2B:
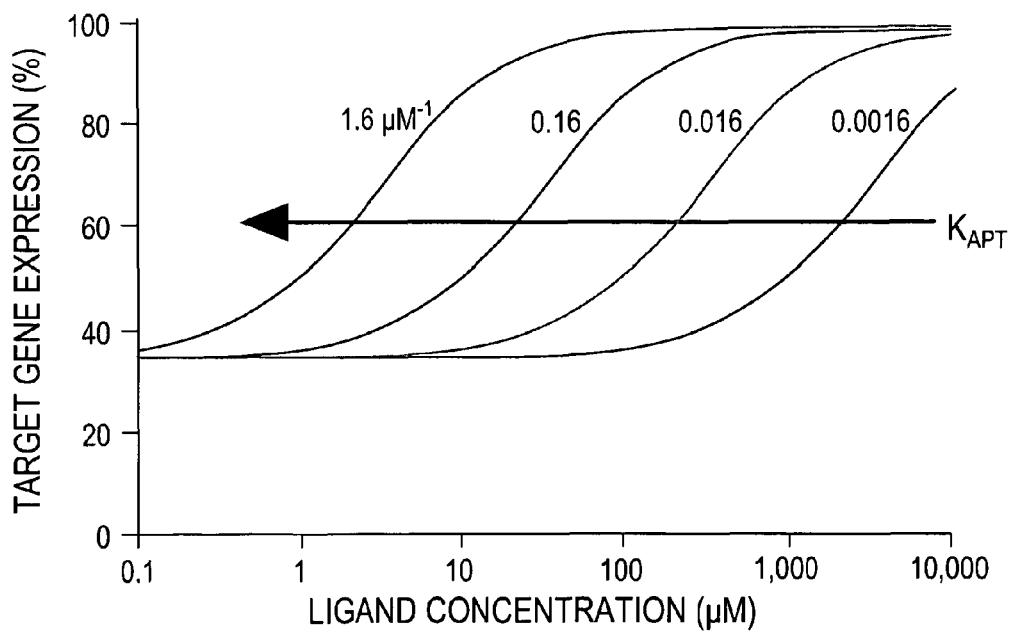
Figure 2C:
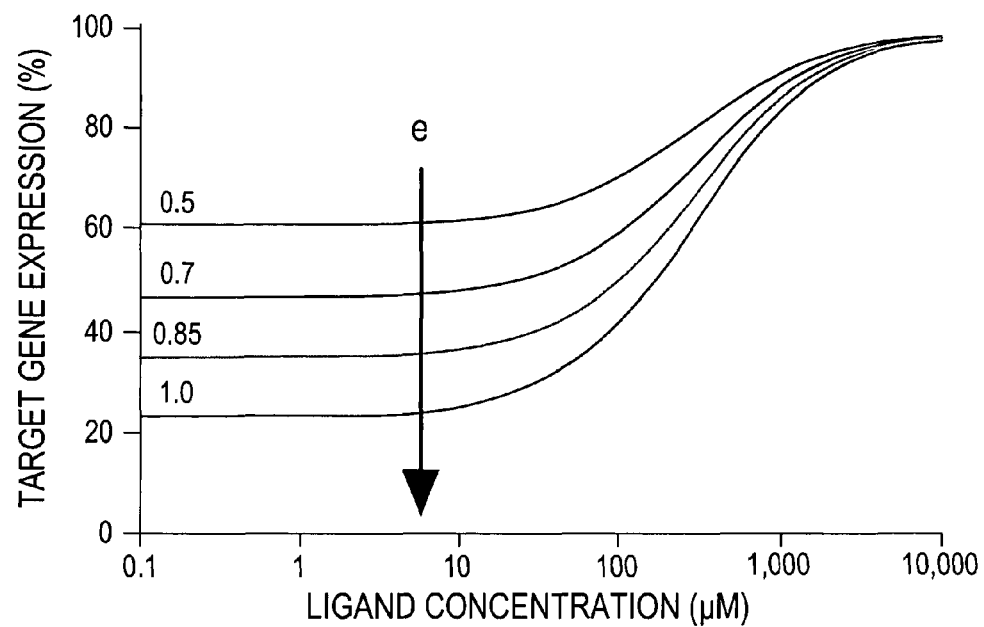
Figure 2D:
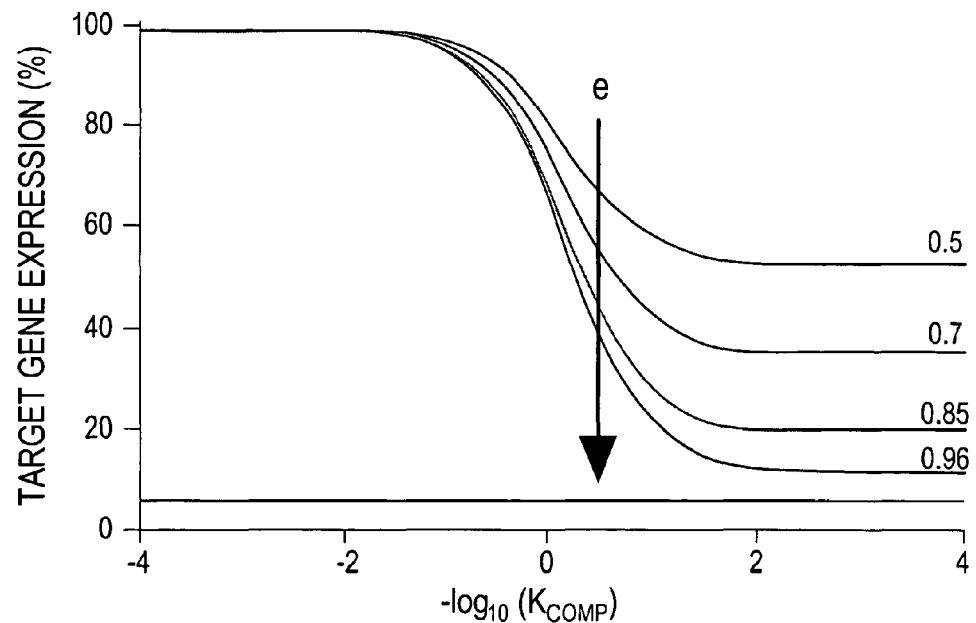
Figure 3A:
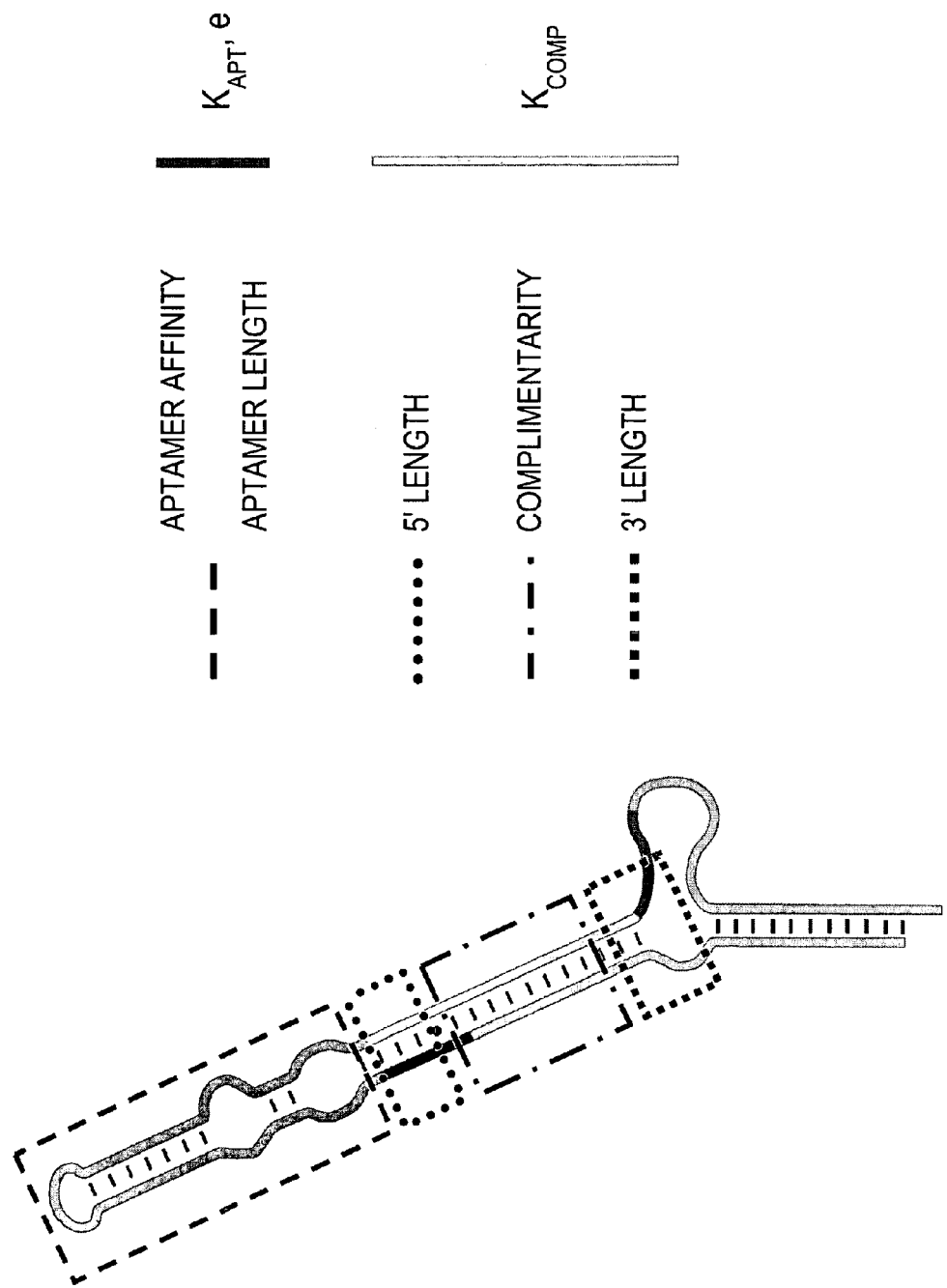
Figure 3B:
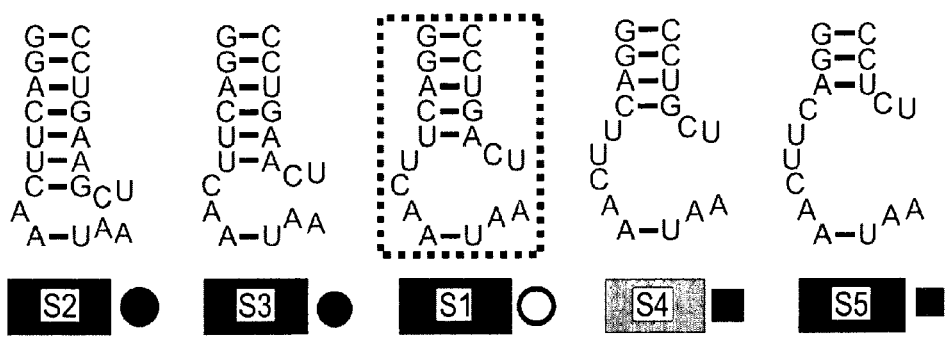
Figure 3C:
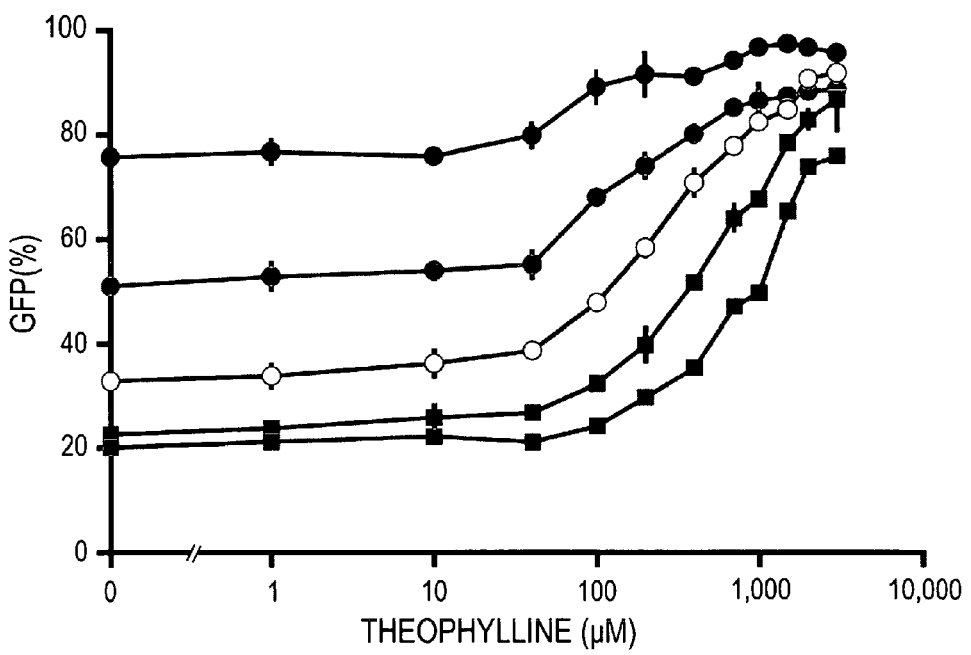
Figure 3D:
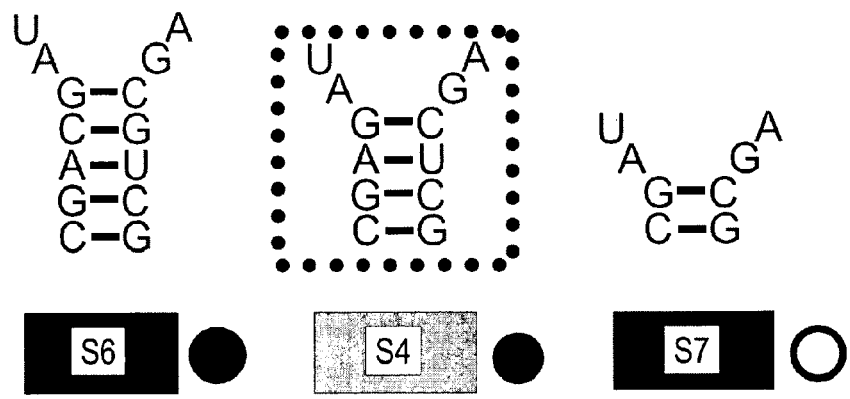
Figure 3E:
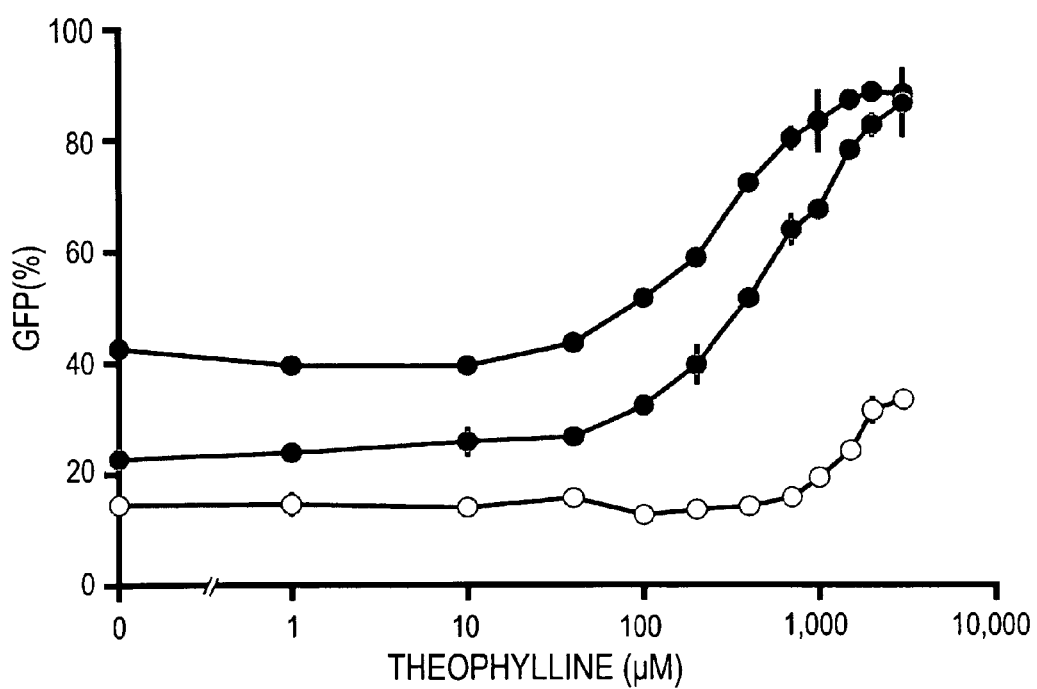

While complicated mathematical models have been developed for RNAi (Bartlett and Davis, 2006; Malphettes and Fussenegger, 2006; Raab and Stephanopoulos, 2004), the approach utilizes a minimal parameter set that is experimentally tractable, fully represents RNAi in the context of shRNA switches, and captures the steady-state behavior of the system (FIG. 10). For one shRNA stem sequence and input ligand (fixed $f_{shRNA}$, h), the model provides three tuning parameters that can be varied to tune the component transfer function: $K_{Comp}$, $K_{Apt}$, and e (FIGS. 2A-2C). Varying $K_{Comp}$ results in a concomitant and opposing variation in $EC_{50}$ and basal expression levels, which are independently tuned by $K_{Apt}$ and e, respectively. In addition, as $K_{Comp}$ approaches zero, basal expression levels approach a lower limit that is dependent on the value of e and is higher than that of the original shRNA (FIG. 2D). Since each tuning parameter represents individual steps in the proposed mechanism, Applicants examined how modifying the sequence in each domain, specifically the switching strand and aptamer domains, corresponds to parameter variation in order to identify unique tuning strategies (FIG. 3A).

Example 3

Figure 3F:
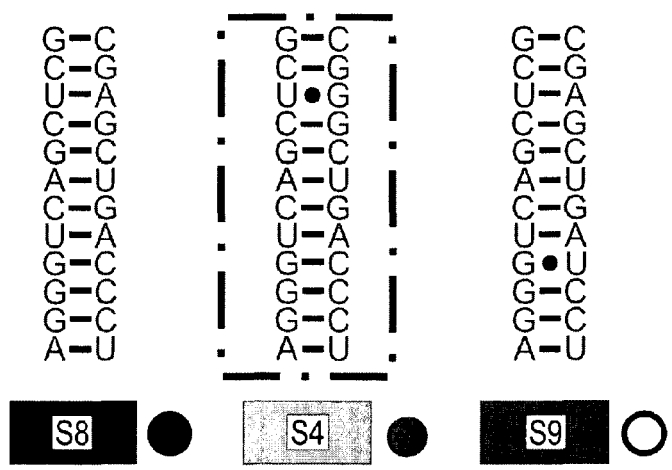
Figure 3G:
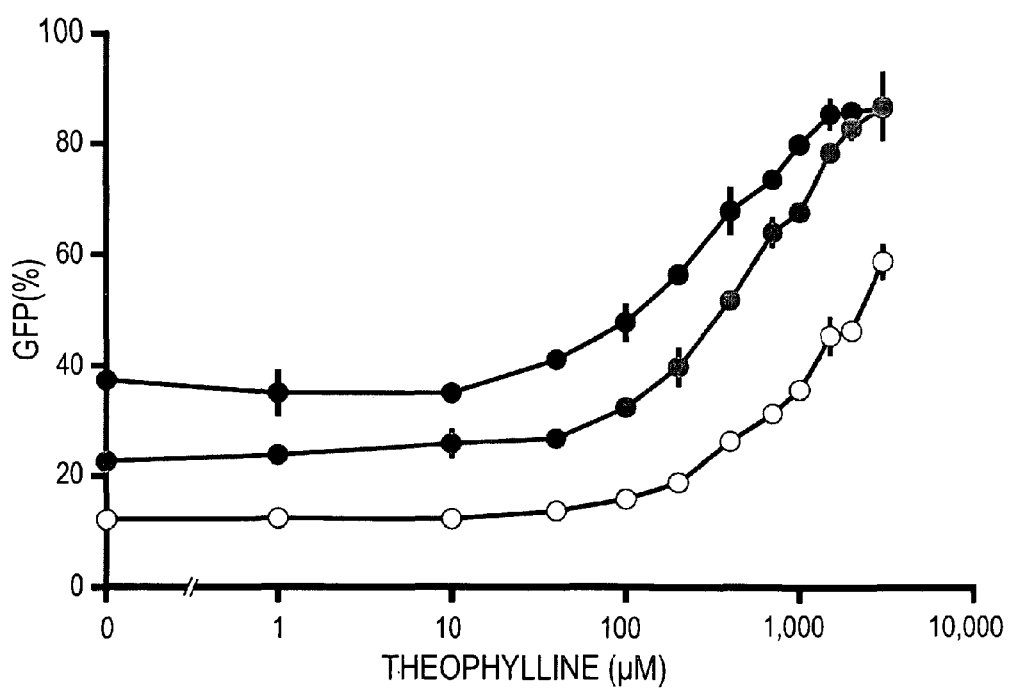

Switching Strand Tuning Strategies Enable Predictive Alteration of the Component Transfer Function Modifying switching strand base-pairing interactions is anticipated to reflect changes in $K_{Comp}$, since this parameter represents the thermodynamic partitioning between active and inactive conformations. Applicants developed switching strand tuning strategies to target modifications to three regions within the switching strand domain: the length of the switching strand on the 3' end (FIGS. 3B & 3C) or the 5' end (FIGS. 3D & 3E), or the base-pairing complementarity (FIGS. 3F & 3G). Applicants introduced iterative nucleotide changes under each switching strand tuning strategy and generated component transfer functions as before. Regardless of the selected strategy, each nucleotide change resulted in a shift in the response curve in line with the model prediction for variation in $K_{Comp}$. The results suggest that decreasing the extent of base-pairing interactions between the switching strand and the shRNA stem decreases the stability of or bias toward the inactive conformation (lower $K_{Comp}$), resulting in lower basal expression levels and a higher $EC_{50}$. The trend towards higher $EC_{50}$ is consistent with the order-of-magnitude difference between the apparent $K_D$ of S1 observed in the in-line probing experiment and that reported for the aptamer alone (FIG. 1B). Thus, sequence modifications to the switching strand that affect the extent of base-pairing solely map to variation of $K_{Comp}$.

Example 4

Figure 4A:
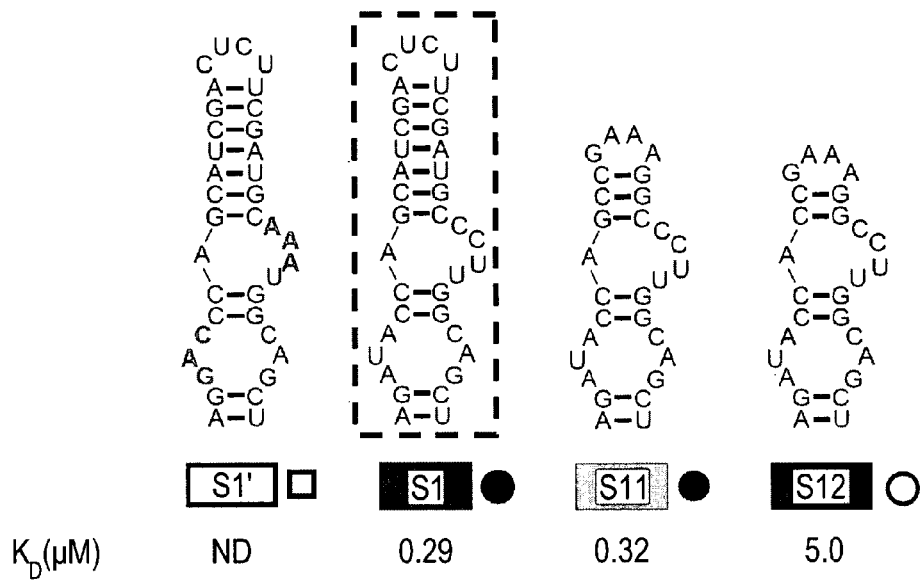
Figure 4B:
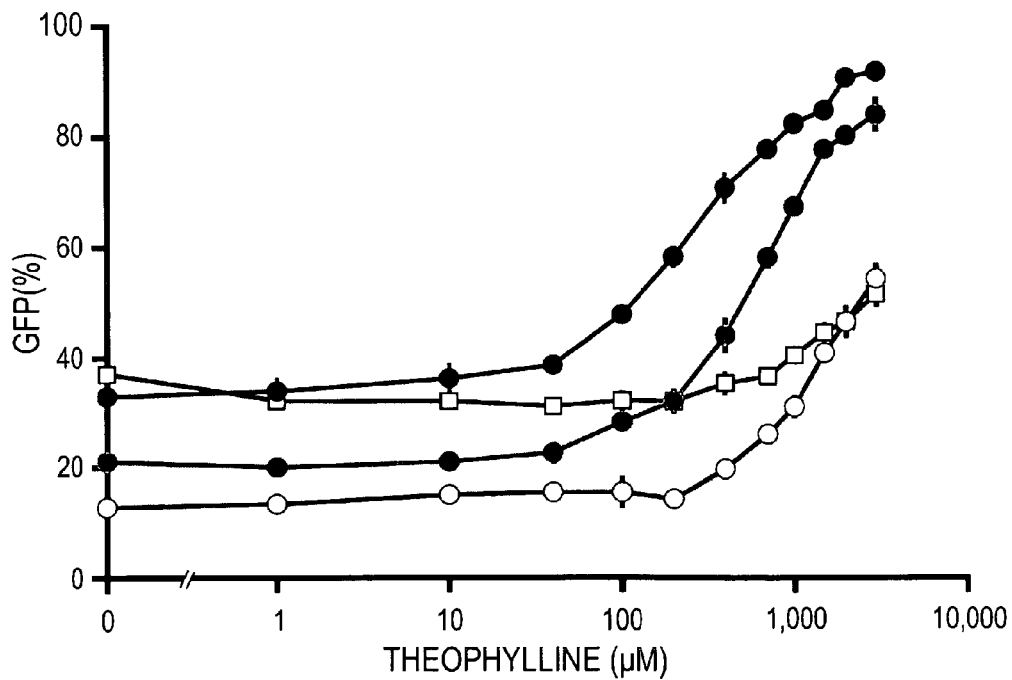

Aptamer Tuning Strategies Enable Predictive Alteration of the Component Transfer Function Although ligand binding to the formed aptamer directly relates to aptamer affinity, represented by $K_{Apt}$, sequence changes in the aptamer domain may affect other parameters. To evaluate how sequence modification of the aptamer domain corresponds to parameter variation, Applicants tested two theophylline aptamer variants (S11 and S12) with dissimilar $K_D$ values (Zimmermann et al, 2000) and the mutated aptamer (S1') (FIGS. 4A & 4B). Mutating the aptamer core (S1') without perturbing shRNA switch secondary structure or sequence length resulted in a shift in $EC_{50}$, whereas decreasing aptamer affinity by decreasing the aptamer stem length (S11 and S12) resulted in a shift in both $EC_{50}$ and basal expression levels. The shifts in $EC_{50}$ for S11 and S12 matched the relative $K_D$ measured in vitro for the aptamer variants alone (Zimmermann et al, 2000), suggesting that modulating aptamer affinity is reflected by variation in $K_{Apt}$. However, $K_{Apt}$ only affects $EC_{50}$, suggesting that either $K_{Comp}$ or e varies with aptamer size. Since the switching strand sequence is preserved for S1, S1', S11, and S12, Applicants hypothesized that the shift in basal expression levels independent of $K_{Apt}$ (most obvious in comparing the transfer functions of S1 and S11) is solely attributed to the third tuning parameter e (FIG. 2C).

Figure 4C:
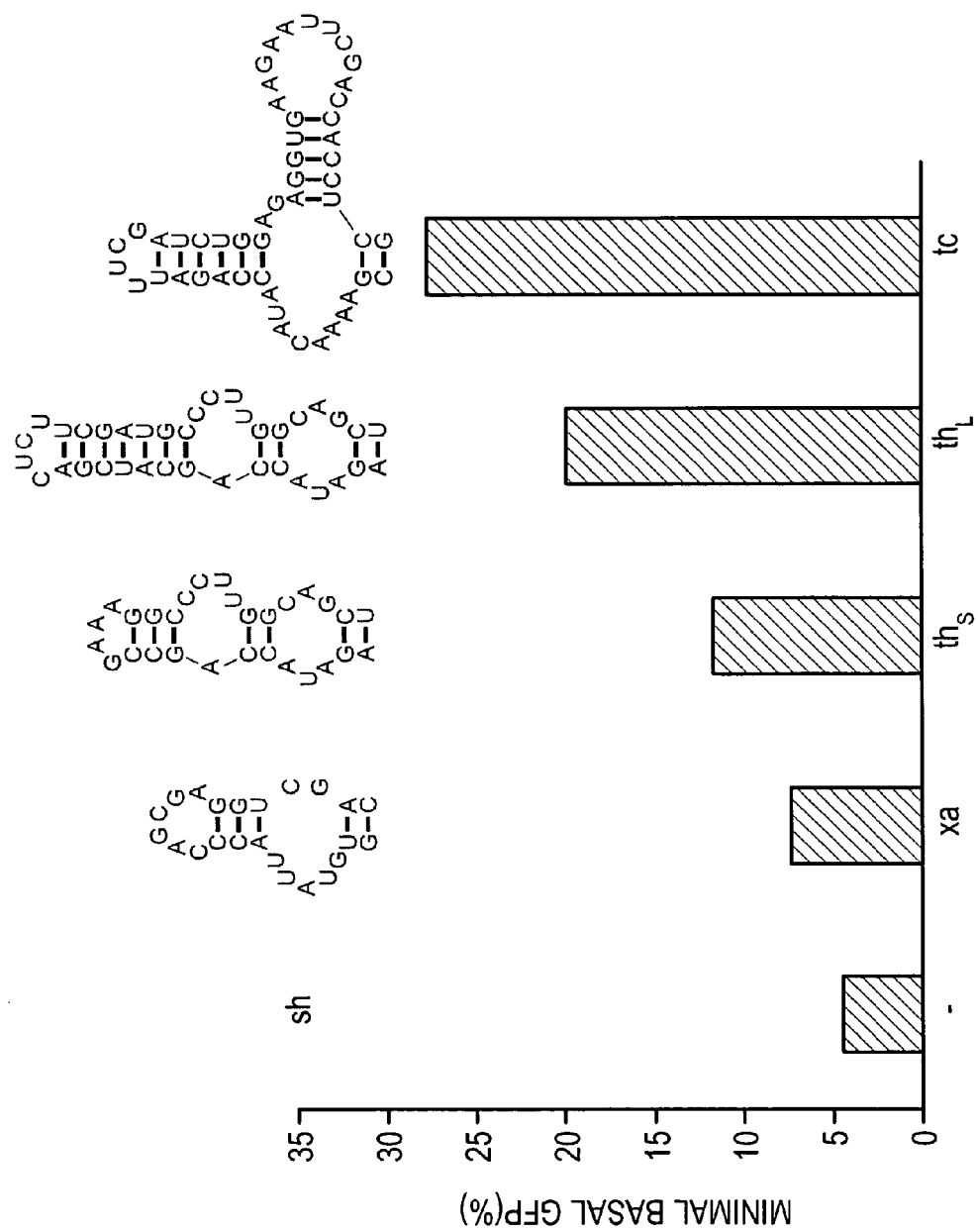

To evaluate the relationship between aptamer size and the tuning parameter e, Applicants replaced the theophylline aptamer with the smaller xanthine aptamer (Kiga et al, 1998) or the larger tetracycline aptamer (Berens et al, 2001). Since variation of e and $K_{Comp}$ both affect basal expression levels, sole evaluation of e requires estimation of the lower limit of basal expression levels for vanishingly small values of $K_{Comp}$ (FIG. 2D). To this end, Applicants constructed at least one shRNA switch with each aptamer that strongly prefers the active conformation (low $K_{Comp}$; see below) and measured GFP basal expression levels of cells transfected with these constructs (FIG. 4C). Assay results indicated that aptamer size strongly correlated with the lower limit of basal expression levels. The results suggest that the tuning parameter e, which is predicted to have a significant effect on the lower limit of basal expression levels, maps to the size of the aptamer domain.

These observations led to the specification of two general aptamer tuning strategies: targeted changes in aptamer affinity without changing aptamer size alter $K_{Apt}$, and targeted changes to aptamer size to alter the processing efficiency of the switch (e). Taken together, variation of $K_{Apt}$ and e map to the aptamer domain and depend on the nature of the sequence modification.

Figure 4D:
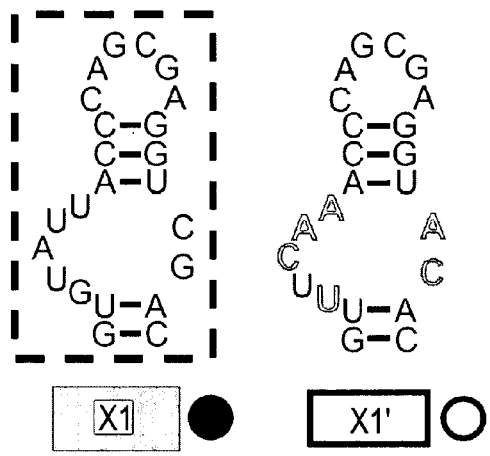
Figure 4E:
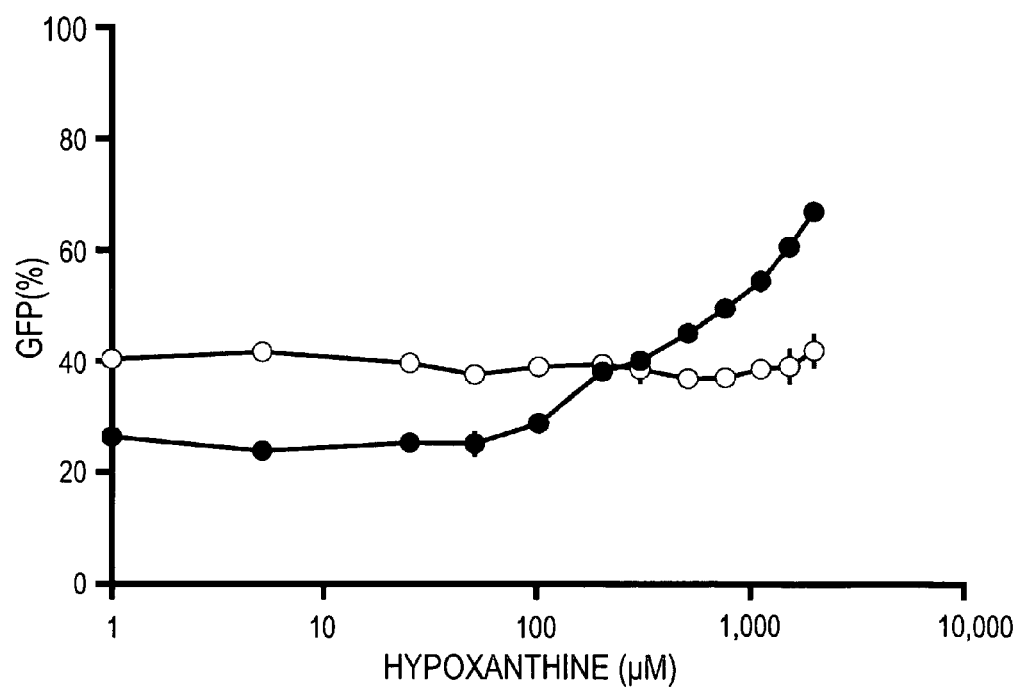
Figure 4F:
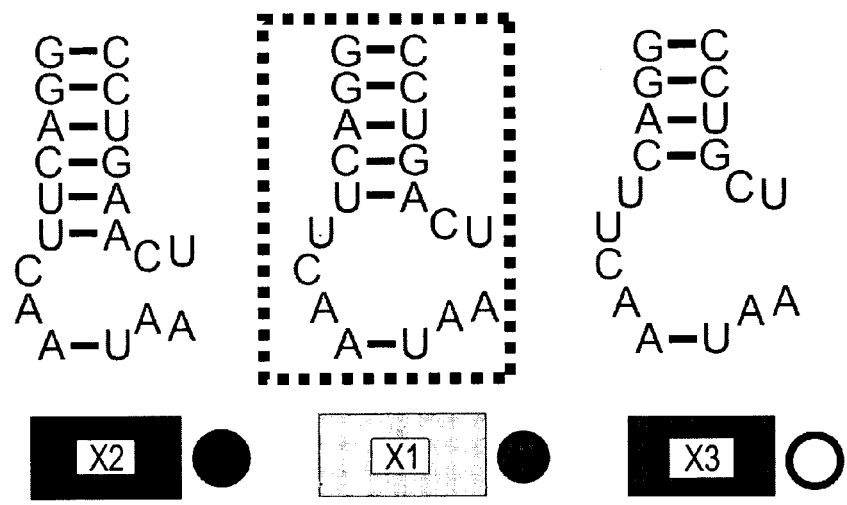
Figure 4G:
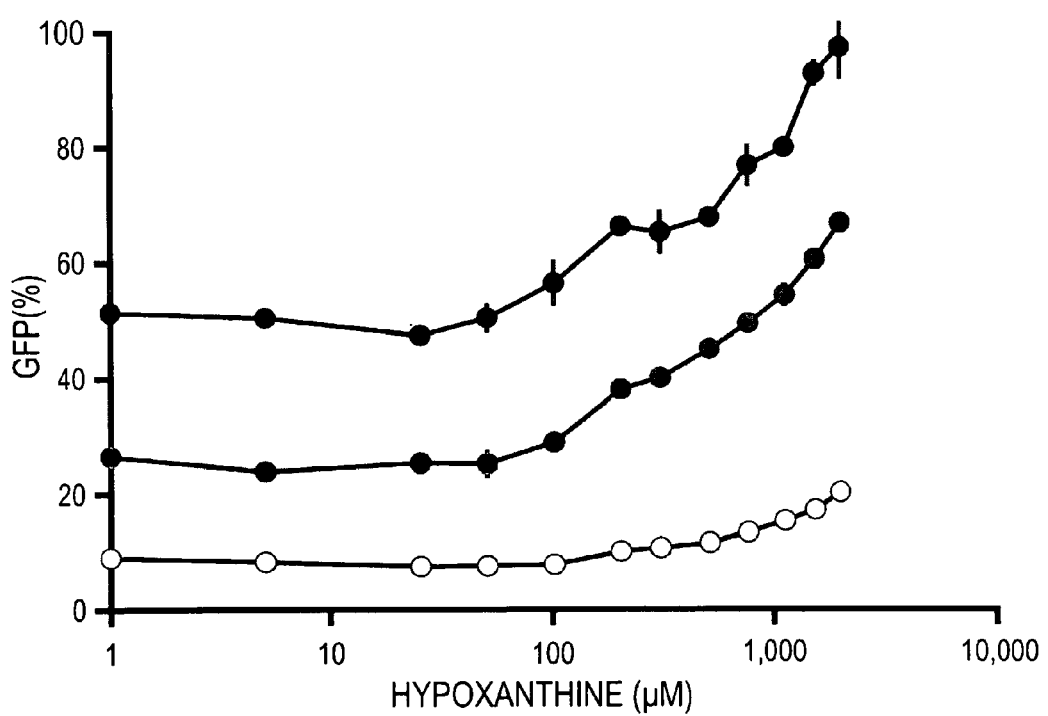

Applicants also examined whether placement of new aptamers into the aptamer domain imparts new ligand dependence while preserving shRNA switch functionality. Previous RNA-based regulatory platforms have demonstrated alteration of ligand dependence by the modular incorporation of new aptamers (Bayer et al, 2005; Win et al, 2007) or minimal mutation of the base aptamer (Desai and Gallivan, 2004; Thompson et al, 2002). Applicants evaluated the xanthine aptamer, since it produced low basal expression levels and tightly binds the water soluble and non-cytotoxic small molecule hypoxanthine. Following construction of shRNA switches that incorporate the xanthine aptamer by direct replacement of the aptamer domain, Applicants generated component transfer functions in HEK293T cells stably expressing EGFP. As observed for S1, intermediate basal expression levels of GFP increased in a dose-dependent manner that was abolished by mutating the aptamer core (FIGS. 4D & 4E). Contrary to model predictions, mutation of the xanthine aptamer increased the basal expression levels, which may be attributed to base pairing interactions with other shRNA switch domains. However, the shift in basal levels is less than that observed for changes in the switching strand, suggesting that our model serves as a sufficient first approximation. Furthermore, the switching strand tuning strategies were preserved as evidenced by the effect of changing the switching strand length on the hypoxanthine response curves (FIGS. 4F & 4G). Thus, the subject shRNA switch design can accommodate different aptamers to alter the identity of the molecular input that regulates gene expression.

Example 5

Programming Transfer Functions by Combining Switching Strand or Aptamer Tuning Strategies The ligand-regulated behavior of shRNA switches can be programmed through application of the switching strand and aptamer tuning strategies described above. By combining these programming strategies, a collection of shRNA switches could be constructed that display finely tuned transfer functions and respond to a range of molecular inputs.

Based on the independence of the switching strand tuning strategies, Applicants first examined whether the strategies can be combined to fine tune the component transfer function beyond the capabilities of any single strategy. To generate small deviations in the transfer function of a parent shRNA switch, Applicants added compensatory nucleotide changes under each switching strand tuning strategy in a step-wise manner (FIGS. 5A & 5B): a point mutation (G68A) within the switching strand to increase complementarity, deletion of two base-pairs to decrease the switching strand length at the 5' end, and a single insertion at the 3' end to increase the switching strand length. Each nucleotide change yielded the expected shift in the transfer function corresponding to the relative stabilization (increased $K_{Comp}$) or destabilization (decreased $K_{Comp}$) of the inactive conformation. The final switch, S10, displayed a transfer function slightly shifted from that of the parent switch, S4, demonstrating that nucleotide changes following the three switching strand tuning strategies can be combined to yield fine tuning of the component transfer function.

Example 6

Figure 6A:
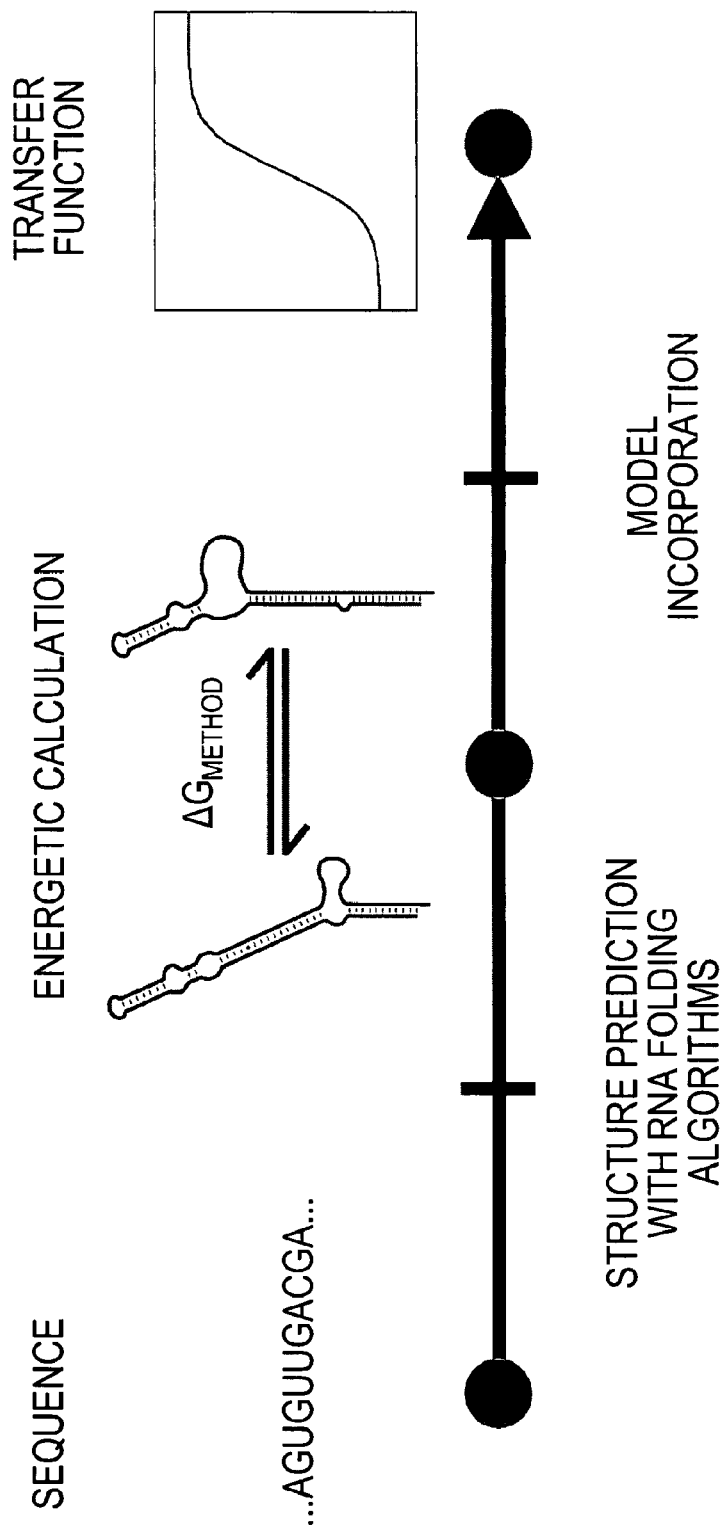

An In Silico Framework Towards Component Sequence-to-Transfer Function Prediction The construction of large-scale biological systems will require the simultaneous optimization of the behavior of all system components to yield proper network behavior as suggested for natural (Suel et al, 2007) and synthetic (Gardner et al, 2000; Yokobayashi et al, 2002) systems. While the transfer functions associated with shRNA switches and other synthetic riboswitches are amenable to physical tuning based on actual in vitro or in vivo experiments, a computational framework to effectively navigate qualitatively functional sequences is necessary for the rapid optimization of switch performance. Folding energetics dictate conformational partitioning and therefore switch performance for a strand displacement mechanism. RNA secondary structure prediction algorithms, such as that described in Mathews et al (2004, incorporated herein by reference) have the potential to perform accurate in silico prediction of in vivo switch performance, although these algorithms have not been sufficiently tested for in vivo folding dynamics. To investigate the applicability of the secondary structure algorithms to predict in vivo switch behavior, Applicants sought to develop a sequence-to-function relationship for switches using such algorithms in combination with our model (FIG. 6A). For convenience, shRNA is again used as an illustrative model, although the same principle and general methodology applies to other switch platforms (such as a ribozyme-based switch platform) as well.

Based on the tuning analysis above, Applicants identified $K_{Comp}$ as the sole parameter that reflects partitioning between active and inactive conformations and maps to the switching strand. The free energy difference ($\Delta G$) between conformations is directly related to $K_{Comp}$ such that transfer function prediction is possible by calculating $\Delta G$ from sequence information with the aid of structure prediction algorithms, converting this value into $K_{Comp}$, and inserting $K_{Comp}$ into equation (1) (see Example 2) to quantitatively relate ligand concentration (L) and target gene expression levels (f). A fully determined model requires values for the remaining model parameters; as these parameters are not currently amenable to calculation in silico, experimental estimation can be conducted with a minimal set of experiments based on our model construction. See Example 7 for derivation of the mathematical models.

Applicants first determined if $\Delta G$ values calculated from the algorithm correlate with the measured basal expression levels for shRNA switches with varying switching strand sequences. The implicit assumption is that switching strand alterations only affect conformational partitioning, which can be calculated with the structure prediction algorithms. Applicants evaluated $\Delta G$ ($\Delta G_{method}$) by separating active and inactive conformations based on the minimal free energy (MFE) and the weighted energies from a partition function (PF) calculation (see below and FIG. 12), where both methods are commonly used to evaluate RNA folding in vitro and in vivo. These methods were employed to calculate $\Delta G_{method}$ for shRNA switches S1-10, which differ only in their switching strand sequence. To measure the correlation strength between $\Delta G_{method}$ and basal expression levels for either method, Applicants performed a least-squares fit using a three-parameter equation of the same form as our model with both data sets. Ideally, the fit relationship between $\Delta G_{method}$ and measured basal expression levels should align with the same relationship predicted by the model (FIG. 6B), where $\Delta G$ ($\Delta G_{model}$ 1 is related to $K_{Comp}$ according to equation (3). However, both MFE and PF calculations failed to provide a significant correlation between $\Delta G_{method}$ and basal expression levels (FIG. 12), suggesting that these methods are insufficient for accurate prediction of RNA folding dynamics in vivo.

Figure 6B:
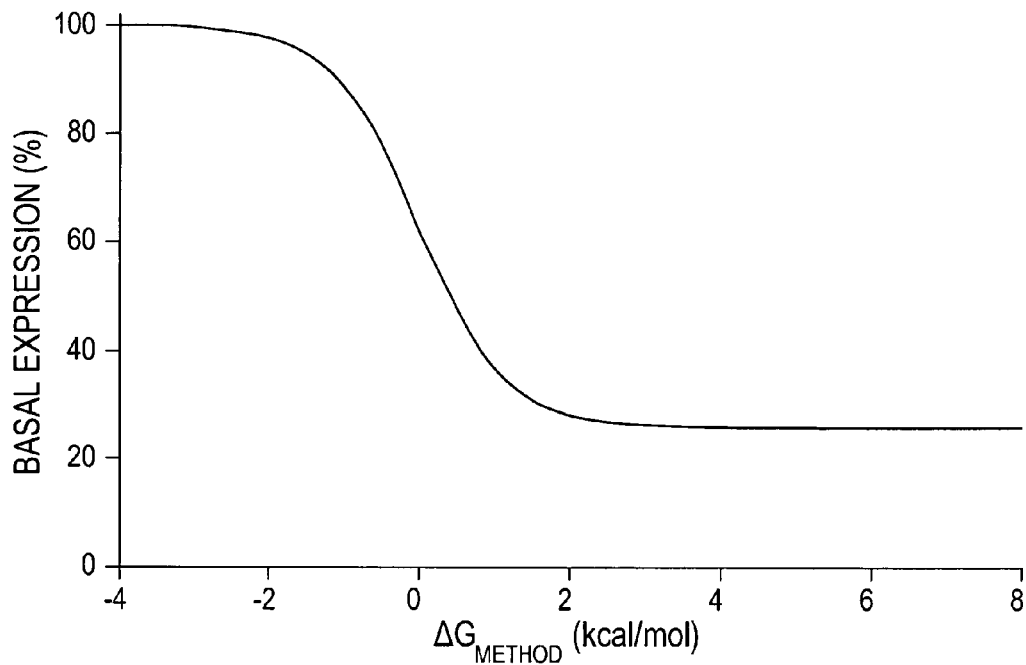
Figure 6C:
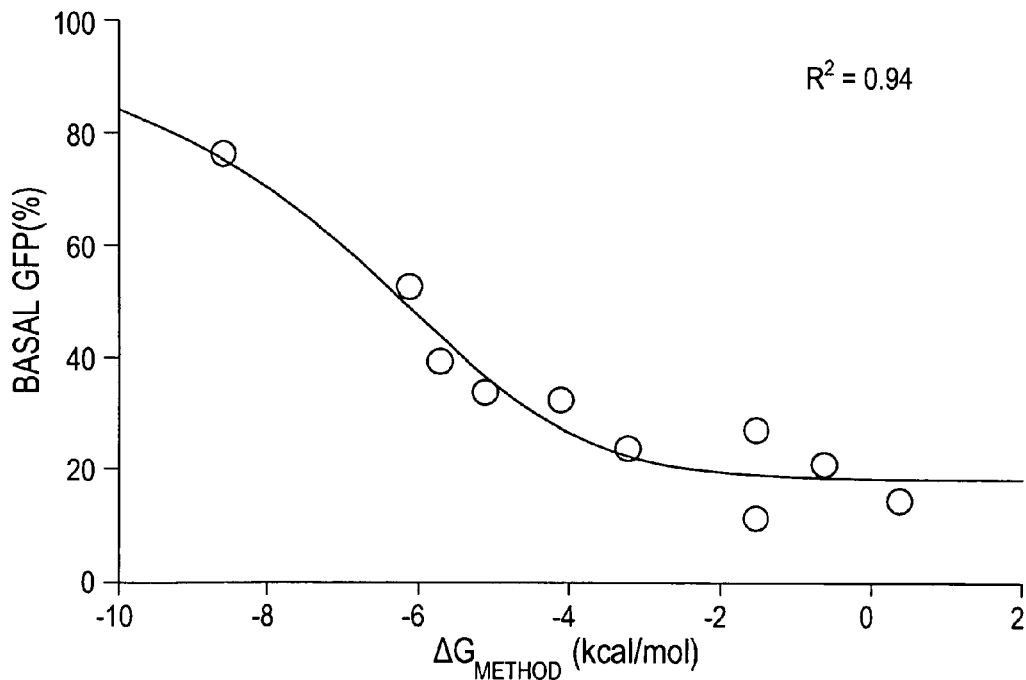

For all switching strand tuning strategies, increasing the stability of the inactive conformation always resulted in an increase in basal expression (FIGS. 3B-3G). The MFE and PFE methods did not effectively capture each energetic shift potentially due to the inclusion of binding interactions outside of the major stems. Applicants hypothesized that the interactions outside of the switching strand domain are less prevalent in vivo and are biasing the energetic calculations. To examine this possibility, Applicants devised a third method, the stems method, that only accounts for the energetics of the major stem in each conformation (FIG. 11). Implementing the stems method resulted in a strong correlation ($R^2=0.94$) between basal expression levels and $\Delta G_{method}$ (FIG. 6C).

Despite the absence of a perfect overlap between the stems method correlation and that predicted by our model (FIGS. 6B & 6C), the correlation established a significant empirical link between shRNA switch sequence and behavior in the absence of ligand. This correlation can be assimilated into the model by equating basal expression levels predicted by the fit equation and the model to determine the relationship between $\Delta G_{method}$ and $K_{Comp}$. See Example 8 for free energy calculations and model extension.

Doing so yields a predictive component transfer function that is now dependent on the calculated value of $\Delta G_{method}$:

$$f_{model} = \frac{1 - e \cdot f_{shRNA} \left[ 1 + \left[ \sqrt[h]{\frac{e \cdot f_{shRNA}}{C_1}} \left[ C_2 + \exp\left(-\frac{\Delta G_{method}}{k_B N_A T}\right) \right]^{C_3} - 1 \right] \right]^{-h}}{(1 + K_{Apt} \cdot L)} \quad (2)$$

where $C_{1-3}$ are empirical constants from the fit correlation. This extended model provides a general framework for predicting shRNA switch transfer functions from sequence information, where energetic values produced from structure prediction algorithms are inserted into the model for the prediction of switch behavior. While the extended model currently requires parameter fitting to yield the predicted relationship between ligand concentration and target gene expression levels, the framework establishes a starting point for the development of methods that rely on in silico calculations for transfer function prediction from sequence information.

Example 7

Derivation of Mathematical Model

Applicants developed a mathematical model to examine the mechanism through which shRNA switches mediate ligand control of RNA interference (RNAi). Instead of drawing from existing models (Bartlett and Davis, 2006; Malphettes and Fussenegger, 2006; Raab and Stephanopoulos, 2004) that take into account the mechanistic steps and kinetics of RNAi that are well characterized, Applicants chose to derive a simplified model that captures the steady-state behavior of shRNA switches and the fundamental mechanism that provides for ligand regulation of gene expression. The goal was to develop a model that predicts the relative steady-state expression levels of the target gene (f; output) as a function of exogenous ligand concentration (L; input), and can be easily adapted to predict shRNA switch activity in different cellular environments.

To accomplish this, Applicants began with the proposed mechanism for shRNA switch functionality (FIG. 1A). This mechanism asserts that a single shRNA switch can adopt two conformations due to distinct base-pairing interactions. The active conformation (left) is processed by the RNAi machinery to an siRNA that initiates RNAi-mediated silencing of target transcripts. Processing includes nuclear export by Exportin-5 (Yi et al, 2003) and cleavage by the RNase III-like enzyme Dicer (Ketting et al, 2001). Conversely, the inactive conformation (middle) is not processed by the RNAi machinery. Ligand binding to the formed aptamer domain in the inactive conformation stabilizes this conformation (right), thereby reducing overall processing of the shRNA switch to an siRNA.

Model derivation began by assuming that the three conformations (active, inactive, and inactive bound to ligand) are at thermodynamic equilibrium as determined by $K_{Comp}$ and $K_{Apt}$. $K_{Comp}$ is the equilibrium partitioning coefficient between active and inactive conformations, while $K_{Apt}$ is the association constant for binding between ligand and the inactive conformation. When normalized to the total shRNA switch concentration, the fraction of shRNA switches in the active conformation is:

$$[\dagger] = \frac{1}{1 + K_{comp}(1 + K_{apt} \cdot L)}. \tag{1}$$

The next step was correlating the fraction of shRNA switches in the active conformation to relative expression levels of the target gene. Previous models have highlighted the importance of absolute expression levels of the RNAi substrate, target gene transcripts, and the RNA-induced silencing complex (RISC), as well as the rate of cell division (Bartlett et al, 2006). Recent work has elaborated on the mechanism of RNAi, including the emerging role of Dicer binding partners TRBP and PACT (Gregory et al, 2005; Kok et al, 2007; Lee et al, 2006), association of RISC and Dicer (Gregory et al, 2005), shuttling of the cleaved siRNA from Dicer to RISC (Gregory et al, 2005), cleavage and release of the passenger strand (Matranga et al, 2005; Rand et al, 2005), target site availability for efficient degradation of the target transcript (Westerhout and Berkhout, 2007), and the potential for saturation of Exportin-5 (Grimm et al, 2006; Yi et al, 2005). Rather than offer a descriptive model of RNAi that incorporates all of these mechanisms that are still under investigation, we chose an empirical route that requires minimal experimental data.

Excluding nuclear export by Exportin-5, the mechanistic steps described above apply to the linear cascade downstream of and including Dicer recognition and processing. Incorporation of three parameters, $f_{shRNA}$, e, and h, can account for the dynamics of these steps. $f_{shRNA}$ is the relative knockdown achieved by the original shRNA—an RNA molecule comprised of a loop region and the shRNA stem sequence, e is the efficiency of shRNA switch processing by the RNAi machinery, and h is the hill coefficient that accounts for the nonlinearity between the concentration of Dicer-cleaved siRNAs and relative expression levels of the target gene. To capture the correlation between the prevalence of the active conformation and target gene expression levels, we used the following relationship:

Introducing equation (1) into equation (2) yields the final form of the model:

$$f = 1 - e \cdot f_{shRNA} [1 + K_{Comp}(1 + K_{Apt} \cdot L)]^{-h} \tag{3}$$

where the relative expression levels of the target gene (f) are a function of exogenous ligand concentration (L).

The power of this model lies in the ability to calculate realistic parameter values from a minimal set of experiments: $f_{shRNA}$ can be found in one experiment by measuring the relative knockdown of the target gene induced by an shRNA that contributes the shRNA stem, e can be calculated from basal expression levels from a few shRNA switches that strongly prefer the active conformation, and h can be calculated by generating a ligand response curve with one shRNA switch—as long as administration of the highest ligand concentration results in negligible knockdown of the target gene. The remaining model parameters, $K_{Comp}$ and $K_{Apt}$, can be found from the same response curve used to calculate e, since varying $K_{Apt}$ only changes the $EC_{50}$ while varying $K_{Comp}$ changes both $EC_{50}$ and basal expression levels. A summary of the model parameters and how values are experimentally obtained are included in Table III below.

TABLE III

Description of model parameters

| parameter | initial determination | description |
|---|---|---|
| $K_{Comp}$ | fit to data | Equilibrium constant between active and inactive conformations (—) |
| $K_{Apt}$ | fit to data | Association constant between ligand and formed aptamer (1/μM) |
| e | extrapolated from data | RNAi processing efficiency (—) |
| $f_{shRNA}$ | from shRNA data | Relative knockdown by original shRNA (—) |
| h | fit to data | Hill coefficient (—) |

To investigate the validity of the model, Applicants experimentally determined model parameter values as described above: $f_{shRNA}$ was equated to the knockdown achieved with the original shRNA targeting EGFP (sh); e was calculated from the average basal expression levels produced by shRNA switches S5, S7, S9, and S10; and $K_{Comp}$, $K_{Apt}$, and h were determined by a model fit of the theophylline response curve for S1. The resulting parameter values are shown in FIG. 10. The fit curve aligns with the response curve for S1, and the fit parameter values are realistic as described below for $K_{Apt}$ and $K_{Comp}$. The $EC_{50}$ is related to $K_{Apt}$ and $K_{Comp}$ according to the following:

$$EC_{50} = (1 + K_{Comp}^{-1}) K_{Apt}^{-1} \tag{4}$$

From the in-line assay results, the ratio of the apparent $K_D$ of S4t (5 μM) to the $K_D$ of the aptamer alone (0.29 μM (Zimmermann et al, 2000)) was ~17. Solving for $K_{Comp}$ in equation (4) yields a value of 0.06. While this is below the fit value from the S1 data of 0.17, S1 has one less base pair than S4 contributed by the competing strand. Thus, the value from S4t is anticipated to be closer to 0.17 if the extra base pair is included. The fit value for $K_{Apt}$ (0.016 μM$^{-1}$) from the S1 data was lower than that for the aptamer alone (3.4 μM), which can be attributed to a theophylline concentration drop across the cellular membrane as observed in *E. coli* (Koch, 1956) and *S. cerevisiae* (J Liang, J Michener, C Smolke, unpublished data, 2007). Hence the model faithfully follows the underlying mechanism of ligand regulation of gene expression mediated by shRNA switches and can capture in vivo behavior by utilizing a minimal set of experiments.

References cited in this example are listed herein below.

Bartlett D W, Davis M E (2006) Insights into the kinetics of siRNA-mediated gene silencing from live-cell and live-animal bioluminescent imaging. Nucleic Acids Res 34: 322-333.

Gregory R I, Chendrimada T P, Cooch N, Shiekhattar R (2005) Human RISC couples microRNA biogenesis and posttranscriptional gene silencing. Cell 123: 631-640.

Grimm D, Streetz K L, Jopling C L, Storm T A, Pandey K, Davis C R, Marion P, Salazar F, Kay M A (2006) Fatality in mice due to oversaturation of cellular microRNA/short hairpin RNA pathways. Nature 441: 537-541.

Ketting R F, Fischer S E, Bernstein E, Sijen T, Hannon G J, Plasterk R H (2001) Dicer functions in RNA interference and in synthesis of small RNA involved in developmental timing in *C. elegans*. Genes Dev 15: 2654-2659.

Koch A L (1956) The metabolism of methylpurines by *Escherichia coli*. I. Tracer studies. J Biol Chem 219: 181-188.

Kok K H, Ng M H, Ching Y P, Jin D Y (2007) Human TRBP and PACT directly interact with each other and associate with dicer to facilitate the production of small interfering RNA. J Biol Chem 282: 17649-17657.

Lee Y, Hur I, Park S Y, Kim Y K, Suh M R, Kim V N (2006) The role of PACT in the RNA silencing pathway. EMBO J. 25: 522-532.

Malphettes L, Fussenegger M (2006) Impact of RNA interference on gene networks. Metab Eng 8: 672-683.

Matranga C, Tomari Y, Shin C, Bartel D P, Zamore P D (2005) Passenger-strand cleavage facilitates assembly of siRNA into Ago2-containing RNAi enzyme complexes. Cell 123: 607-620.

Raab R M, Stephanopoulos G (2004) Dynamics of gene silencing by RNA interference. Biotechnol Bioeng 88: 121-132.

Rand T A, Petersen S, Du F, Wang X (2005) Argonaute2 cleaves the anti-guide strand of siRNA during RISC activation. Cell 123: 621-629.

Westerhout E M, Berkhout B (2007) A systematic analysis of the effect of target RNA structure on RNA interference. Nucleic Acids Res.

Yi R, Doehle B P, Qin Y, Macara I G, Cullen B R (2005) Overexpression of exportin 5 enhances RNA interference mediated by short hairpin RNAs and microRNAs. RNA 11: 220-226.

Yi R, Qin Y, Macara I G, Cullen B R (2003) Exportin-5 mediates the nuclear export of pre-microRNAs and short hairpin RNAs. Genes Dev 17: 3011-3016.

Zimmermann G R, Wick C L, Shields T P, Jenison R D, Pardi A (2000) Molecular interactions and metal binding in the theophylline-binding core of an RNA aptamer. RNA 6: 659-667.

Example 8

Free Energy Calculations and Model Extension

The model derived in Example 7 identified different tuning trends that were observed in our experimental analysis, although this form of the model only predicts qualitative shifts in the transfer function based upon nucleotide changes to a parent shRNA switch. We sought to augment the model with predictive capabilities for the forward design of shRNA switch sequences that yield desired transfer functions. We initially focused on $K_{Comp}$, the partitioning coefficient between active and inactive conformations, since it solely captured the effect of multiple changes to the switching strand and has a thermodynamic basis. Under basic thermodynamic assumptions, $K_{Comp}$ is related to the free energy difference ($\Delta G$) between the active and inactive conformations according to $$\Delta G = E(\text{P}) - E(\text{I}) = -N_A k_B T \cdot \ln(K_{Comp}), \quad (1)$$

where $N_A$ is Avogadro's number, $k_B$ is the Boltzmann constant, and T is temperature (K). If $\Delta G$ can be calculated for a given shRNA switch sequence, then the corresponding value of $K_{Comp}$ can be calculated. When paired with the other experimentally-determined parameter values (Example 7), this value of $K_{Comp}$ can then be used in the model to predict the transfer function relating ligand concentration and relative gene expression levels. The initial challenge is calculating an experimentally valid $\Delta G$ from a given shRNA switch sequence.

Free Energy Calculation

To calculate $\Delta G$, we employed the RNA secondary structure prediction program RNAStructure 4.5 (Mathews et al, 2004) to output structural and energetic information for a given sequence. The program's dynamic folding algorithm utilizes empirical energy values measured in vitro (Mathews et al, *Proc Natl Acad Sci USA* 101: 7287-7292, 2004) to predict RNA conformations and their relative free energy. Since application of the program to in vivo folding has rarely been addressed (Mathews et al, 2004), we first asked if $\Delta G$ values calculated from the program ($\Delta G_{method}$) correlated with measured basal expression levels for each shRNA switch. Two commonly used methods were initially employed to calculate $\Delta G_{method}$ for S1-10 (switches with the same aptamer domain and shRNA stem): minimal free energy of the active and inactive conformation (MFE method) and partition function calculation to find the relative probability of either general conformation (PF method). $\Delta G_{method}$ values were then plotted with the associated basal expression levels measured in vivo (Table II) and compared to the expected trend from the model ($\Delta G_{model}$; FIG. 6B). A three-parameter equation with the same mathematical form as the model was then fit to each data set using a least-squares analysis to evaluate the correlation strength, since a strong correlation is necessary for accurate prediction of the transfer function. The mathematical form used to fit the data was:

$$f_{fit} = 1 - C_1 \left[ C_2 + \exp\left(-\frac{\Delta G_{method}}{k_B N_A T}\right) \right]^{-C_3}, \quad (2)$$

where C1, C2, and C3 are fit constants and $f_{fit}$ is the basal expression of the target gene for the fit curve.

MFE Method

The minimal free energy conformation—the most stable conformation—has been considered to be representative of the actual tertiary structure, and the free energy of this conformation is often considered to represent overall energetics of the RNA sequence. Under the MFE method, the free energy is recorded for the most stable active and inactive conformation. The difference in these free energy values is then reported as $\Delta G_{method}$. The resulting plot (FIG. 12) shows no significant correlation and an associated weak fit ($R^2=0.35$), suggesting that this method is insufficient for predicting transfer functions.

PF Method

Calculation of the partition function is a more advanced and considered to be a more accurate method for the approximation of RNA energetics. All possible secondary structure conformations and their energies are calculated in order to identify the most prevalent conformation, which often deviates from the minimal free energy conformation. Under the PF method, the program outputs the probability of a given base-pair based on the partition function calculation. To convert these probabilities into a value of $\Delta G$, we first found the smaller value of the base-pair probabilities near the top and bottom of the upper shRNA stem (starting at the stem bulge) in the active conformation and the stem formed by the switching strand and the shRNA stem in the inactive conformation (FIG. 11). Base-pairs were chosen such that the same nucleotide in the shRNA stem was part of the selected base-pair in both conformations. This ensures that a base-pair probability only applies to one of the two conformations. In other words the sum of the base-pair probabilities that include the same nucleotide for both conformations should always be less than one. Ideally, the sum should equal one, where all calculated sums for S1-10 were between 85% and 99% (data not shown). The value of $\Delta G_{method}$ can be calculated from the base-pair probabilities according to the following:

$$\Delta G_{method} = -k_B N_A T \cdot \ln\left(\frac{P_I}{P_A}\right), \tag{3}$$

where $P_A$ and $P_I$ are the base-pair probabilities representing the active or inactive conformations, respectively. $\Delta G_{method}$ values were calculated using the PF method and plotted in the same way as above (FIG. 12). The PF method provided a better fit ($R^2$=0.53) when compared to the MFE method that qualitatively matched the model trend, although the fit is not suitable for predictive purposes either.

Stems Method

While increasing the extent of base-pairing between the switching strand and shRNA stem always resulted in an increase in basal expression levels (FIG. 3B-G), the MFE and PF calculations output predicted an increase or decrease in free energy changes based on binding interactions outside of the major stems. We attributed the inaccuracy of the MFE and PF methods to the equal weight placed on these binding interactions. To remove these contributions to the energetic calculation, we devised a third method we term the stems method. This method only accounts for the energetic contributions from the major stems in the active and inactive conformations. The major stem for the active conformation spans from the shRNA stem bulge to the top of the shRNA stem, while the major stem for the inactive conformation includes base-pairs formed between the shRNA stem and the switching strand (FIG. 11). The lower portion of the shRNA stem is ignored since it is present in both conformations. As before, we calculated $\Delta G_{method}$ for S1-10 and plotted these values against the basal expression levels. The resulting plot (FIG. 6C) shows a strong correlation ($R_2$=0.94), a significant improvement over the other methods.

It is surprising yet insightful that the most accurate method only accounts for energetic contributions from regions that interact with the switching strand, which is precisely and solely where $K_{Comp}$ maps. An inequality does exist between the fit curve from the stems method and model predictions in terms of the abscissa values and curve slope, which suggests that sequences outside of the major stem contribute to folding energetics in vivo in a way that is improperly treated by the MFE or PF method.

Model Extension

Based on the strong correlation between $\Delta G_{method}$ calculated from shRNA switch sequence and in vivo basal expression levels, the fit curve from the stems method (but not the MFE or PF methods) can be incorporated into our model for the forward design of shRNA switches. This is accomplished by converting the value of $\Delta G_{method}$ calculated from the stems method into $K_{Comp}$ that can be used in the model to predict the transfer function. To perform this conversion, f from the model equation and $f_{fit}$ from the curve fit are set equal to each other. For successful conversion, the dynamic range (the range off) of the model and fit curves must match exactly. This can be done by ensuring that $$1 - e \cdot f_{shRNA} = f_{fit}(\Delta G_{method} \to \infty) \tag{4}$$

where e and $f_{shRNA}$ are model parameters. Once set equal to each other, $K_{Comp}$ can be found in terms of $\Delta G_{method}$:

$$K_{Comp} = \sqrt[h]{\frac{e \cdot f_{shRNA}}{C_1}\left[C_2 + \exp\left(-\frac{\Delta G_{method}}{k_B N_A T}\right)\right]^{C_3}} - 1. \tag{5}$$

Replacing $K_{Comp}$ in the model with equation (5) yields the extended model:

$$f_{model} = \tag{6}$$

$$1 - e \cdot f_{shRNA}\left[1 + \left[\frac{\sqrt[h]{\frac{e \cdot f_{shRNA}}{C_1}\left[C_2 + \exp\left(-\frac{\Delta G_{method}}{k_B N_A T}\right)\right]^{C_3}} - 1}{(1 + K_{Apt} \cdot L)}\right]\right]^{-h}.$$

Following experimental determination of the remaining model parameter values (Example 7), this equation can be used to predict relative expression levels of the target gene ($f_{model}$) as a function of ligand concentration (L) by calculating $\Delta G_{method}$ under the stems method using RNAStructure.

Example 9

Model-Guided Forward Design of shRNA Switches with Optimized Transfer Functions

Figure 6D:
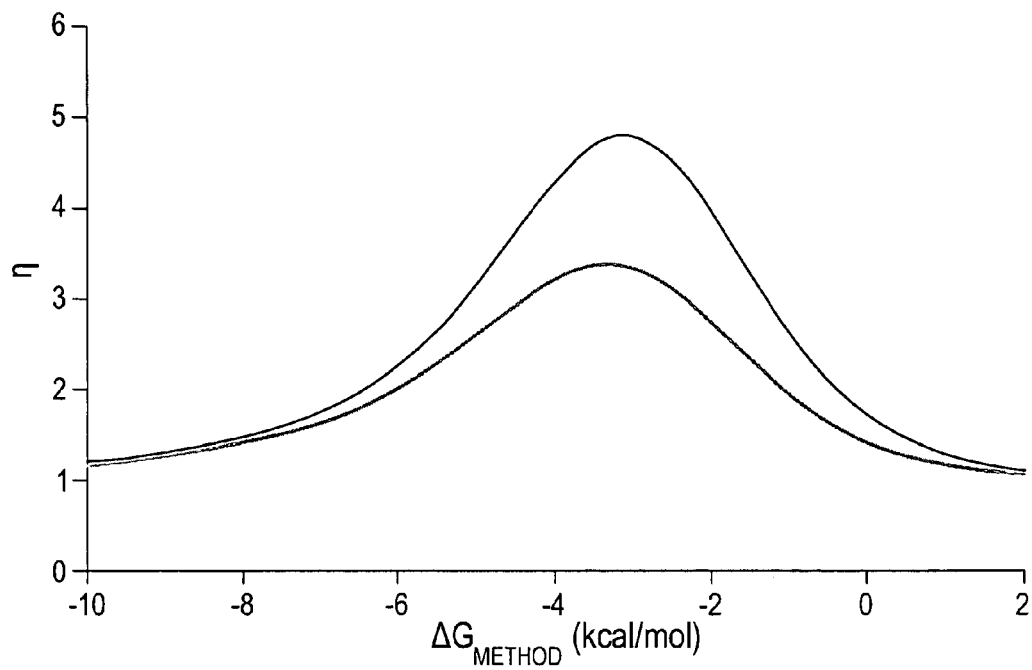
Figure 6E:
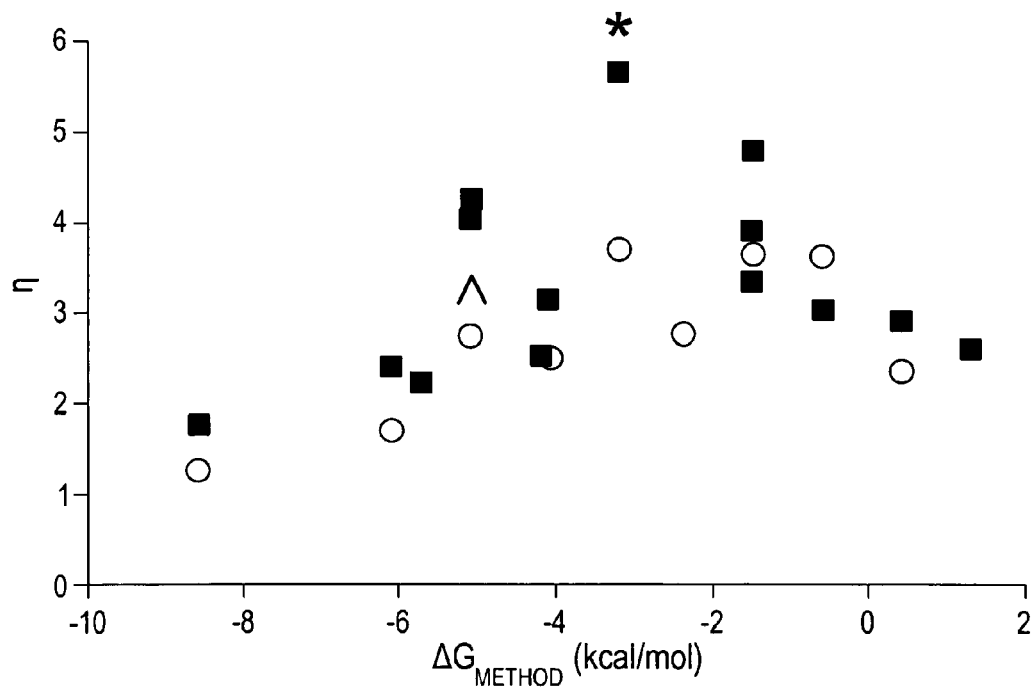
Figure 6F:
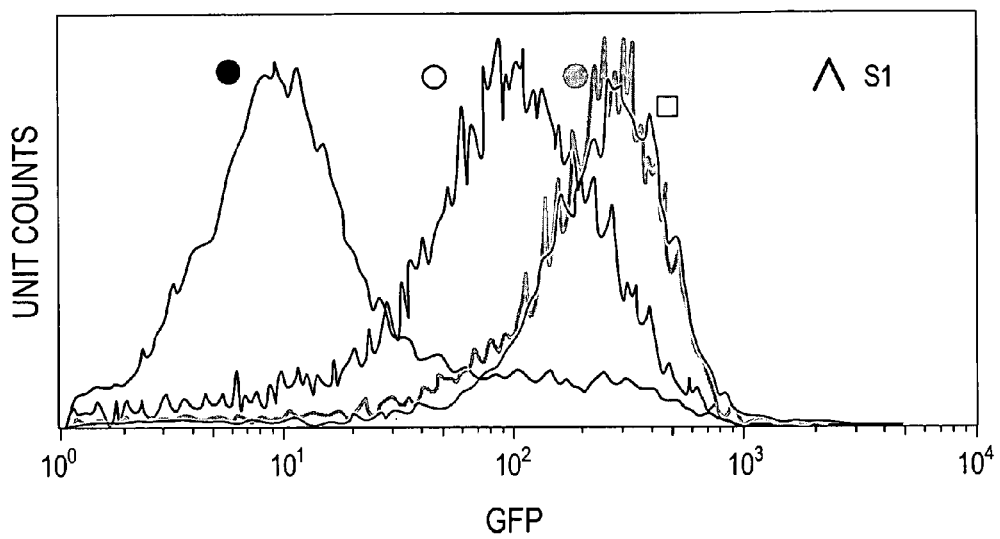
Figure 6G:
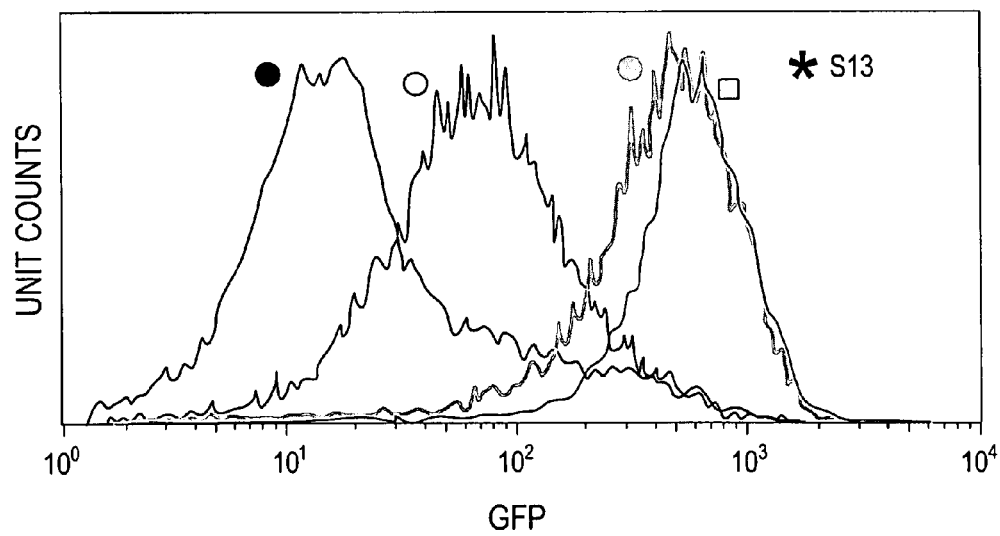

To apply the extended model to the forward design of shRNA switches with defined functional properties, Applicants sought to design a theophylline-regulated shRNA switch displaying a maximized dynamic range ($\eta$). Here, $\eta$ is defined as the ratio of GFP levels at high (3 mM) and low (1 μM) theophylline concentrations. Applicants used the extended model to calculate the range of $\Delta G$ values where $\eta$ is maximized. Model predictions suggest that $\eta$ is maximized for switches with $\Delta G_{method}$~−3 kcal/mol and that use of the smaller theophylline aptamer (higher e) yields a higher maximum (FIG. 6D). To evaluate the predicted landscape, Applicants designed new shRNA switches (S13-25) that include the smaller theophylline aptamer and display ranging $\Delta G$ values, generated component transfer functions, and calculated $\eta$. Plotting $\Delta G_{method}$ against the measured value of $\eta$ for all theophylline-regulated shRNA switches (S1-25; FIG. 6E) shows a maximum for switches containing the smaller theophylline aptamer that is higher than that for the switches containing the larger aptamer. Furthermore, both maxima existed at $\Delta G_{method}$~−3 kcal/mol as predicted by the extended model supplemented with the empirical parameter values, and the best switch (S13) was approximately equal to the theoretical maximum of $\eta$ according to model predictions ($\eta_{max,theor}$~5). Flow cytometry data illustrate the improvement in dynamic range (FIG. 13) for the best shRNA switch (S13; FIG. 6G) as compared to the original shRNA switch (S1; FIG. 6F).

To examine the generality of shRNA switch design and functionality, Applicants designed a set of shRNA switches targeting the endogenous La protein. Following selection of an shRNA sequence that yields moderate knockdown of La as ascertained by qRT-PCR, various switching strand sequences covering a range of $\Delta G$ values were combined with the smaller theophylline aptamer to yield six shRNA switches (L1-6). Each shRNA switch showed variable response to 1.5 mM theophylline that was not observed for the base shRNA (FIG. 14). As observed for the GFP-targeting shRNA switches, use of the stems method provided a suitable correlation between basal levels and $\Delta G_{method}$. Supplying the model with fit values for $C_{1-3}$ yielded a predicted dynamic range trend that closely matched the experimental data. Interestingly, when the values of $f_{shRNA}$ and e calculated from the base shRNA and an shRNA switch preferentially adopting the active conformation (L6) were combined with the remaining parameter values from the GFP experiments, the resulting trend predicted the same maximal dynamic range with a shifted value of $\Delta G_{method}$ that maximizes dynamic range. This suggests that sequence-specific factors affect calculations with the stems method such that empirical values are specific to individual sequences and experimental conditions. However the stems method produced a strong correlation such that the model may be implemented in future designs by generating a small set of shRNA switches covering $\Delta G_{method}$ values of approximately −5 to 0 kcal/mol and measuring basal expression levels. Thus, shRNA switches can be constructed to target different genes and the model can be used as a tool for forward design.

A comparison between the framework described here and a recently described ligand-controlled shRNA system (An et al, 2006) highlights important design strategies to engineer domain swapping and tuning of the transfer function into synthetic riboswitch systems. In the previous design, ligand control of RNAi was achieved through direct coupling of the theophylline aptamer and an shRNA stem. This design inherently limits aptamer swapping since the aptamer must perform ligand binding coordinated with modulation of Dicer processing, and prevents tuning of the transfer function since sequence changes that modulate Dicer processing cannot be implemented without a complete loss of ligand responsiveness. In contrast, the framework described herein is based on the coupling of three distinct domains that carry out separate functions necessary to convert ligand binding into modulation of RNAi activity. This system requires that the aptamer performs one function—ligand binding—and the modulation of RNAi processing is performed by a separate domain, the switching strand. The switching strand permits fine tuning of the transfer function and enables modular coupling of the aptamer and shRNA stem domains, as confirmed by independently replacing each domain and demonstrating preservation of functionality.

Applicants developed a model to enhance the understanding of shRNA switch activity and identified five tuning strategies reflected in three model parameters, $K_{Comp}$, $K_{Apt}$, and e that map specifically to sequence changes in the switching strand or aptamer domains. This model also established important shRNA switch design guidelines. The first is that basal expression levels are determined by a collection of factors: shRNA potency ($f_{shRNA}$), shRNA switch processability (e), and prevalence of the active conformation ($K_{Comp}$). To achieve a desired basal expression level, all factors must be considered in the switch design. Another guideline originates from the observation that larger aptamers coincided with increased basal expression levels, potentially due to sterically hindering processing by the RNAi machinery. The specific contribution of secondary or tertiary structure to the inhibitory effect is unclear, although further understanding of how the RNAi machinery specifically interacts with the shRNA through crystallographic or mutational studies may shed light on this dependence. Our results suggest that shRNA switch sequence length has an upper limit before compromising activity, where future engineering efforts may focus on alleviating or entirely removing this limitation. Furthermore, if achieving low basal expression levels is critical and a set of aptamers against the same ligand are available, use of smaller aptamers may be preferred even at a cost to aptamer affinity. Such a guideline may even direct library design for the selection of new aptamers by placing an upper limit on the length of the randomized sequence.

Applicants also incorporated RNA folding algorithms into our model for in silico prediction of shRNA switch behavior in vivo. The resulting model yielded a framework for the forward design of shRNA switches with specified functional properties. This was achieved by linking RNA secondary structure prediction algorithms, which convert sequence information into energetic values, to our model, which converts energetic values into switch behavior to provide an empirical sequence-function relationship. The specific method used to calculate the free energy difference ($\Delta G_{method}$) between active and inactive conformations deviated from commonly used methods (MFE and PF calculations) based on observations from the experimental tuning trends. Our alternative method may provide a better correlation with experimental results by focusing the prediction of $K_{Comp}$ to the region of the switch in which the switching strand binding events are occurring, ignoring energetic contributions by other regions of the switch molecule that may not be relevant to the in vivo conformational switching process. Our analysis moves towards direct sequence-to-function relationships and suggests that commonly used methods for predicting RNA structure and behavior should be carefully evaluated when applied to in vivo environments. RNA folding in vivo is a complex process, and algorithms that account for folding kinetics (Danilova et al, 2006) and ulterior structural formation (Parisien and Major, 2008), such as pseudoknots or non-canonical base-pairing interactions, may increase the accuracy of the model as well as provide insight into sequences that deviate from model predictions (FIG. 6E; and FIG. 10). Other algorithms may also be used. Such algorithms may provide the ability to rapidly scan suboptimal structures, to calculate the energetics of multiple RNA strands, and to perform a partition function calculation, etc. While the PF method did not produce a strong correlation using existing algorithms, it may be useful for the subject method using an algorithm designed to account for non-canonical base-pairing interactions.

Based on the demonstrated modularity and tunability of our platform, shRNA switches can be implemented towards various applications. As one potential application, shRNA switches could be applied to disease therapy by sensing intracellular disease markers and inducing apoptosis or cell cycle arrest only in the affected cells. When a context-dependent concentration threshold divides diseased and normal cells, tunability is essential to reduce the likelihood of false positives or negatives. As long as the sensitivity of the threshold does not exceed the dynamic range of the shRNA switch, the response curve can be finely tuned to ensure that basal and ligand-saturating levels coincide with survival or the induction of apoptosis. In addition, shRNA switches could be integrated into synthetic genetic circuits to generate advanced control schemes in biological systems. Such systems often exhibit complex dependencies on the dynamics of component interactions, and tuning of component behavior is often necessary to achieve optimal system performance. Through the fine tuning strategies and model-guided forward design tools described here, shRNA switches may be used to address challenges faced in biological network design and serve as complex regulatory components in synthetic biology.

The following section provides exemplary materials and methods used in Example 1-9, which are for illustrative purpose only, and are not necessarily limiting in any respect.

Materials and Methods

Plasmid Construction.

All shRNAs were cloned into pSilencer 2.1-U6 puro (Ambion). The original shRNA present in pSilencer was used as a scrambled shRNA control. The pSilencer backbone was modified to co-express DsRed-Express in 293T cells by cloning the SV40 origin of replication, CMV IE promoter, and DsRed-Express into the NsiI/MfeI restriction sites. The original XhoI site present in the backbone was also removed by XhoI cleavage, extension with the large Klenow fragment (New England Biolabs), and ligation. To clone the shRNA switches, the original shRNA followed by a 6-nucleotide (nt) string of T's was cloned into BamHI/HindIII directly downstream of the U6 promoter. The original shRNA was converted into an shRNA switch by cloning the remaining sequence into XhoI/XbaI contained within the shRNA loop region. All cloning steps involved annealing of 5'-phosphorylated synthetic oligonucleotides (Integrated DNA Technologies) and ligation into the backbone vector. All restriction enzymes and T4 DNA ligase were purchased from NEB. All constructs were sequence-verified (Laragen, Inc.), where sequences are provided in Table I.

TABLE I

Table I (SEQ ID NOS 5-21, respectively, in order of appearance)

| Name | Aptamer | Sequence | Cloning sites (5'/3') | Database # |
|---|---|---|---|---|
| neg | N/A | GGATCCACTACCGTTGTTATAGGTGTTCAAGAGACACCTATAACAACGGTAGTTTTTTGGAAAAGCTT | BamHI/HindIII | pCS628 |
| sh |  | GGATCCGGTGCAGATGAACTTCAGGGTCAGCCTCGAGTCTAGAGCTGACCCTGAATCATCTGCACCTTTTTTGGAAGCTT |  | pCS741 |
| shL |  | GGATCCGGCTTCCCAACGATGATGCAACTCCTCGAGTCTAGAGGAGTTGCATCAGTTGGGAAGCCTTTTTGGAAGCTT |  | pCS1457 |
| S1 | theophylline | CTCGAGATACCAGCATCGACTCTTCGATGCCCTTGGCAGCTCGGGCTGACCCTGACTAGA | XhoI/XbaI | pCS630 |
| S1' |  | CTCGAGGACCCAGCATCGACTCTTCGATGCAAATGGCAGCTCGGGCTGACCCTGACTAGA |  | pCS847 |
| S2 |  | CTCGAGATACCAGCATCGACTCTTCGATGCCCTTGGCAGCTCGGGCTGACCCTGAAGCTAGA |  | pCS633 |
| S3 |  | CTCGAGATACCAGCATCGACTCTTCGATGCCCTTGGCAGCTCGGGCTGACCCTGAACTAGA |  | pCS631 |
| S4 |  | CTCGAGATACCAGCATCGACTCTTCGATGCCCTTGGCAGCTCGGGCTGACCCTGCTAGA |  | pCS628 |
| S5 |  | CTCGAGATACCAGCATCGACTCTTCGATGCCCTTGGCAGCTCGGGCTGACCCTCTAGA |  | pCS632 |
| S6 |  | CTCGACGATACCAGCATCGACTCTTCGATGCCCTTGGCAGCGTCGGGCTGACCCTGCTAGA |  | pCS848 |
| S7 |  | CTCGATACCAGCATCGACTCTTCGATGCCCTTGGCAGCGAGCTGACCCTGCTAGA |  | pCS807 |
| S8 |  | CTCGAGATACCAGCATCGACTCTTCGATGCCCTTGGCAGCTCGAGCTGACCCTGCTAGA |  | pCS629 |
| S9 |  | CTCGAGATACCAGCATCGACTCTTCGATGCCCTTGGCAGCTCGAGCTGATCCTGCTAGA |  | pCS1005 |
| S10 |  | CTCGATACCAGCATCGACTCTTCGATGCCCTTGGCAGCGAGCTGACCCTGACTAGA |  | pCS808 |
| S11 |  | CTCGAGATACCAGCCGAAAGGCCCTTGGCAGCTCGGGCTGACCCTGACTAGA |  | pCS634 |
| S12 |  | CTCGAGATACCACCGAAAGGCCCTTGGCAGCTCGGGCTGACCCTGACTAGA |  | pCS635 |
| S13 |  | CTCGAGATACCAGCCGAAAGGCCCTTGGCAGCTCGGGCTGACCCTGCTAGA |  | pCS911 |

Table I (continued) (SEQ ID NOS 22-40, respectively, in order of appearance)

| Name | Aptamer | Sequence | Cloning-sites (5'/3') | Database # |
|---|---|---|---|---|
| S14 |  | CTCGATACCAGCCGAAAGGCCCTTGGCAGCGAGCTGACCCTGCTAGA |  | pCS908 |
| S15 |  | CTCGATACCAGCCGAAAGGCCCTTGGCAGCGGGCTGACCCTGCTAGA |  | pCS909 |
| S16 |  | CTCGATACCAGCCGAAAGGCCCTTGGCAGCGAGCTGACCCTGACTAGA |  | pCS910 |
| S17 |  | CTCGAGATACCAGCCGAAAGGCCCTTGGCAGCTCGAGCTGACCCTGCTAGA |  | pCS941 |
| S18 |  | CTCGAGATACCAGCCGAAAGGCCCTTGGCAGCTCGAGCTGACCCTACTAGA |  | pCS942 |
| S19 |  | CTCGAGATACCAGCCGAAAGGCCCTTGGCAGCTCGGGCTGACCCTGAACTAGA |  | pCS1001 |
| S20 |  | CTCGAGATACCAGCCGAAAGGCCCTTGGCAGCTCGGGCTGACCCTGAAGCTAGA |  | pCS1002 |
| S21 |  | CTCGAGATACCAGCCGAAAGGCCCTTGGCAGCTCGGGCTGACCCTGGCTAGA |  | pCS1003 |

TABLE I-continued

| | | | |
|---|---|---|---|
| S22 | | CTCGATACCAGCCGAAAGGCCCTTGGCAGCGAGCT GACCCTGAACTAGA | pCS1004 |
| S23 | | CTCGAGATACCAGCCGAAAGGCCCTTGGCAGCTCG AGCTGATCCTGCTAGA | pCS1061 |
| S24 | | CTCGAGATACCAGCCGAAAGGCCCTTGGCAGCTCG GGCTGATCCTGCTAGA | pCS1062 |
| S25 | | CTCGAGATACCAGCCGAAAGGCCCTTGGCAGCTCG GGCTGATCCTGACTAGA | pCS1063 |
| X1 | xanthine/guanine | CTCGAGTGTATTACCCAGCGAGGTCGACTCGAGCT GACCCTGACTAGA | XhoI/XbaI pCS870 |
| X1' | | CTCGAGTTTCAAACCCAGCGAGGTACACTCGAGCT GACCCTGACTAGA | pCS913 |
| X2 | | CTCGAGTGTATTACCCAGCGAGGTCGACTCGAGCT GACCCTGAACTAGA | pCS972 |
| X3 | | CTCGAGTGTATTACCCAGCGAGGTCGACTCGAGCT GACCCTGCTAGA | pCS869 |
| T1 | tetracyline | CTCGAAAACATACCAGAGAAATCTGGAGAGGTGAA GAATACGACCACCTCGAGCTGACCCTGACTAGA | XhoI/XbaI pCS893 |
| T2 | | CTCGAAAACATACCAGAGAAATCTGGAGAGGTGAA GAATACGACCACCTCGAGCTGACCCTGAACTAGA | pCS894 |
| T3 | | CTCGAAAACATACCAGAGAAATCTGGAGAGGTGAA GAATACGACCACCTCGAGCTGACCCTGCTAGA | pCS895 |

Table I (continued)(SEQ ID NOS 22-40, respectively, in order of appearance)

| Name | Aptamer | Sequence | Cloning-sites (5'/3') | Database # |
|---|---|---|---|---|
| L1 | theophylline | CTCGAGATACCAGCCGAAAGGCCCTTGGCAGCTCG AGGAGTTGCATCCTAGA | XhoI/XbaI | pCS1458 |
| L2 | | CTCGAGATACCAGCCGAAAGGCCCTTGGCAGCTCG AGGAGTTGCATTCTAGA | | pCS1459 |
| L3 | | CTCGAGATACCAGCCGAAAGGCCCTTGGCAGCTTG AGGAGTTGCATCCTAGA | | pCS1460 |
| L4 | | CTCGAGATACCAGCCGAAAGGCCCTTGGCAGCTTG AGGAGTTGCATACTAGA | | pCS1462 |
| L5 | | CTCGAGATACCAGCCGAAAGGCCCTTGGCAGCTCG AGGAGTTGCACTAGA | | pCS1463 |
| L6 | | CTCGAGATACCAGCCGAAAGGCCCTTGGCAGCTTG AGGAGTTGCACTAGA | | pCS1464 |

TABLE II

| Name | Aptamer | Basal expression levels (%) | η | ΔG (method) MFE | ΔG (method) PF | ΔG (method) Stems |
|---|---|---|---|---|---|---|
| neg | N/A | 90.7 | 1.07 | | N/A | |
| sh | | 4.6 | 1.19 | | N/A | |
| S1 | theophylline | 33.8 | 2.71 | −0.1 | 0.6 | −5.1 |
| S1' | | 37.0 | 1.39 | −0.3 | 0.8 | −5.1 |
| S2 | | 76.7 | 1.25 | 0.0 | −0.2 | −8.6 |
| S3 | | 52.8 | 1.68 | −0.6 | −0.1 | −6.1 |
| S4 | | 23.8 | 3.65 | 3.2 | 3.4 | −3.2 |
| S5 | | 21.1 | 3.58 | 6.2 | 6.2 | −0.6 |
| S6 | | 42.5 | 2.20 | 2.1 | 2.7 | −5.7 |
| S7 | | 14.5 | 2.32 | 2.5 | 3.2 | 0.4 |
| S8 | | 37.3 | 2.47 | 0.3 | 1.2 | −4.1 |
| S9 | | 12.1 | 4.75 | 2.9 | 3.2 | −1.5 |
| S10 | | 29.4 | 3.60 | −0.9 | −0.1 | −1.5 |
| S11 | | 20.0 | 4.20 | 0.6 | 0.9 | −5.1 |
| S12 | | 13.4 | 4.06 | −0.1 | 0.8 | −5.1 |
| S13 | | 16.7 | 5.61 | 4.0 | 3.8 | −3.2 |
| S14 | | 14.3 | 2.86 | 2.6 | 3.3 | 0.4 |
| S15 | | 11.2 | 2.56 | 9.9 | 9.1 | 1.3 |
| S16 | | 21.7 | 3.85 | 0.1 | 0.1 | −1.5 |
| S17 | | 17.5 | 3.12 | 2.5 | 2.0 | −4.1 |
| S18 | | 19.5 | 3.89 | 5.7 | 4.5 | −1.5 |
| S19 | | 38.3 | 2.38 | −0.6 | 0.0 | −6.1 |
| S20 | | 49.8 | 1.75 | 0.0 | −0.2 | −8.6 |
| S21 | | 10.8 | 2.52 | 4.6 | 4.6 | −4.2 |
| S22 | | 35.0 | 2.73 | −0.9 | −0.9 | −2.4 |
| S23 | | 16.6 | 3.30 | 5.1 | 4.4 | −1.5 |
| S24 | | 10.8 | 3.00 | 6.6 | 6.1 | −0.6 |
| S25 | | 11.8 | 2.63 | 3.2 | 3.3 | −2.5 |

Preparation of RNAs.

S4t was transcribed in vitro from an annealed template containing the T7 promoter (5'-TTCTAATACGACTCAC-TATAGGG-3' (SEQ ID NO: 47), where G is the first transcribed nucleotide) using the Ampliscribe T7 transcription kit (Epicentre) according to the manufacturer's instructions. Following transcription and DNase treatment, unincorporated NTPs were removed using a NucAway clean-up column (Ambion). The 5' phosphates were subsequently removed using Antarctic phosphatase (NEB). Dephosphorylated RNA was then gel-purified on a 6% denaturing polyacrylamide gel and quantified using an ND-1OOO spectrophotometer (NanoDrop). RNAs were 5' radiolabeled using T4 PNK (NEB) and [γ-$^{32}$P]-ATP, purified using a NucAway clean-up column, and gel-extracted on a 6% denaturing polyacrylamide gel.

In-Line Probing.

In-line probing was conducted as described previously (Soukup et al, 1999). After heating at 70° C. for 2 min followed by slow cooling to room temperature, 5' radiolabeled RNAs (0.2 pmol) were incubated for 40 hours at 25° C. in varying amounts of theophylline with 50 mM Tris-HCl pH 8.5, 20 mM MgCl$_2$. Reactions were terminated by adding an equal volume of loading buffer (10 M urea, 1.5 mM EDTA). The alkaline hydrolysis ladder was generated by incubating RNA in 50 mM NaHCO$_3$/Na$_2$Co$_3$ pH 9.2, 1 mM EDTA for 6 min at 95° C. The G-specific cleavage ladder was generated by incubating RNA in 1 U RNase T1 (Ambion) with 20 mM sodium citrate pH 5.0, 1 mM EDTA, 7 M urea, and 3 μg yeast RNA for 25 min at 25° C. RNAs were resolved on an 8% denaturing polyacrylamide gel, dried for 90 min at 70° C., then visualized on an FX phosphorimager (BioRAD). Band quantification was performed using the Quantity One software package (BioRAD). To account for well loading variability, quantified band intensities were normalized to an adjacent band of similar intensity showing negligible theophylline dependence.

Cell Culture and Transfection.

All cells were maintained at 37° C. in a 5% CO$_2$—humidified incubator. HEK293T, HEK293, HeLa, and HEK293T tTA-d2EGFP cells were maintained in minimal essential medium (MEM) alpha media (Invitrogen) supplemented with 10% fetal bovine serum (FBS) (Invitrogen), whereas MDA-MB-231 cells were maintained in RMPI 1640 with glutamine (Invitrogen) supplemented with 10% FBS. Cells were transfected one day after seeding using Fugene 6 (Roche) according to the manufacturer's instructions, followed by the immediate addition of ligand. HEK293T tTA-d2EGFP were transfected with shRNA vector (250 ng), whereas cells lacking endogenous GFP were cotransfected with shRNA vector (250 ng) and the pcDNA3.1(+) (Invitrogen) harboring the d2EGFP gene (25 ng) (Clontech). One day post-transfection the media and ligand were replaced. Transfected cells were collected three days post-transfection for flow cytometry analysis.

Cell Fluorescence Analysis.

Three days post-transfection, cells were trypsinized and subjected to flow cytometry analysis using the Cell Lab Quanta SC MPL (Beckman Coulter). Cells were first gated twice for (1) viability as assessed by electronic volume (EV) versus side scatter (SS) and (2) green fluorescence above autofluorescence to remove a nonfluorescent subpopulation. Cells were then gated for either low or high DsRed-Express fluorescence, representing untransfected or transfected cells, respectively. To minimize well-to-well variability, the median green fluorescence value of transfected cells were divided by that of untransfected cells in the same well and reported as GFP (%). For cells cotransfected with shRNA and GFP plasmids, GFP (%) is the relative GFP levels when normalized to mean red fluorescence followed by normalization to cells transfected with the scrambled shRNA. See FIG. 15 for representative plots and the corresponding gates for transfected and untransfected cells.

Estimation of the Lower Limit of Basal Expression Levels.

Our model asserts that the active conformation sets the greatest knockdown that can be achieved by an shRNA switch containing a given aptamer sequence in a specified experimental setup. This level was evaluated for shRNA switches that preferentially adopt the active conformation through switching strand modifications and contain the larger theophylline (average of S5, S7, S9, and S10), smaller theophylline (average of S7, S14, S15) tetracycline (T3), and xanthine (X3) aptamers. See Table I for the specified shRNA switch sequences.

Modeling and RNA Energetic Calculations.

Calculation of RNA free energy and partition functions were performed using RNAStructure (Mathews et al, 2004). $K_{Comp}$ and the energy difference between inactive and active conformations are related by the following expression:

$$\Delta G_{model} = E(\text{active}) - E(\text{inactive}) = -N_A k_B T \cdot \ln(K_{Comp}), \quad (3)$$

where $N_A$ is Avogadro's number, $k_B$ is the Boltzmann constant, and T is temperature (K). A full description of the model derivation, methods for calculating folding energetics, and prediction of the transfer function for a given shRNA switch sequence are provided below. Equation fits to measure the correlation strength between $\Delta G_{method}$ and basal expression levels were performed by least-squares analysis using the following expression that has the same mathematical form as equation (1):

$$f_{fit} = 1 - C_1 \left[ C_2 + \exp\left(-\frac{\Delta G_{method}}{k_B N_A T}\right) \right]^{-C_3}, \quad (4)$$

where $C_{1-3}$ are the fit constants. Table II contains energetic values calculated under each method along with experimentally determined expression levels.

REFERENCES

Abbas-Terki T, Blanco-Bose W, Deglon N, Pralong W, Aebischer P (2002) Lentiviral-mediated RNA interference. *Hum Gene Ther* 13: 2197-2201.

An C I, Trinh V B, Yokobayashi Y (2006) Artificial control of gene expression in mammalian cells by modulating RNA interference through aptamer-small molecule interaction. *RNA* 12: 710-716.

Bartlett D W, Davis M E (2006) Insights into the kinetics of siRNA-mediated gene silencing from live-cell and live-animal bioluminescent imaging. *Nucleic Acids Res* 34: 322-333.

Bayer T S, Smolke C D (2005) Programmable ligand-controlled riboregulators of eukaryotic gene expression. *Nat Biotechnol* 23: 337-343.

Berens C, Thain A, Schroeder R (2001) A tetracycline-binding RNA aptamer. *Bioorg Med Chem* 9: 2549-2556.

Buskirk A R, Landrigan A, Liu D R (2004) Engineering a ligand-dependent RNA transcriptional activator. *Chem Biol* 11: 1157-1163.

Croft L J, Lercher M J, Gagen M J, Mattick J S (2003) Is prokaryotic complexity limited by accelerated growth in regulatory overhead? *Genome Biology* 5: P2.

Danilova L V, Pervouchine D D, Favorov A V, Mironov A A (2006) RNAKinetics: a web server that models secondary structure kinetics of an elongating RNA. *J Bioinform Comput Biol* 4: 589-596.

Deans T L, Cantor C R, Collins J J (2007) A Tunable Genetic Switch Based on RNAi and Repressor Proteins for Regulating Gene Expression in Mammalian Cells. *Cell* 130: 363-372.

Desai S K, Gallivan J P (2004) Genetic screens and selections for small molecules based on a synthetic riboswitch that activates protein translation. *J Am Chem Soc* 126: 13247-13254.

Dueber J E, Mirsky E A, Lim W A (2007) Engineering synthetic signaling proteins with ultrasensitive input/output control. *Nat Biotechnol* 25: 660-662.

Elowitz M B, Leibler S (2000) A synthetic oscillatory network of transcriptional regulators. *Nature* 403: 335-338.

Flotte T R (2000) Size does matter: overcoming the adeno-associated virus packaging limit. *Respir Res* 1: 16-18.

Gardner T S, Cantor C R, Collins J J (2000) Construction of a genetic toggle switch in *Escherichia coli. Nature* 403: 339-342.

Grate D, Wilson C (2001) Inducible regulation of the *S. cerevisiae* cell cycle mediated by an RNA aptamer-ligand complex. *Bioorg Med Chem* 9: 2565-2570.

Grieger J C, Samulski R J (2005) Packaging capacity of adeno-associated virus serotypes: impact of larger genomes on infectivity and postentry steps. *J Virol* 79: 9933-9944.

Griffiths-Jones S (2004) The microRNA Registry. *Nucleic Acids Res* 32: D109-111.

Griffiths-Jones S, Grocock R J, van Dongen S, Bateman A, Enright A J (2006) miRBase: microRNA sequences, targets and gene nomenclature. *Nucleic Acids Res* 34: D140-144.

Grundy F J, Henkin T M (2006) From ribosome to riboswitch: control of gene expression in bacteria by RNA structural rearrangements. *Crit. Rev Biochem Mol Biol* 41: 329-338.

Hall B, Hesselberth J R, Ellington A D (2007) Computational selection of nucleic acid biosensors via a slip structure model. *Biosens Bioelectron* 22: 1939-1947.

Hooshangi S, Thiberge S, Weiss R (2005) Ultrasensitivity and noise propagation in a synthetic transcriptional cascade. *Proc Natl Acad Sci USA* 102: 3581-3586.

Huang C Y, Ferrell J E, Jr. (1996) Ultrasensitivity in the mitogen-activated protein kinase cascade. *Proc Natl Acad Sci USA* 93: 10078-10083.

Hutvagner G, Simard M J, Mello C C, Zamore P D (2004) Sequence-specific inhibition of small RNA function. *PLoS Biol* 2: E98.

Isaacs F J, Dwyer D J, Collins J J (2006) RNA synthetic biology. *Nat Biotechnol* 24: 545-554.

Isaacs F J, Dwyer D J, Ding C, Pervouchine D D, Cantor C R, Collins J J (2004) Engineered riboregulators enable post-transcriptional control of gene expression. *Nat Biotechnol* 22: 841-847.

Jenison R D, Gill S C, Pardi A, Polisky B (1994) High-resolution molecular discrimination by RNA. *Science* 263: 1425-1429.

Kiga D, Futamura Y, Sakamoto K, Yokoyama S (1998) An RNA aptamer to the xanthine/guanine base with a distinctive mode of purine recognition. *Nucleic Acids Res* 26: 1755-1760.

Koch A L (1956) The metabolism of methylpurines by *Escherichia coli*. I. Tracer studies. *J Biol Chem* 219: 181-188.

Lee J F, Hesselberth J R, Meyers L A, Ellington A D (2004) Aptamer database. *Nucleic Acids Res* 32: D95-100.

Lynch S A, Desai S K, Sajja H K, Gallivan J P (2007) A high-throughput screen for synthetic riboswitches reveals mechanistic insights into their function. *Chem Biol* 14: 173-184.

Macrae I J, Zhou K, Li F, Repic A, Brooks A N, Cande W Z, Adams P D, Doudna J A (2006) Structural basis for double-stranded RNA processing by Dicer. *Science* 311: 195-198.

Malphettes L, Fussenegger M (2006) Impact of RNA interference on gene networks. *Metab Eng* 8: 672-683.

Mathews D H, Disney M D, Childs J L, Schroeder S J, Zuker M, Turner D H (2004) Incorporating chemical modification constraints into a dynamic programming algorithm for prediction of RNA secondary structure. *Proc Natl Acad Sci USA* 101: 7287-7292.

Meister G, Landthaler M, Dorsett Y, Tuschl T (2004) Sequence-specific inhibition of microRNA- and siRNA-induced RNA silencing. *RNA* 10: 544-550.

Ogawa A, Maeda M (2008) An artificial aptazyme-based riboswitch and its cascading system in *E. coli. Chembiochem* 9: 206-209.

Parisien M, Major F (2008) The MC-Fold and MC-Sym pipeline infers RNA structure from sequence data. *Nature* 452: 51-55.

Raab R M, Stephanopoulos G (2004) Dynamics of gene silencing by RNA interference. *Biotechnol Bioeng* 88: 121-132.

Rinaudo K, Bleris L, Maddamsetti R, Subramanian S, Weiss R, Benenson Y (2007) A universal RNAi-based logic evaluator that operates in mammalian cells. *Nat. Biotechnol.*

Seelig G, Soloveichik D, Zhang D Y, Winfree E (2006) Enzyme-free nucleic acid logic circuits. *Science* 314: 1585-1588.

Shalgi R, Lieber D, Oren M, Pilpel Y (2007) Global and Local Architecture of the Mammalian microRNA-Transcription Factor Regulatory Network. *PLoS Comput Biol* 3: e 131.

Soukup G A, Breaker R R (1999) Relationship between internucleotide linkage geometry and the stability of RNA. *RNA* 5: 1308-1325.

Stojanovic M N, Stefanovic D (2003) A deoxyribozyme-based molecular automaton. *Nat Biotechnol* 21: 1069-1074.

Sudarsan N, Barrick J E, Breaker R R (2003) Metabolite-binding RNA domains are present in the genes of eukaryotes. *RNA* 9: 644-647.

Suel G M, Kulkarni R P, Dworkin J, Garcia-Ojalvo J, Elowitz M B (2007) Tunability and noise dependence in differentiation dynamics. *Science* 315: 1716-1719.

Suess B, Hanson S, Berens C, Fink B, Schroeder R, Hillen W (2003) Conditional gene expression by controlling translation with tetracycline-binding aptamers. *Nucleic Acids Res* 31: 1853-1858.

Suess B, Weigand J E (2008) Engineered riboswitches— Overview, Problems and Trends. *RNA Biol* 5.

Thompson K M, Syrett H A, Knudsen S M, Ellington A D (2002) Group I aptazymes as genetic regulatory switches. *BMC Biotechnol* 2: 21.

Weigand J E, Suess B (2007) Tetracycline aptamer-controlled regulation of pre-mRNA splicing in yeast. *Nucleic Acids Res* 35: 4179-4185.

Wieland M, Hartig J S (2008) Improved aptazyme design and in vivo screening enable riboswitching in bacteria. *Angew Chem Int Ed Engl* 47: 2604-2607.

Win M N, Smolke C D (2007) From the Cover: A modular and extensible RNA-based gene-regulatory platform for engineering cellular function. *Proc Natl Acad Sci USA* 104: 14283-14288.

Yokobayashi Y, Weiss R, Arnold F H (2002) Directed evolution of a genetic circuit. *Proc Natl Acad Sci USA* 99: 16587-16591.

Zeng Y, Cullen B R (2004) Structural requirements for pre-microRNA binding and nuclear export by Exportin 5. *Nucleic Acids Res* 32: 4776-4785.

Zimmermann G R, Wick C L, Shields T P, Jenison R D, Pardi A (2000) Molecular interactions and metal binding in the theophylline-binding core of an RNA aptamer. *RNA* 6: 659-667.

All reference cited herein are incorporated by reference.

We claim:

1. A method for rendering expression of a target gene in a cell dependent on the presence or absence of a molecule, comprising introducing into the cell a polynucleotide comprising:
   (1) a modular actuator domain comprising a substrate for RNase III, wherein said substrate, when processed by RNase III, produces an siRNA or miRNA that targets a transcript of said target gene,
   (2) a modular sensor domain that detects concentration or status change of the molecule, wherein the modular sensor domain comprises an aptamer,
   (3) an information transmission domain (ITD) between the modular actuator domain and the modular sensor domain, said information transmission domain comprising:
      (a) a general transmission region,
      (b) a switching strand, and,
      (c) a competing strand,
         wherein the switching strand and the competing strand are in a continuous sequence and compete to bind to the general transmission region through hybridization interactions,
   (i) wherein detection of the concentration or status change by the modular sensor domain, through binding of said molecule to said modular sensor domain, favors a conformation change in the modular actuator domain;
   (ii) wherein said conformation change is mediated by a strand-displacement mechanism in the ITD to favor the binding of the general transmission region to one of said switching strand and said competing strand; and wherein said hybridization interactions are sufficient to allow said conformation change to occur by the strand-displacement mechanism; and,
   (iii) wherein said conformation change modulates the ability of said substrate to be processed by RNase III to produce the siRNA or miRNA for targeting said transcript, at a rate dependent upon the presence or absence of said molecule.

2. The method of claim 1, wherein the target gene is a reporter gene, the method further comprising:
   (A) measuring the amount of expression of said reporter gene; and
   (B) correlating the amount of expression of said reporter gene with the amount of the molecule, thereby determining the amount of the molecule in the cell.

3. The method of claim 1, wherein the polynucleotide is an RNA.

4. The method of claim 1, wherein said substrate is an siRNA precursor, an miRNA precursor, or an shRNA precursor.

5. The method of claim 1, wherein said ability of said substrate to be processed by RNase III to produce said siRNA or miRNA comprises: an ability to be incorporated into a RISC complex to serve as an siRNA or miRNA guide sequence, or an ability to be an RNase III substrate.

6. The method of claim 1, wherein the switching strand and the competing strand do not have an overlapping region.

7. The method of claim 1, wherein the switching strand and the competing strand have substantially the same sequence.

8. The method of claim 1, wherein the switching strand and the competing strand are separated by one or more nucleotides.

9. The method of claim 1, wherein said conformation change enhances said ability of said substrate to be processed by RNase III to produce said siRNA or miRNA.

10. The method of claim 9, wherein the extent of the conformation change is amenable to adjustment or tuning.

11. The method of claim 10, wherein said adjustment or tuning is effectuated by modifying base-pairing interactions formed between the general transmission region and the switching strand, and/or base-pairing interactions formed between the general transmission region and the competing strand.

12. The method of claim 11, wherein said modifying is effectuated by changing the length of base pairs at one or both ends of the duplex formed between the general transmission region and the switching strand, and/or the duplex formed between the general transmission region and the competing strand.

13. The method of claim 11, wherein said modifying is effectuated by changing base-pairing complementarity.

14. The method of claim 10, wherein said adjustment or tuning is effectuated by changing the binding affinity between the modular sensor domain and the molecule without changing the size of the modular sensor domain.

15. The method of claim 10, wherein said adjustment or tuning is effectuated by changing the size of the modular sensor domain.

* * * * *

SEQUENCE LISTING

<160> NUMBER OF SEQ ID NOS: 47

<210> SEQ ID NO 1
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
ucccgcgacg augcccuca tt                                               22

<210> SEQ ID NO 2
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
ugaggggcau cgucgcggga tt                                              22

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
ucguccagga uggccgcggt t                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
ccgcggccau ccuggacgat t                                               21

<210> SEQ ID NO 5
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggatccacta ccgttgttat aggtgttcaa gagacaccta taacaacggt agttttttgg     60

```
aaaagctt                                                            68

<210> SEQ ID NO 6
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggatccggtg cagatgaact tcagggtcag ctcgagtcta gagctgaccc tgaatcatct    60
gcaccttttt tggaagctt                                                79

<210> SEQ ID NO 7
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggatccggct tcccaacgat gatgcaactc ctcgagtcta gaggagttgc atcagttggg    60
aagccttttt tggaagctt                                                79

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctcgagatac cagcatcgac tcttcgatgc ccttggcagc tcgggctgac cctgactaga    60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctcgaggacc cagcatcgac tcttcgatgc aaatggcagc tcgggctgac cctgactaga    60

<210> SEQ ID NO 10
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctcgagatac cagcatcgac tcttcgatgc ccttggcagc tcgggctgac cctgaagcta    60
ga                                                                  62

<210> SEQ ID NO 11
<211> LENGTH: 61
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 11
ctcgagatac cagcatcgac tcttcgatgc ccttggcagc tcgggctgac cctgaactag    60
a                                                                    61

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 12
ctcgagatac cagcatcgac tcttcgatgc ccttggcagc tcgggctgac cctgctaga     59

<210> SEQ ID NO 13
<211> LENGTH: 58
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 13
ctcgagatac cagcatcgac tcttcgatgc ccttggcagc tcgggctgac cctctaga      58

<210> SEQ ID NO 14
<211> LENGTH: 61
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 14
ctcgacgata ccagcatcga ctcttcgatg cccttggcag cgtcgggctg accctgctag    60
a                                                                    61

<210> SEQ ID NO 15
<211> LENGTH: 55
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 15
ctcgatacca gcatcgactc ttcgatgccc ttggcagcga gctgaccctg ctaga         55

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 16
ctcgagatac cagcatcgac tcttcgatgc ccttggcagc tcgagctgac cctgctaga     59

<210> SEQ ID NO 17
<211> LENGTH: 59

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctcgagatac cagcatcgac tcttcgatgc ccttggcagc tcgagctgat cctgctaga      59

<210> SEQ ID NO 18
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctcgatacca gcatcgactc ttcgatgccc ttggcagcga gctgaccctg actaga         56

<210> SEQ ID NO 19
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctcgagatac cagccgaaag gcccttggca gctcgggctg accctgacta ga             52

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctcgagatac caccgaaagg ccttggcagc tcgggctgac cctgactaga                50

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctcgagatac cagccgaaag gcccttggca gctcgggctg accctgctag a              51

<210> SEQ ID NO 22
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctcgatacca gccgaaaggc ccttggcagc gagctgaccc tgctaga                   47

<210> SEQ ID NO 23
<211> LENGTH: 47
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 23
ctcgatacca gccgaaaggc ccttggcagc gggctgaccc tgctaga          47

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctcgatacca gccgaaaggc ccttggcagc gagctgaccc tgactaga         48

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctcgagatac cagccgaaag gcccttggca gctcgagctg accctgctag a     51

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctcgagatac cagccgaaag gcccttggca gctcgagctg accctactag a     51

<210> SEQ ID NO 27
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctcgagatac cagccgaaag gcccttggca gctcgggctg accctgaact aga   53

<210> SEQ ID NO 28
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctcgagatac cagccgaaag gcccttggca gctcgggctg accctgaagc taga  54

<210> SEQ ID NO 29
<211> LENGTH: 52
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 29
ctcgagatac cagccgaaag gcccttggca gctcgggctg accctggcta ga              52

<210> SEQ ID NO 30
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctcgatacca gccgaaaggc ccttggcagc gagctgaccc tgaactaga                  49

<210> SEQ ID NO 31
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctcgagatac cagccgaaag gcccttggca gctcgagctg atcctgctag a               51

<210> SEQ ID NO 32
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctcgagatac cagccgaaag gcccttggca gctcgggctg atcctgctag a               51

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctcgagatac cagccgaaag gcccttggca gctcgggctg atcctgacta ga              52

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctcgagtgta ttacccagcg aggtcgactc gagctgaccc tgactaga                   48

<210> SEQ ID NO 35
<211> LENGTH: 47
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 35
ctcgagttca aacccagcga ggtacactcg agctgaccct gactaga                  47

<210> SEQ ID NO 36
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctcgagtgta ttacccagcg aggtcgactc gagctgaccc tgaactaga                49

<210> SEQ ID NO 37
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ctcgagtgta ttacccagcg aggtcgactc gagctgaccc tgctaga                  47

<210> SEQ ID NO 38
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ctcgaaaaca taccagagaa atctggagag gtgaagaata cgaccacctc gagctgaccc    60
tgactaga                                                             68

<210> SEQ ID NO 39
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctcgaaaaca taccagagaa atctggagag gtgaagaata cgaccacctc gagctgaccc    60
tgaactaga                                                            69

<210> SEQ ID NO 40
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctcgaaaaca taccagagaa atctggagag gtgaagaata cgaccacctc gagctgaccc    60
tgctaga                                                              67
```

```
<210> SEQ ID NO 41
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctcgagatac cagccgaaag gcccttggca gctcgaggag ttgcatccta ga           52

<210> SEQ ID NO 42
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctcgagatac cagccgaaag gcccttggca gctcgaggag ttgcattcta ga           52

<210> SEQ ID NO 43
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctcgagatac cagccgaaag gcccttggca gcttgaggag ttgcatccta ga           52

<210> SEQ ID NO 44
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctcgagatac cagccgaaag gcccttggca gcttgaggag ttgcatacta ga           52

<210> SEQ ID NO 45
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctcgagatac cagccgaaag gcccttggca gctcgaggag ttgcactaga              50

<210> SEQ ID NO 46
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctcgagatac cagccgaaag gcccttggca gcttgaggag ttgcactaga              50

<210> SEQ ID NO 47
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttctaatacg actcactata ggg                                             23
```